United States Patent
Hsu

(10) Patent No.: US 11,390,657 B2
(45) Date of Patent: Jul. 19, 2022

(54) PEPTIDE ANALOGS

(71) Applicant: Adepthera LLC, Palo Alto, CA (US)

(72) Inventor: Sheau Yu Teddy Hsu, Menlo Park, CA (US)

(73) Assignee: Adepthera LLC, Palo Alto, CA (US)

( * ) Notice: Subject to any disclaimer, the term of this patent is extended or adjusted under 35 U.S.C. 154(b) by 0 days.

(21) Appl. No.: 16/922,850

(22) Filed: Jul. 7, 2020

(65) Prior Publication Data

US 2020/0339649 A1 Oct. 29, 2020

Related U.S. Application Data

(62) Division of application No. 16/016,235, filed on Jun. 22, 2018, now abandoned.

(60) Provisional application No. 62/527,680, filed on Jun. 30, 2017.

(51) Int. Cl.
| | |
|---|---|
| *C07K 14/575* | (2006.01) |
| *C07K 14/585* | (2006.01) |
| *A61K 47/60* | (2017.01) |
| *A61K 47/54* | (2017.01) |
| *A61K 45/06* | (2006.01) |
| *C07K 14/47* | (2006.01) |
| *C07K 14/655* | (2006.01) |
| *A61K 9/00* | (2006.01) |
| *A61K 38/00* | (2006.01) |

(52) U.S. Cl.
CPC ............ *C07K 14/575* (2013.01); *A61K 45/06* (2013.01); *A61K 47/542* (2017.08); *A61K 47/60* (2017.08); *C07K 14/47* (2013.01); *C07K 14/57527* (2013.01); *C07K 14/585* (2013.01); *C07K 14/655* (2013.01); *A61K 9/0019* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,239,107 B1 | 5/2001 | Gozes et al. | |
| 6,268,474 B1 | 7/2001 | Smith et al. | |
| 9,694,051 B2 | 7/2017 | Hsu et al. | |
| 10,058,592 B2 | 8/2018 | Hsu et al. | |
| 2006/0040859 A1 | 2/2006 | Kobayashi | |
| 2008/0020978 A1 | 1/2008 | Gegg et al. | |
| 2008/0026995 A1 | 1/2008 | Tosi et al. | |
| 2008/0113411 A1 | 5/2008 | Sheffer et al. | |
| 2008/0207501 A1 | 8/2008 | Erickson et al. | |
| 2008/0274952 A1 | 11/2008 | Soares et al. | |
| 2009/0036364 A1 | 2/2009 | Levy et al. | |
| 2009/0088387 A1 | 4/2009 | Castillio et al. | |
| 2009/0175821 A1 | 7/2009 | Bridon et al. | |
| 2009/0186817 A1 | 7/2009 | Ghosh et al. | |
| 2010/0048871 A1 | 2/2010 | Cho et al. | |
| 2010/0249104 A1 | 9/2010 | Liu et al. | |
| 2011/0190193 A1 | 8/2011 | Stroes | |
| 2013/0281374 A1 | 10/2013 | Levy et al. | |
| 2014/0155329 A1 | 6/2014 | Hsu et al. | |
| 2014/0249299 A1* | 9/2014 | Levy .................. | C07K 5/1024 530/399 |
| 2017/0014485 A1 | 1/2017 | Hsu et al. | |
| 2017/0037088 A1 | 2/2017 | Schellenberger et al. | |

FOREIGN PATENT DOCUMENTS

| | | | |
|---|---|---|---|
| WO | 2012138867 | 10/2012 | |
| WO | WO-2012138867 A2 * | 10/2012 | ............... A61P 9/10 |
| WO | 2013/059336 | 4/2013 | |
| WO | 2016/183479 | 11/2016 | |

OTHER PUBLICATIONS

Hubner et al. (2016) "Structure-guided development of heterodimer-selective GPCR ligands", Nature Communications, vol. 7. no. 1, pp. 1-12.
Ruzza Paolo et al. (2012) "Peptide-Receptor Ligands and Multivalent Approach" Anti-Cancer Agents in Medicinal Chemistry, vol. 12. No. 5, pp. 416-427.
Jacobson et al. (2010) "GPCR ligand-dendrimer (GLiDe) conjugates: future smart drugs?" Trends in Pharmacological Sciences. vol. 31. No. 12, pp. 575-579.
Hiller et al. (2013) "Class A G-Protein-Coupled Receptor (GPCR) Dimers and Bivalent Ligands" Journal of Medicinal Chemistry, vol. 56. No. 17, pp. 6542-6559.
Huang Bosh et al. (2020) "Design of bivalent ligands targeting putative GPCR dimersDRUG" Discovery Today. Elsevier. Amsterdam, vol. 26. No. 1, pp. 189-199.

* cited by examiner

*Primary Examiner* — Christina Bradley
(74) *Attorney, Agent, or Firm* — Pamela J. Sherwood; Bozicevic, Field & Francis LLP

(57) ABSTRACT

Analogs for CLR/RAMP receptor ligands are provided that have agonist, superagonist, antagonist, super-antagonist, or multiple receptor modulating activity. The analogs can be selective for one or more CLR/RAMP receptors, or can be pan-specific for multiple G protein-coupled receptors.

1 Claim, No Drawings

Specification includes a Sequence Listing.

SEQUENCE LISTING

```
<160> NUMBER OF SEQ ID NOS: 247

<210> SEQ ID NO 1
<211> LENGTH: 22
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is a Lys
<220> FEATURE:
<221> NAME/KEY: Misc_feature
<222> LOCATION: (2)..(2)
<223> OTHER INFORMATION: Xaa is an empty residue, histidine (His),
      acylated histidine (acyHis), arginine (Arg), acylated arginine
      (acyArg), lysine (Lys), or acylated lysine (acyLys)
<220> FEATURE:
<221> NAME/KEY: Misc_feature
<222> LOCATION: (3)..(3)
<223> OTHER INFORMATION: Xaa is glycine (Gly), a nonproteinogenic amino
      acid, or an empty residue
```

```
<220> FEATURE:
<221> NAME/KEY: Misc_feature
<222> LOCATION: (5)..(5)
<223> OTHER INFORMATION: Xaa is arginine (Arg), histidine (His), and
      lysine (Lys), or a nonproteinogenic amino acid and an empty
      residue
<220> FEATURE:
<221> NAME/KEY: Misc_feature
<222> LOCATION: (6)..(6)
<223> OTHER INFORMATION: Xaa is phenylalanine (Phe),  leucine (Leu),
      tyrosine (Tyr), a nonproteinogenic amino acid or an empty residue
<220> FEATURE:
<221> NAME/KEY: Misc_feature
<222> LOCATION: (8)..(8)
<223> OTHER INFORMATION: Xaa is  serine (Ser), threonine (Thr), tyrosine
      (Tyr), a nonproteinogenic amino acid, or an empty residue
<220> FEATURE:
<221> NAME/KEY: Misc_feature
<222> LOCATION: (10)..(10)
<223> OTHER INFORMATION: Xaa is a serine (Ser), threonine (Thr),
      tyrosine (Tyr), glutamine (Gln), asparagine (Asn), a
      nonproteinogenic amino acid, or an empty residue
<220> FEATURE:
<221> NAME/KEY: Misc_feature
<222> LOCATION: (11)..(11)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (12)..(12)
<223> OTHER INFORMATION: Xaa is a  glutamine (Gln), asparagine (Asn),
      Asp, Glu, a nonproteinogenic amino acid, or an empty residue;
<220> FEATURE:
<221> NAME/KEY: Misc_feature
<222> LOCATION: (13)..(13)
<223> OTHER INFORMATION: Xaa is a  histidine (His), arginine (Arg),
      lysine (Lys), glutamine (Gln), asparagine (Asn), a
      nonproteinogenic amino acid, or an empty residue;
<220> FEATURE:
<221> NAME/KEY: Misc_feature
<222> LOCATION: (14)..(14)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (15)..(15)
<223> OTHER INFORMATION: Xaa is a valine (Val), alanine (Ala), glycine
      (Gly), isoleucine (Ile), leucine (Leu), serine (Ser), threonine
      (Thr), tyrosine (Tyr), a nonproteinogenic amino acid, or an empty
      residue
<220> FEATURE:
<221> NAME/KEY: Misc_feature
<222> LOCATION: (16)..(16)
<223> OTHER INFORMATION: Xaa is a histidine (His), arginine (Arg),
      lysine (Lys), a nonproteinogenic amino acid, or an empty residue
<220> FEATURE:
<221> NAME/KEY: Misc_feature
<222> LOCATION: (17)..(17)
<223> OTHER INFORMATION: Xaa is an empty residue, glutamine (Gln),
      asparagine (Asn), Asp, Glu, a nonproteinogenic amino acid, or an
      empty residue
<220> FEATURE:
<221> NAME/KEY: Misc_feature
<222> LOCATION: (18)..(18)
<223> OTHER INFORMATION: Xaa is a valine (Val), alanine (Ala), glycine
      (Gly), isoleucine (Ile), leucine (Leu), a nonproteinogenic amino
      acid, or an empty residue;
<220> FEATURE:
<221> NAME/KEY: Misc_feature
<222> LOCATION: (19)..(19)
<223> OTHER INFORMATION: Xaa is a tryptophan (Trp), phenylalanine (Phe),
      serine (Ser), threonine (Thr), tyrosine (Tyr), a nonproteinogenic
      amino acid, or an empty residue
<220> FEATURE:
<221> NAME/KEY: Misc_feature
<222> LOCATION: (20)..(20)
<223> OTHER INFORMATION: Xaa is a glutamine (Gln), glutamic acid (Glu),
```

```
      aspartic acid (Asp), asparagine (Asn), a nonproteinogenic amino
      acid, or an empty residue
<220> FEATURE:
<221> NAME/KEY: Misc_feature
<222> LOCATION: (21)..(21)
<223> OTHER INFORMATION: Xaa is a tryptophan (Trp), phenylalanine (Phe),
      valine (Val), alanine (Ala), glycine (Gly), isoleucine (Ile),
      leucine (Leu), a nonproteinogenic amino acid, or an empty residue
<220> FEATURE:
<221> NAME/KEY: Misc_feature
<222> LOCATION: (22)..(22)
<223> OTHER INFORMATION: Xaa is a serine (Ser), threonine (Thr), and
      tyrosine (Tyr); methionine (Met), tryptophan (Trp), phenylalanine
      (Phe), a nonproteinogenic amino acid, or an empty residue.

<400> SEQUENCE: 1

Xaa Xaa Xaa Cys Xaa Xaa Gly Xaa Cys Xaa Xaa Xaa Xaa Xaa Xaa
1               5                   10                  15

Xaa Xaa Xaa Xaa Xaa Xaa
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 2

Lys Gly Cys Arg Phe Gly Thr Cys Thr Val Gln Lys Leu Ala His Gln
1               5                   10                  15

Ile Tyr Gln Phe Thr
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 3

Lys Gly Cys Arg Phe Gly Thr Cys Thr Val Gln Lys Leu Ala His Leu
1               5                   10                  15

Trp Gln Leu Met
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 4

Lys Gly Cys Arg Phe Gly Thr Cys Thr Val Gln Lys Leu Ala His Gln
1               5                   10                  15

Ile Tyr Gln Phe Thr
            20

<210> SEQ ID NO 5
<211> LENGTH: 20
```

```
<212> TYPE: PRT
<213> ORGANISM: Artificial Sequence
<220> FEATURE:
<223> OTHER INFORMATION: Synthetic Sequence

<400> SEQUENCE: 5

Lys Gly Cys Arg Phe Gly Thr Cys Thr Val Gln Lys Leu Ala His Leu
1               5                   10                  15

Trp Gln Leu Met
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 6

Lys Gly Cys Arg Phe Gly Thr Cys Thr Val Gln Lys Leu Ala His Gln
1               5                   10                  15

Ile Tyr Gln Phe Thr
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 7

Lys Gly Cys Arg Phe Gly Thr Cys Thr Val Gln Lys Leu Ala His Leu
1               5                   10                  15

Trp Gln Leu Met
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 8

Lys Gly Cys Arg Phe Gly Thr Cys Thr Val Gln Lys Leu Ala His Gln
1               5                   10                  15

Ile Tyr Gln Phe Thr
            20

<210> SEQ ID NO 9
<211> LENGTH: 28
```

```
<212> TYPE: PRT
<213> ORGANISM: Artificial Sequence
<220> FEATURE:
<223> OTHER INFORMATION: Synthetic Sequence

<400> SEQUENCE: 9

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 10

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 11

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr
            20                  25

<210> SEQ ID NO 12
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 12

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr
            20                  25

<210> SEQ ID NO 13
<211> LENGTH: 20
```

```
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 13

Lys Cys Arg Phe Gly Thr Cys Thr Val Gln Lys Leu Ala His Gln Ile
1               5                   10                  15

Tyr Gln Phe Thr
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 14

Lys Cys Arg Phe Gly Thr Cys Thr Val Gln Lys Leu Ala His Gln Ile
1               5                   10                  15

Tyr Gln Phe Thr
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 15

Gly Cys Arg Phe Gly Thr Cys Thr Val Gln Lys Leu Ala His Gln Ile
1               5                   10                  15

Tyr Gln Phe Thr
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 16

Cys Arg Phe Gly Thr Cys Thr Val Gln Lys Leu Ala His Gln Ile Tyr
1               5                   10                  15

Gln Phe Thr

<210> SEQ ID NO 17
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is an empty residue, glutamine (Gln),
      glutamic acid (Glu), aspartic acid (Asp), asparagine (Asn),
      proline (Pro), or a non-proteinogenic amino acid
<220> FEATURE:
```

```
<221> NAME/KEY: Misc_feature
<222> LOCATION: (2)..(2)
<223> OTHER INFORMATION: Xaa is an empty residue, histidine (His),
      arginine (Arg), lysine (Lys), valine (Val), alanine (Ala), glycine
      (Gly), isoleucine (Ile), leucine (Leu), or a non-proteinogenic
      amino acid
<220> FEATURE:
<221> NAME/KEY: Misc_feature
<222> LOCATION: (3)..(3)
<223> OTHER INFORMATION: Xaa is an empty residue, glutamine (Gln),
      glutamic acid (Glu), aspartic acid (Asp), asparagine (Asn), valine
      (Val), alanine (Ala), glycine (Gly), isoleucine (Ile), leucine
      (Leu), or a non-proteinogenic amino acid
<220> FEATURE:
<221> NAME/KEY: Misc_feature
<222> LOCATION: (4)..(4)
<223> OTHER INFORMATION: Xaa is an empty residue, histidine (His),
      arginine (Arg), lysine (Lys), or a non-proteinogenic amino acid
<220> FEATURE:
<221> NAME/KEY: Misc_feature
<222> LOCATION: (5)..(5)
<223> OTHER INFORMATION: Xaa is an empty residue, aspartic acid (Asp),
      glutamic acid (Glu), glutamine (Gln), asparagine (Asn), or a
      non-proteinogenic amino acid
<220> FEATURE:
<221> NAME/KEY: Misc_feature
<222> LOCATION: (6)..(6)
<223> OTHER INFORMATION: Xaa is an empty residue, aspartic acid (Asp),
      glutamic acid (Glu), glutamine (Gln), asparagine (Asn), or a
      non-proteinogenic amino acid
<220> FEATURE:
<221> NAME/KEY: Misc_feature
<222> LOCATION: (7)..(7)
<223> OTHER INFORMATION: Xaa is an empty residue, valine (Val), alanine
      (Ala), glycine (Gly), isoleucine (Ile), leucine (Leu), serine
      (Ser), threonine (Thr), tyrosine (Tyr), or a non-proteinogenic
      amino acid
<220> FEATURE:
<221> NAME/KEY: Misc_feature
<222> LOCATION: (8)..(8)
<223> OTHER INFORMATION: Xaa is an empty residue, valine (Val), alanine
      (Ala), glycine (Gly), isoleucine (Ile), leucine (Leu), or a
      non-proteinogenic amino acid
<220> FEATURE:
<221> NAME/KEY: Misc_feature
<222> LOCATION: (9)..(9)
<223> OTHER INFORMATION: Xaa is an empty residue, proline (Pro), valine
      (Val), alanine (Ala), glycine (Gly), isoleucine (Ile), leucine
      (Leu), or a non-proteinogenic amino acid
<220> FEATURE:
<221> NAME/KEY: Misc_feature
<222> LOCATION: (10)..(10)
<223> OTHER INFORMATION: Xaa is an empty residue, valine (Val), alanine
      (Ala), glycine (Gly), isoleucine (Ile), leucine (Leu), histidine
      (His), arginine (Arg), lysine (Lys), or a non-proteinogenic amino
      acid
<220> FEATURE:
<221> NAME/KEY: Misc_feature
<222> LOCATION: (11)..(11)
<223> OTHER INFORMATION: Xaa is an empty residue, aspartic acid (Asp),
      glutamic acid (Glu), glutamine (Gln), asparagine (Asn), serine
      (Ser), threonine (Thr), tyrosine (Tyr), or a non-proteinogenic
      amino acid
<220> FEATURE:
<221> NAME/KEY: Misc_feature
<222> LOCATION: (12)..(12)
<223> OTHER INFORMATION: Xaa is an empty residue, histidine (His),
      arginine (Arg), lysine (Lys), proline (Pro), or a
      non-proteinogenic amino acid.

<400> SEQUENCE: 17

Xaa Xaa Xaa Xaa Xaa Xaa Xaa Xaa Xaa Xaa Xaa Xaa
1               5                   10

<210> SEQ ID NO 18
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 18

Asp Lys Asp Lys Asp Asn Val Ala Pro Arg Ser Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 19

Asp Lys Asp Lys Asp Asn Ser Ala Pro Val Asp Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 20

Pro Ala Gly Arg Gln Asp Ser Ala Pro Val Asp Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 21

Asp Lys Asp Lys Asp Asn Val Ala Pro Val Asp Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 22

Asp Lys Asp Lys Gln Asp Ser Ala Pro Val Asp Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 23

Asp Lys Gly Arg Gln Asp Ser Ala Pro Val Asp Pro
1               5                   10

<210> SEQ ID NO 24
<211> LENGTH: 11
<212> TYPE: PRT
<213> ORGANISM: Artificial Sequence
```

```
<220> FEATURE:
<223> OTHER INFORMATION: Synthetic Sequence

<400> SEQUENCE: 24

Asp Lys Asp Lys Asp Ser Ala Pro Val Asp Pro
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 25

Asp Lys Asp Lys Ser Ala Pro Val Asp Pro
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 26

Asp Lys Asp Ser Ala Pro Val Asp Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is an empty residue, Val, Ala, Gly, Ile,
      Leu, Ser, Thr, Tyr, or a non-proteinogenic amino acid
<220> FEATURE:
<221> NAME/KEY: Misc_feature
<222> LOCATION: (2)..(2)
<223> OTHER INFORMATION: Xaa is an empty residue, Ser, Thr, Tyr, or a
      non-proteinogenic amino acid
<220> FEATURE:
<221> NAME/KEY: Misc_feature
<222> LOCATION: (3)..(3)
<223> OTHER INFORMATION: Xaa is an empty residue, Pro, Val, Ala, Gly,
      Ile, Leu, or a non-proteinogenic amino acid
<220> FEATURE:
<221> NAME/KEY: Misc_feature
<222> LOCATION: (4)..(4)
<223> OTHER INFORMATION: Xaa is an empty residue, Asn, Gln, His, Arg,
      Lys, or a non-proteinogenic amino acid;
<220> FEATURE:
<221> NAME/KEY: Misc_feature
<222> LOCATION: (5)..(5)
<223> OTHER INFORMATION: Xaa is an empty residue, Val, Ala, Gly, Ile,
      Leu, Ser, Thr, Tyr, or a non-proteinogenic amino acid
<220> FEATURE:
<221> NAME/KEY: Misc_feature
<222> LOCATION: (6)..(6)
<223> OTHER INFORMATION: Xaa is a Ser, Thr, Tyr, or a non-proteinogenic
      amino acid

<400> SEQUENCE: 27

Xaa Xaa Xaa Xaa Xaa Xaa
1               5

<210> SEQ ID NO 28
```

```
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 28

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 29

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 30

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 31
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 31

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
```

-continued

```
                20                  25                  30

Pro Ser Ser Pro His Ser Tyr
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 32

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 33

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 34
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 34

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
        35

<210> SEQ ID NO 35
<211> LENGTH: 39
<212> TYPE: PRT
<213> ORGANISM: Artificial Sequence
<220> FEATURE:
<223> OTHER INFORMATION: Synthetic Sequence
```

```
<400> SEQUENCE: 35

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
            20                  25                  30

Pro Ser Ser Pro His Ser Tyr
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 36

Lys Gly Cys Arg Phe Gly Thr Cys Thr Val Gln Lys Leu Ala His Gln
1               5                   10                  15

Ile Tyr Gln Phe Thr Asp Lys Gly Arg Gln Asp Ser Ala Pro Val Asp
            20                  25                  30

Pro Ser Ser Pro His Ser Tyr
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 37

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 38
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 38

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Ser Ala Pro Val Asp Pro Ser Ser Pro His Ser Tyr
        35                  40                  45

<210> SEQ ID NO 39
<211> LENGTH: 45
<212> TYPE: PRT
<213> ORGANISM: Artificial Sequence
```

```
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 39

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Ser Ala Pro Val Asp Pro Ser Ser Pro His Ser Tyr
        35                  40                  45

<210> SEQ ID NO 40
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 40

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Val Ala Pro Val Asp Pro Ser Ser Pro His Ser Tyr
        35                  40                  45

<210> SEQ ID NO 41
<211> LENGTH: 45
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 41

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 42
<211> LENGTH: 45
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: There is a Palmitate Moiety conjugated to the
      Lys

<400> SEQUENCE: 42

Thr Lys Lys Thr Leu Arg Thr Gly Cys Arg Phe Gly Thr Cys Thr Val
1               5                   10                  15
```

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 43
<211> LENGTH: 38
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 43

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 44
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 44

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 45
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 45

Gly Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 46
<211> LENGTH: 38
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)

<223> OTHER INFORMATION: There is a Palmitate Moiety conjugated to the
      Lys

<400> SEQUENCE: 46

Lys Gly Cys Arg Phe Gly Thr Cys Thr Val Gln Lys Leu Ala His Gln
1               5                   10                  15

Ile Tyr Gln Phe Thr Asp Lys Asp Lys Asp Ser Ala Pro Val Asp Pro
            20                  25                  30

Ser Ser Pro His Ser Tyr
            35

<210> SEQ ID NO 47
<211> LENGTH: 37
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 47

Lys Gly Cys Arg Phe Gly Thr Cys Thr Val Gln Lys Leu Ala His Gln
1               5                   10                  15

Ile Tyr Gln Phe Thr Asp Lys Asp Lys Ser Ala Pro Val Asp Pro Ser
            20                  25                  30

Ser Pro His Ser Tyr
            35

<210> SEQ ID NO 48
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 48

Lys Gly Cys Arg Phe Gly Thr Cys Thr Val Gln Lys Leu Ala His Gln
1               5                   10                  15

Ile Tyr Gln Phe Thr Asp Lys Ser Ala Pro Val Asp Pro Ser Ser
            20                  25                  30

Pro His Ser Tyr
        35

<210> SEQ ID NO 49
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 49

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 50

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
        35

<210> SEQ ID NO 51
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 51

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
            20                  25                  30

Pro Ser Ser Pro His Ser Tyr
        35

<210> SEQ ID NO 52
<211> LENGTH: 40
<212> TYPE: PRT
<213> ORGANISM: Homo Sapiens

<400> SEQUENCE: 52

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40

<210> SEQ ID NO 53
<211> LENGTH: 39
<212> TYPE: PRT
<213> ORGANISM: Homo Sapiens

<400> SEQUENCE: 53

```
Phe Gly Cys Arg Phe Gly Thr Cys Thr Val Gln Lys Leu Ala His Gln
1               5                   10                  15

Ile Tyr Gln Phe Thr Asp Lys Asp Asp Asn Val Ala Pro Arg Ser
            20                  25                  30

Lys Ile Ser Pro Gln Gly Tyr
        35
```

```
<210> SEQ ID NO 54
<211> LENGTH: 52
<212> TYPE: PRT
<213> ORGANISM: Homo Sapiens

<400> SEQUENCE: 54

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50
```

```
<210> SEQ ID NO 55
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 55

Val Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35
```

```
<210> SEQ ID NO 56
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 56

Val Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35
```

```
<210> SEQ ID NO 57
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 57

Val Gly Cys Arg Phe Gly Thr Cys Thr Val Gln Lys Leu Ala His Gln
```

```
1               5                   10                  15
Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 58
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 58

Val Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 59
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 59

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 60
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 60

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
        35

<210> SEQ ID NO 61
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 61
```

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35

<210> SEQ ID NO 62
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 62

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 63
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 63

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35

<210> SEQ ID NO 64
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 64

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 65
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 65

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35

<210> SEQ ID NO 66
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 66

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 67
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 67

Cys Arg Phe Gly Thr Cys Thr Val Gln Lys Leu Ala His Gln Ile Tyr
1               5                   10                  15

Gln Phe Thr Asp Lys Asp Lys Asp Asn Ser Ala Pro Val Asp Pro Ser
            20                  25                  30

Ser Pro His Ser Tyr
        35

<210> SEQ ID NO 68
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 68

Lys Gly Cys Arg Phe Gly Thr Cys Thr Val Gln Lys Leu Ala His Gln
1               5                   10                  15

Ile Tyr Gln Phe Thr Asp Lys Gly Arg Gln Asp Ser Ala Pro Val Asp
            20                  25                  30

Pro Ser Ser Pro His Ser Tyr
        35

```
<210> SEQ ID NO 69
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 69

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 70
<211> LENGTH: 46
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 70

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Val Ala Pro Arg Ser Lys Ile Ser Pro Gln Gly Tyr
            35                  40                  45

<210> SEQ ID NO 71
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 71

Gly Cys Arg Phe Gly Thr Cys Thr Val Gln Lys Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln Gly Tyr
        35

<210> SEQ ID NO 72
<211> LENGTH: 52
<212> TYPE: PRT
<213> ORGANISM: Artificial Sequence
<220> FEATURE:
<223> OTHER INFORMATION: Synthetic Sequence

<400> SEQUENCE: 72

Tyr Arg Gln Ser Met Asn Asn Phe Gln Gly Leu Arg Ser Phe Gly Cys
1               5                   10                  15
```

-continued

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 73
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 73

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 74
<211> LENGTH: 38
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 74

Lys Gly Cys Asp Thr Ala Thr Cys Val Thr His Arg Leu Ala Gly Leu
1               5                   10                  15

Leu Ser Arg Ser Gly Gly Val Val Lys Asn Asn Phe Val Pro Thr Asn
            20                  25                  30

Val Gly Ser Lys Ala Phe
        35

<210> SEQ ID NO 75
<211> LENGTH: 31
<212> TYPE: PRT
<213> ORGANISM: Homo Sapiens

<400> SEQUENCE: 75

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 76

Thr Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 77

Thr Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 78
<211> LENGTH: 31
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 78

Lys Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 79
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 79

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 80
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 80

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala

```
                    20                  25                  30

Ala Ala Ala Ala
        35

<210> SEQ ID NO 81
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 81

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
                20                  25                  30

Ala Ala Ala Ala
        35

<210> SEQ ID NO 82
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 82

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
                20                  25                  30

Ala Ala Ala Ala
        35

<210> SEQ ID NO 83
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 83

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
                20                  25                  30

Ala Ala Ala Ala
        35

<210> SEQ ID NO 84
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 84

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
                20                  25                  30

Ala Ala Ala Ala
```

-continued

```
                35

<210> SEQ ID NO 85
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 85

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 86
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 86

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 87
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 87

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 88
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 88

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35
```

```
<210> SEQ ID NO 89
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 89

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 90
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 90

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 91
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 91

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 92
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 92

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30

Pro His Ser Tyr
        35

<210> SEQ ID NO 93
<211> LENGTH: 36
<212> TYPE: PRT
```

<213> ORGANISM: Artificial Sequence
<220> FEATURE:
<223> OTHER INFORMATION: Synthetic Sequence

<400> SEQUENCE: 93

```
Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30

Pro His Ser Tyr
        35
```

<210> SEQ ID NO 94
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the Lys

<400> SEQUENCE: 94

```
Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Asp Pro Ser Ser
            20                  25                  30

Pro His Ser Tyr
        35
```

<210> SEQ ID NO 95
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 95

```
Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35
```

<210> SEQ ID NO 96
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 96

```
Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35
```

<210> SEQ ID NO 97

```
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 97

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 98
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 98

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 99
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 99

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 100
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 100

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 101
<211> LENGTH: 36
<212> TYPE: PRT
<213> ORGANISM: Artificial Sequence
```

```
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 101

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
                20                  25                  30

Pro Gln Gly Tyr
            35

<210> SEQ ID NO 102
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 102

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
                20                  25                  30

Ala Ala Ala Ala
            35

<210> SEQ ID NO 103
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 103

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
                20                  25                  30

Pro Gln Gly Tyr
            35

<210> SEQ ID NO 104
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 104

Ala Cys Asp Thr Ala Thr Cys Val Thr His Arg Leu Ala Gly Leu Leu
1               5                   10                  15

Ser Arg Phe Thr Asp Lys Asp Lys Asp Asn Val Ala Pro Arg Ser Lys
                20                  25                  30

Ile Ser Pro Gln Gly Tyr
            35

<210> SEQ ID NO 105
<211> LENGTH: 39
```

<212> TYPE: PRT
<213> ORGANISM: Artificial Sequence
<220> FEATURE:
<223> OTHER INFORMATION: Synthetic Sequence

<400> SEQUENCE: 105

Phe Gly Cys Arg Phe Gly Thr Cys Thr Val Gln Lys Leu Ala His Arg
1               5                   10                  15

Leu Trp Gln Leu Met Gly Pro Asp Lys Asp Asn Val Ala Pro Arg Ser
            20                  25                  30

Lys Ile Ser Pro Gln Gly Tyr
        35

<210> SEQ ID NO 106
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 106

Ala Ala Ala Ala Ala Ala Ala Ala Ala Ala Ala Ala Ala Ala Ala Ala
1               5                   10                  15

Ala Ala Ala Ala Ala Ala Ala Ala Ala
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 107

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala
            20                  25

<210> SEQ ID NO 108
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 108

Ala Cys Asp Thr Ala Thr Cys Val Thr His Arg Leu Ala Gly Leu Leu
1               5                   10                  15

Ser Arg Ser Gly Gly Val Asn Phe Val Pro Thr Asn Val Gly Ser Lys
            20                  25                  30

Ala Phe

<210> SEQ ID NO 109
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 109

Ala Ala Ala Ala Ala Ala Ala Ala Ala Ala Ala Ala Ala Ala Ala Ala
1               5                   10                  15

-continued

Ala Ala Ala Ala Ala Ala Ala Ala Ala Ala Ala Ala
        20                  25                  30

Ala Ala Ala Ala
        35

<210> SEQ ID NO 110
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 110

Lys Gly Cys Arg Phe Gly Thr Cys Thr Val Gln Lys Leu Ala His Gln
1               5                   10                  15

Ile Tyr Gln Phe Thr Asp Lys Asp Ala Pro Val Asp Pro Ser Ser Pro
            20                  25                  30

His Ser Tyr
        35

<210> SEQ ID NO 111
<211> LENGTH: 53
<212> TYPE: PRT
<213> ORGANISM: Artificial Sequence
<220> FEATURE:
<223> OTHER INFORMATION: Synthetic Sequence

<400> SEQUENCE: 111

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala
    50

<210> SEQ ID NO 112
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 112

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 113
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 113

Ala Ala Ala Ala Ala Ala Ala Ala Ala Ala Ala Ala Ala Ala Ala Ala

```
                1               5                  10                  15
Ala Ala Ala Ala Ala Ala Ala Ala Ala Ala Ala Ala Ala Ala Ala Ala
                        20                  25                  30
Ala Ala Ala Ala Ala Ala Ala Ala Ala Ala Ala Ala Ala Ala Ala Ala
            35                  40                  45
Ala Ala Ala Ala Ala Ala Ala Ala Ala Ala
        50                  55
```

<210> SEQ ID NO 114
<211> LENGTH: 22
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the Lys

<400> SEQUENCE: 114

```
Lys Val Gln Lys Leu Ala His Gln Ile Tyr Ser Ala Pro Val Asp Pro
1               5                   10                  15

Ser Ser Pro His Ser Tyr
            20
```

<210> SEQ ID NO 115
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 115

```
Val Thr His Arg Leu Ala Gly Leu Leu Ser Arg Phe Thr Asp Lys Asp
1               5                   10                  15

Lys Asp Asn Val Ala Pro Arg Ser Lys Ile Ser Pro Gln Gly Tyr
            20                  25                  30
```

<210> SEQ ID NO 116
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 116

```
Thr Val Gln Lys Leu Ala His Arg Leu Trp Gln Leu Met Gly Pro Asp
1               5                   10                  15

Lys Asp Asn Val Ala Pro Arg Ser Lys Ile Ser Pro Gln Gly Tyr
            20                  25                  30
```

<210> SEQ ID NO 117
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 117

```
Val Thr His Arg Leu Ala Gly Leu Leu Ser Arg Phe Thr Asp Lys Asp
1               5                   10                  15

Lys Asp Asn Val Ala Pro Arg Ser Lys Ile Ser Pro Gln Gly Tyr
            20                  25                  30
```

```
<210> SEQ ID NO 118
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 118

Thr Val Gln Lys Leu Ala His Arg Leu Trp Gln Leu Met Gly Pro Asp
1               5                   10                  15

Lys Asp Asn Val Ala Pro Arg Ser Lys Ile Ser Pro Gln Gly Tyr
            20                  25                  30

<210> SEQ ID NO 119
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 119

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 120
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 120

Lys Val Gln Asn Leu Ser His Arg Leu Trp Gln Leu Met Gly Pro Ala
1               5                   10                  15

Gly Ser Ala Pro Val Asp Pro Ser Ser Pro His Ser Tyr
            20                  25

<210> SEQ ID NO 121
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 121

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 122
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 122

Lys Val Gln Lys Leu Ala His Gln Ile Tyr Ser Ala Pro Val Asp Pro
1               5                   10                  15

Ser Ser Pro His Ser Tyr
```

20

<210> SEQ ID NO 123
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 123

Lys Val Gln Lys Leu Ala His Gln Ile Ser Ala Pro Val Asp Pro Ser
1               5                   10                  15

Ser Pro His Ser Tyr
            20

<210> SEQ ID NO 124
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 124

Lys Val Gln Lys Leu Ala His Gln Ser Ala Pro Val Asp Pro Ser Ser
1               5                   10                  15

Pro His Ser Tyr
            20

<210> SEQ ID NO 125
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 125

Lys Val Gln Lys Leu Ala His Gln Ile Tyr Gln Phe Thr Asp Lys Ser
1               5                   10                  15

Ala Pro Val Asp Pro Ser Ser Pro His Ser Tyr
            20                  25

<210> SEQ ID NO 126
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 126

Ala Ala Ala Ala Ala Ala Ala Ala Ala Ala Ala
1               5                   10

<210> SEQ ID NO 127
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 127

Ala Ala Ala Ala Ala Ala Ala Ala Ala Ala Ala Ala Ala Ala Ala Ala
1               5                   10                  15

Ala

```
<210> SEQ ID NO 128
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 128

Ala Ala Ala Ala Ala Ala Ala Ala Ala Ala Ala Ala Ala Ala Ala Ala
1               5                   10                  15

Ala Ala Ala Ala
            20

<210> SEQ ID NO 129
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 129

Ala Ala Ala Ala Ala Ala Ala Ala Ala Ala Ala Ala Ala Ala Ala Ala
1               5                   10                  15

Ala Ala Ala Ala Ala Ala Ala Ala Ala
            20                  25

<210> SEQ ID NO 130
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 130

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala
            20                  25                  30

<210> SEQ ID NO 131
<211> LENGTH: 44
<212> TYPE: PRT
<213> ORGANISM: Artificial Sequence
<220> FEATURE:
<223> OTHER INFORMATION: Synthetic Sequence

<400> SEQUENCE: 131

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala
        35                  40

<210> SEQ ID NO 132
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 132

Ala Ala Ala Ala Ala Ala Ala Ala Ala Ala Ala Ala Ala Ala Ala Ala
1               5                   10                  15
```

Ala Ala Ala Ala Ala Ala Ala Ala Ala Ala Ala Ala
            20                  25                  30

Ala Ala Ala Ala Ala Ala Ala Ala Ala Ala Ala Ala
        35                  40                  45

Ala Ala
    50

<210> SEQ ID NO 133
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 133

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala
        35

<210> SEQ ID NO 134
<211> LENGTH: 51
<212> TYPE: PRT
<213> ORGANISM: Artificial Sequence
<220> FEATURE:
<223> OTHER INFORMATION: Synthetic Sequence

<400> SEQUENCE: 134

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala
    50

<210> SEQ ID NO 135
<211> LENGTH: 71
<212> TYPE: PRT
<213> ORGANISM: Artificial Sequence
<220> FEATURE:
<223> OTHER INFORMATION: Synthetic Sequence

<400> SEQUENCE: 135

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
    50                  55                  60

Ala Ala Ala Ala Ala Ala Ala
65                  70

<210> SEQ ID NO 136
<211> LENGTH: 76
<212> TYPE: PRT

```
<213> ORGANISM: Artificial Sequence
<220> FEATURE:
<223> OTHER INFORMATION: Synthetic Sequence

<400> SEQUENCE: 136

Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala
    50                  55                  60

Ala Ala Ala Ala Ala Ala Ala Ala Ala Ala Ala
65                  70                  75

<210> SEQ ID NO 137
<211> LENGTH: 30
<212> TYPE: PRT
<213> ORGANISM: Homo Sapiens

<400> SEQUENCE: 137

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 138
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 138

Ala Ala Ala Ala Ala Ala Ala Ala Ala Ala Ala Ala Ala Ala Ala Ala
1               5                   10                  15

Ala Ala Ala Ala Ala Ala
            20

<210> SEQ ID NO 139
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 139

Lys Val Gln Lys Leu Ser Ala Pro Val Asp Pro Ser Ser Pro His Ser
1               5                   10                  15

Tyr

<210> SEQ ID NO 140
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys
```

```
<400> SEQUENCE: 140

Lys Val Gln Lys Leu Ser Ala Pro Val Asp Pro Ser Ser Pro His Ser
1               5                   10                  15

Tyr

<210> SEQ ID NO 141
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 141

Lys Val Gln Asn Leu Ser Ala Pro Val Asp Pro Ser Ser Pro His Ser
1               5                   10                  15

Tyr

<210> SEQ ID NO 142
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 142

Lys Val Gln Lys Leu Asn Phe Val Pro Thr Asn Val Gly Ser Lys Ala
1               5                   10                  15

Phe

<210> SEQ ID NO 143
<211> LENGTH: 37
<212> TYPE: PRT
<213> ORGANISM: Homo Sapiens

<400> SEQUENCE: 143

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 144
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 144

Asn Phe Val Pro Thr Asn Val Gly Pro Phe Ala Phe
1               5                   10

<210> SEQ ID NO 145
<211> LENGTH: 22
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (2)..(2)
<223> OTHER INFORMATION: Ala is a D- isomer of Ala
<220> FEATURE:
```

```
<221> NAME/KEY: Misc_feature
<222> LOCATION: (5)..(5)
<223> OTHER INFORMATION: Leu is a D- isomer of Leu
<220> FEATURE:
<221> NAME/KEY: Misc_feature
<222> LOCATION: (6)..(6)
<223> OTHER INFORMATION: There is a Palmitate moiety conjugated to the
      Lys

<400> SEQUENCE: 145

Tyr Ala Gly Phe Leu Lys Val Gln Lys Leu Ser Ala Pro Val Asp Pro
1               5                   10                  15

Ser Ser Pro His Ser Tyr
            20

<210> SEQ ID NO 146
<211> LENGTH: 30
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (14)..(14)
<223> OTHER INFORMATION: There is a Palmitate Moiety conjugated to the
      Lys

<400> SEQUENCE: 146

Tyr Gly Gly Phe Leu Arg Arg Ile Arg Pro Lys Leu Lys Val Gln
1               5                   10                  15

Lys Leu Ser Ala Pro Val Asp Pro Ser Ser Pro His Ser Tyr
            20                  25                  30

<210> SEQ ID NO 147
<211> LENGTH: 47
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (12)..(12)
<223> OTHER INFORMATION: There is a Palmitate Moiety conjugated to the
      Lys

<400> SEQUENCE: 147

Arg Pro Lys Pro Gln Gln Phe Phe Gly Leu Met Lys Gly Cys Arg Phe
1               5                   10                  15

Gly Thr Cys Thr Val Gln Lys Leu Ala His Gln Ile Tyr Gln Phe Thr
            20                  25                  30

Asp Lys Asp Ser Ala Pro Val Asp Pro Ser Ser Pro His Ser Tyr
        35                  40                  45

<210> SEQ ID NO 148
<211> LENGTH: 38
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (11)..(11)
<223> OTHER INFORMATION: There is a Palmitate Moiety conjugated to the
      Lys

<400> SEQUENCE: 148

Tyr Asn Trp Asn Ser Phe Gly Leu Arg Phe Lys Val Gln Lys Leu Ala
1               5                   10                  15
```

His Gln Ile Tyr Gln Phe Thr Asp Lys Asp Val Ala Pro Arg Ser Lys
            20                  25                  30

Ile Ser Pro Gln Gly Tyr
        35

<210> SEQ ID NO 149
<211> LENGTH: 38
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (11)..(11)
<223> OTHER INFORMATION: There is a Palmitate Moiety conjugated to the
      Lys

<400> SEQUENCE: 149

Lys Arg Pro Pro Gly Phe Ser Pro Phe Arg Lys Val Gln Lys Leu Ala
1               5                   10                  15

His Gln Ile Tyr Gln Phe Thr Asp Lys Asp Val Ala Pro Arg Ser Lys
            20                  25                  30

Ile Ser Pro Gln Gly Tyr
        35

<210> SEQ ID NO 150
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_features
<222> LOCATION: (1)..(1)
<223> OTHER INFORMATION: There is a [19-carboxy-nonadecanoyl]-isoGlu-
      PEG3) conjugated to the Lys

<400> SEQUENCE: 150

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 151
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu) conjugated to
      the Lys

<400> SEQUENCE: 151

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 152
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3)
      conjugated to the Lys

<400> SEQUENCE: 152

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 153
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Hexadecanoyl-isoGlu-PEG3-PEG3
      conjugated to the Lys

<400> SEQUENCE: 153

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 154
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-PEG3-isoGlu)
      conjugated to the Lys

<400> SEQUENCE: 154

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 155
<211> LENGTH: 39
<212> TYPE: PRT
<213> ORGANISM: Artificial Sequence
<220> FEATURE:
<223> OTHER INFORMATION: Synthetic Sequence

```
<220> FEATURE:
<221> NAME/KEY: Misc_feature
<222> LOCATION: (1)..(1)
<223> OTHER INFORMATION: There is a ([19-carboxy-nonadecanoyl]-isoGlu)
      conjugated to the Lys

<400> SEQUENCE: 155

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 156
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-PEG3-
      isoGlu) conjugated to the Lys

<400> SEQUENCE: 156

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 157
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      Peg3-Peg3) conjugated to the Lys

<400> SEQUENCE: 157

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 158
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([17-carboxy-heptadecanoyl]-isoGlu-
      Peg3-Peg3) conjugated to the Lys

<400> SEQUENCE: 158
```

```
Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35
```

<210> SEQ ID NO 159
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 159

```
Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35
```

<210> SEQ ID NO 160
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu) conjugated to
      the Lys

<400> SEQUENCE: 160

```
Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35
```

<210> SEQ ID NO 161
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Hexadecanoyl-isoGlu-PEG3 conjugated
      to the Lys

<400> SEQUENCE: 161

```
Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30
```

Lys Ile Ser Pro Gln Gly Tyr
        35

<210> SEQ ID NO 162
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3-PEG3)
      conjugated to the Lys

<400> SEQUENCE: 162

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 163
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-PEG3-isoGlu)
      conjugated to the Lys

<400> SEQUENCE: 163

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 164
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu)
      conjugated to the Lys

<400> SEQUENCE: 164

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 165
<211> LENGTH: 39
<212> TYPE: PRT

```
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-PEG3-
      isoGlu) conjugated to the Lys

<400> SEQUENCE: 165

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 166
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3-PEG3) conjugated to the Lys

<400> SEQUENCE: 166

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 167
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([17-carboxy-heptadecanoyl]-isoGlu-
      PEG3-PEG3) conjugated to the Lys

<400> SEQUENCE: 167

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 168
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
```

PEG3) conjugated to the Lys

<400> SEQUENCE: 168

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 169
<211> LENGTH: 39
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 169

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 170
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu) conjugated to
      the Lys

<400> SEQUENCE: 170

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 171
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3)
      conjugated to the Lys

<400> SEQUENCE: 171

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 172
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3-PEG3) conjugated to the Lys

<400> SEQUENCE: 172

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 173
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-PEG3-isoGlu) conjugated to the Lys

<400> SEQUENCE: 173

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 174
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu) conjugated to the Lys

<400> SEQUENCE: 174

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 175
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-PEG3-isoGlu) conjugated to the Lys

<400> SEQUENCE: 175

Lys Val Gln Lys Leu Ala His Gln Ile Tyr Gln Phe Thr Asp Lys Asp

```
1               5                   10                  15
Ser Ala Pro Val Asp Pro Ser Ser Pro His Ser Tyr
            20                  25

<210> SEQ ID NO 176
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3-PEG3) conjugated to the Lys

<400> SEQUENCE: 176

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 177
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([17-carboxy-heptadecanoyl]-isoGlu-
      PEG3-PEG3) conjugated to the Lys

<400> SEQUENCE: 177

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 178
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 178

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 179
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
```

PEG3) conjugated to the Lys

<400> SEQUENCE: 179

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 180
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu) conjugated to
      the Lys

<400> SEQUENCE: 180

Lys Val Gln Lys Leu Ser Ala Pro Val Asp Pro Ser Ser Pro His Ser
1               5                   10                  15

Tyr

<210> SEQ ID NO 181
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3)
      conjugated to the Lys

<400> SEQUENCE: 181

Lys Val Gln Lys Leu Ser Ala Pro Val Asp Pro Ser Ser Pro His Ser
1               5                   10                  15

Tyr

<210> SEQ ID NO 182
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3-PEG3)
      conjugated to the Lys

<400> SEQUENCE: 182

Lys Val Gln Lys Leu Ser Ala Pro Val Asp Pro Ser Ser Pro His Ser
1               5                   10                  15

Tyr

<210> SEQ ID NO 183
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature

```
<222> LOCATION: (1)..(1)
<223> OTHER INFORMATION: There is a (Hexadecanoyl-PEG3-isoGlu)
      conjugated to the Lys

<400> SEQUENCE: 183

Lys Val Gln Lys Leu Ser Ala Pro Val Asp Pro Ser Ser Pro His Ser
1               5                   10                  15

Tyr

<210> SEQ ID NO 184
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu)
      conjugated to the Lys

<400> SEQUENCE: 184

Lys Val Gln Lys Leu Ser Ala Pro Val Asp Pro Ser Ser Pro His Ser
1               5                   10                  15

Tyr

<210> SEQ ID NO 185
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_features
<222> LOCATION: (1)..(1)
<223> OTHER INFORMATION: There is a ([19-carboxy-nonadecanoyl]-PEG3-
      isoGlu) conjugated to the Lys

<400> SEQUENCE: 185

Lys Val Gln Lys Leu Ser Ala Pro Val Asp Pro Ser Ser Pro His Ser
1               5                   10                  15

Tyr

<210> SEQ ID NO 186
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3-PEG3) conjugated to the Lys

<400> SEQUENCE: 186

Lys Val Gln Lys Leu Ser Ala Pro Val Asp Pro Ser Ser Pro His Ser
1               5                   10                  15

Tyr

<210> SEQ ID NO 187
<211> LENGTH: 17
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: Misc_feature
<222> LOCATION: (1)..(1)
<223> OTHER INFORMATION: There is a ([17-carboxy-heptadecanoyl]-isoGlu-
      PEG3-PEG3) conjugated to the Lys

<400> SEQUENCE: 187

Lys Val Gln Lys Leu Ser Ala Pro Val Asp Pro Ser Ser Pro His Ser
1               5                   10                  15

Tyr

<210> SEQ ID NO 188
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 188

Lys Val Gln Lys Leu Ser Ala Pro Val Asp Pro Ser Ser Pro His Ser
1               5                   10                  15

Tyr

<210> SEQ ID NO 189
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 189

Lys Val Gln Lys Leu Ser Ala Pro Val Asp Pro Ser Ser Pro His Ser
1               5                   10                  15

Tyr

<210> SEQ ID NO 190
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 190

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 191
<211> LENGTH: 28
<212> TYPE: PRT
<213> ORGANISM: Artificial Sequence
<220> FEATURE:
```

<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 191

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 192
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

<400> SEQUENCE: 192

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 193
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-PEG3-isoGlu)
      conjugated to the Lys

<400> SEQUENCE: 193

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 194
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu)
      conjugated to the Lys

<400> SEQUENCE: 194

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

```
<210> SEQ ID NO 195
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-PEG3-
      isoGlu) conjugated to the Lys

<400> SEQUENCE: 195

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 196
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_Feature
<222> LOCATION: (1)..(1)
<223> OTHER INFORMATION: There is a ([19-carboxy-nonadecanoyl]-isoGlu-
      PEG3-PEG3) conjugated to the Lys

<400> SEQUENCE: 196

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 197
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([17-carboxy-heptadecanoyl]-isoGlu-
      PEG3-PEG3) conjugated to the Lys

<400> SEQUENCE: 197

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 198
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 198

Lys Val Gln Lys Leu Ala His Gln Ile Tyr Gln Phe Thr Asp Lys Asp
1               5                   10                  15
```

```
Val Ala Pro Arg Ser Lys Ile Ser Pro Gln Gly Tyr
            20                  25

<210> SEQ ID NO 199
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 199

Val Gln Lys Leu Ala His Gln Ile Tyr Gln Phe Thr Asp Lys Asp Val
1               5                   10                  15

Ala Pro Arg Ser Lys Ile Ser Pro Gln Gly Tyr
            20                  25

<210> SEQ ID NO 200
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu) conjugated to
      the Lys

<400> SEQUENCE: 200

Lys Val Gln Lys Leu Asn Phe Val Pro Thr Asn Val Gly Ser Lys Ala
1               5                   10                  15

Phe

<210> SEQ ID NO 201
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3)
      conjugated to the Lys

<400> SEQUENCE: 201

Lys Val Gln Lys Leu Asn Phe Val Pro Thr Asn Val Gly Ser Lys Ala
1               5                   10                  15

Phe

<210> SEQ ID NO 202
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-isoGlu-PEG3-PEG3)
      conjugated to the Lys

<400> SEQUENCE: 202
```

```
Lys Val Gln Lys Leu Asn Phe Val Pro Thr Asn Val Gly Ser Lys Ala
1               5                   10                  15

Phe

<210> SEQ ID NO 203
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a (Hexadecanoyl-PEG3-isoGlu)
      conjugated to the Lys

<400> SEQUENCE: 203

Lys Val Gln Lys Leu Asn Phe Val Pro Thr Asn Val Gly Ser Lys Ala
1               5                   10                  15

Phe

<210> SEQ ID NO 204
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu)
      conjugated to the Lys

<400> SEQUENCE: 204

Lys Val Gln Lys Leu Asn Phe Val Pro Thr Asn Val Gly Ser Lys Ala
1               5                   10                  15

Phe

<210> SEQ ID NO 205
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-PEG3-
      isoGlu) conjugated to the Lys

<400> SEQUENCE: 205

Lys Val Gln Lys Leu Asn Phe Val Pro Thr Asn Val Gly Ser Lys Ala
1               5                   10                  15

Phe

<210> SEQ ID NO 206
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3-PEG3) conjugated to the Lys
```

<400> SEQUENCE: 206

Lys Val Gln Lys Leu Asn Phe Val Pro Thr Asn Val Gly Ser Lys Ala
1               5                   10                  15

Phe

<210> SEQ ID NO 207
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([17-carboxy-heptadecanoyl]-isoGlu-
      PEG3-PEG3) conjugated to the Lys

<400> SEQUENCE: 207

Lys Val Gln Lys Leu Asn Phe Val Pro Thr Asn Val Gly Ser Lys Ala
1               5                   10                  15

Phe

<210> SEQ ID NO 208
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 208

Lys Val Gln Lys Leu Asn Phe Val Pro Thr Asn Val Gly Ser Lys Ala
1               5                   10                  15

Phe

<210> SEQ ID NO 209
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a ([19-carboxy-nonadecanoyl]-isoGlu-
      PEG3) conjugated to the Lys

<400> SEQUENCE: 209

Lys Val Gln Lys Leu Asn Phe Val Pro Thr Asn Val Gly Ser Lys Ala
1               5                   10                  15

Phe

<210> SEQ ID NO 210
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys

```
<220> FEATURE:
<221> NAME/KEY: Misc_feature
<222> LOCATION: (9)..(9)
<223> OTHER INFORMATION: Thr is a D- isomer of Thr

<400> SEQUENCE: 210

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35

<210> SEQ ID NO 211
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys
<220> FEATURE:
<221> NAME/KEY: Misc_feature
<222> LOCATION: (10)..(10)
<223> OTHER INFORMATION: Val is a D- isomer of Val

<400> SEQUENCE: 211

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35

<210> SEQ ID NO 212
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys
<220> FEATURE:
<221> NAME/KEY: Misc_feature
<222> LOCATION: (16)..(16)
<223> OTHER INFORMATION: Gln is a D- isomer of Gln

<400> SEQUENCE: 212

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35

<210> SEQ ID NO 213
<211> LENGTH: 36
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: Misc_feature
<222> LOCATION: (1)..(1)
<223> OTHER INFORMATION: There is a Palmitate moiety conjugated to the
      Lys
<220> FEATURE:
<221> NAME/KEY: Misc_feature
<222> LOCATION: (29)..(29)
<223> OTHER INFORMATION: Ser is a D- isomer of Ser

<400> SEQUENCE: 213

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35

<210> SEQ ID NO 214
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: There is a Palmitate Moiety conjugated to the
      Lys
<220> FEATURE:
<221> NAME/KEY: Misc_feature
<222> LOCATION: (34)..(34)
<223> OTHER INFORMATION: Gln is a D- isomer of Gln

<400> SEQUENCE: 214

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35

<210> SEQ ID NO 215
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Phe is a D- isomer of Phe
<220> FEATURE:
<221> NAME/KEY: Misc_feature
<222> LOCATION: (4)..(4)
<223> OTHER INFORMATION: Trp is a D- isomer of Trp

<400> SEQUENCE: 215

Phe Cys Phe Trp Lys Thr Cys Thr
1               5

<210> SEQ ID NO 216
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 216
```

```
Ala Gly Cys Lys Asn Phe Phe Trp Lys Thr Phe Thr Ser Cys
1               5                   10
```

<210> SEQ ID NO 217
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 217

```
Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
                20                  25
```

<210> SEQ ID NO 218
<211> LENGTH: 37
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Phe is a D- isomer of Phe
<220> FEATURE:
<221> NAME/KEY: Misc_feature
<222> LOCATION: (4)..(4)
<223> OTHER INFORMATION: Trp is a D- isomer of Trp
<220> FEATURE:
<221> NAME/KEY: Misc_feature
<222> LOCATION: (9)..(9)
<223> OTHER INFORMATION: Xaa has the structure NH(CH2CH2O)2C(=O)
<220> FEATURE:
<221> NAME/KEY: Misc_feature
<222> LOCATION: (10)..(10)
<223> OTHER INFORMATION: There is a Palmitate Moiety conjugated to the
      Lys

<400> SEQUENCE: 218

```
Phe Cys Phe Trp Lys Thr Cys Thr Xaa Lys Val Gln Lys Leu Ala His
1               5                   10                  15

Gln Ile Tyr Gln Phe Thr Asp Lys Asp Val Ala Pro Arg Ser Lys Ile
                20                  25                  30

Ser Pro Gln Gly Tyr
                35
```

<210> SEQ ID NO 219
<211> LENGTH: 36
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Phe is a D- isomer of Phe
<220> FEATURE:
<221> NAME/KEY: Misc_feature
<222> LOCATION: (4)..(4)
<223> OTHER INFORMATION: Trp is a D- isomer of Trp
<220> FEATURE:
<221> NAME/KEY: Misc_feature
<222> LOCATION: (9)..(9)
<223> OTHER INFORMATION: There is a IsoGlu Palmitate Moiety conjugated
      to the Lys

<400> SEQUENCE: 219

```
Phe Cys Phe Trp Lys Thr Cys Thr Lys Val Gln Lys Leu Ala His Gln
1               5                   10                  15

Ile Tyr Gln Phe Thr Asp Lys Asp Val Ala Pro Arg Ser Lys Ile Ser
            20                  25                  30

Pro Gln Gly Tyr
        35
```

<210> SEQ ID NO 220
<211> LENGTH: 25
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Phe is a D- isomer of Phe
<220> FEATURE:
<221> NAME/KEY: Misc_feature
<222> LOCATION: (4)..(4)
<223> OTHER INFORMATION: Trp is a D- isomer of Trp
<220> FEATURE:
<221> NAME/KEY: Misc_feature
<222> LOCATION: (9)..(9)
<223> OTHER INFORMATION: There is a IsoGlu-Palmitate Moiety conjugated
      to the Lys

<400> SEQUENCE: 220

```
Phe Cys Phe Trp Lys Thr Cys Thr Lys Val Gln Lys Leu Ser Ala Pro
1               5                   10                  15

Val Asp Pro Ser Ser Pro His Ser Tyr
            20                  25
```

<210> SEQ ID NO 221
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp

<400> SEQUENCE: 221

```
Xaa Leu Tyr Glu Asn Lys Pro Arg Arg Pro Tyr Ile Leu
1               5                   10
```

<210> SEQ ID NO 222
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 222

```
Lys Lys Pro Tyr Ile Leu
1               5
```

<210> SEQ ID NO 223
<211> LENGTH: 49
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp

```
<220> FEATURE:
<221> NAME/KEY: Misc_feature
<222> LOCATION: (14)..(14)
<223> OTHER INFORMATION: There is a Palmitate moiety conjugated to the
      Lys

<400> SEQUENCE: 223

Xaa Leu Tyr Glu Asn Lys Pro Arg Arg Pro Tyr Ile Leu Lys Gly Cys
1               5                   10                  15
Arg Phe Gly Thr Cys Thr Val Gln Lys Leu Ala His Gln Ile Tyr Gln
            20                  25                  30
Phe Thr Asp Lys Asp Val Ala Pro Arg Ser Lys Ile Ser Pro Gln Gly
        35                  40                  45
Tyr

<210> SEQ ID NO 224
<211> LENGTH: 30
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp
<220> FEATURE:
<221> NAME/KEY: Misc_feature
<222> LOCATION: (14)..(14)
<223> OTHER INFORMATION: There is a Palmitate Moiety conjugated to the
      Lys

<400> SEQUENCE: 224

Xaa Leu Tyr Glu Asn Lys Pro Arg Arg Pro Tyr Ile Leu Lys Val Gln
1               5                   10                  15
Lys Leu Ser Ala Pro Val Asp Pro Ser Ser Pro His Ser Tyr
            20                  25                  30

<210> SEQ ID NO 225
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp

<400> SEQUENCE: 225

Xaa Arg Pro Arg Leu Ser His Lys Gly Pro Met Pro Phe
1               5                   10

<210> SEQ ID NO 226
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 226

Lys Phe Arg Arg Gln Arg Pro Arg Leu Ser His Lys Gly Pro Met Pro
1               5                   10                  15
Phe

<210> SEQ ID NO 227
<211> LENGTH: 36
```

```
<212> TYPE: PRT
<213> ORGANISM: Artificial Sequence
<220> FEATURE:
<223> OTHER INFORMATION: Synthetic Sequence

<400> SEQUENCE: 227

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
                20                  25                  30

Pro Met Pro Phe
        35

<210> SEQ ID NO 228
<211> LENGTH: 49
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp
<220> FEATURE:
<221> NAME/KEY: Misc_feature
<222> LOCATION: (11)..(11)
<223> OTHER INFORMATION: L is norleucine
<220> FEATURE:
<221> NAME/KEY: Misc_feature
<222> LOCATION: (14)..(14)
<223> OTHER INFORMATION: There is a Palmitate moiety conjugated to the
      Lys

<400> SEQUENCE: 228

Xaa Arg Pro Arg Leu Ser His Lys Gly Pro Leu Pro Phe Lys Gly Cys
1               5                   10                  15

Arg Phe Gly Thr Cys Thr Val Gln Lys Leu Ala His Gln Ile Tyr Gln
                20                  25                  30

Phe Thr Asp Lys Asp Val Ala Pro Arg Ser Lys Ile Ser Pro Gln Gly
            35                  40                  45

Tyr

<210> SEQ ID NO 229
<211> LENGTH: 49
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is Glp
<220> FEATURE:
<221> NAME/KEY: Misc_feature
<222> LOCATION: (11)..(11)
<223> OTHER INFORMATION: L is norleucine
<220> FEATURE:
<221> NAME/KEY: Misc_feature
<222> LOCATION: (13)..(13)
<223> OTHER INFORMATION: There is a Palmitate Moiety conjugated to the
      Lys

<400> SEQUENCE: 229

Xaa Arg Pro Arg Leu Ser His Lys Gly Pro Leu Pro Phe Lys Gly Cys
1               5                   10                  15

Arg Phe Gly Thr Cys Thr Val Gln Lys Leu Ala His Gln Ile Tyr Gln
                20                  25                  30
```

```
Phe Thr Asp Lys Asp Val Ala Pro Arg Ser Lys Ile Ser Pro Gln Gly
            35                  40                  45

Tyr

<210> SEQ ID NO 230
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 230

Lys Arg Pro Pro Gly Phe Ser Pro Phe
1               5

<210> SEQ ID NO 231
<211> LENGTH: 44
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (7)..(8)
<223> OTHER INFORMATION: There is a D(beta)Nal between the Serine and
      Isoleucine
<220> FEATURE:
<221> NAME/KEY: Misc_feature
<222> LOCATION: (9)..(9)
<223> OTHER INFORMATION: There is a Palmitate Moiety conjugated to the
      Lys

<400> SEQUENCE: 231

Lys Arg Pro Pro Gly Phe Ser Ile Lys Gly Cys Arg Phe Gly Thr Cys
1               5                   10                  15

Thr Val Gln Lys Leu Ala His Gln Ile Tyr Gln Phe Thr Asp Lys Asp
            20                  25                  30

Val Ala Pro Arg Ser Lys Ile Ser Pro Gln Gly Tyr
            35                  40

<210> SEQ ID NO 232
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 232

Asp Arg Val Tyr Ile His Pro Phe
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 233

Arg Val Tyr Val His Pro Ala
1               5

<210> SEQ ID NO 234
<211> LENGTH: 43
<212> TYPE: PRT
<213> ORGANISM: Artificial Sequence
<220> FEATURE:
```

-continued

<223> OTHER INFORMATION: Synthetic Sequence
<220> FEATURE:
<221> NAME/KEY: Misc_feature
<222> LOCATION: (8)..(8)
<223> OTHER INFORMATION: There is a Palmitate moiety conjugated to the
      Lys

<400> SEQUENCE: 234

Arg Val Tyr Val His Pro Ala Lys Gly Cys Arg Phe Gly Thr Cys Thr
1               5                   10                  15

Val Gln Lys Leu Ala His Gln Ile Tyr Gln Phe Thr Asp Lys Asp Val
            20                  25                  30

Ala Pro Arg Ser Lys Ile Ser Pro Gln Gly Tyr
        35                  40

<210> SEQ ID NO 235
<211> LENGTH: 29
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is a Lys
<220> FEATURE:
<221> NAME/KEY: Misc_feature
<222> LOCATION: (2)..(2)
<223> OTHER INFORMATION: Xaa is a Thr
<220> FEATURE:
<221> NAME/KEY: Misc_feature
<222> LOCATION: (3)..(3)
<223> OTHER INFORMATION: Xaa is a Lys
<220> FEATURE:
<221> NAME/KEY: Misc_feature
<222> LOCATION: (4)..(4)
<223> OTHER INFORMATION: Xaa is a Lys
<220> FEATURE:
<221> NAME/KEY: Misc_feature
<222> LOCATION: (5)..(5)
<223> OTHER INFORMATION: Xaa is a Thr
<220> FEATURE:
<221> NAME/KEY: Misc_feature
<222> LOCATION: (6)..(6)
<223> OTHER INFORMATION: Xaa is a Leu
<220> FEATURE:
<221> NAME/KEY: Misc_feature
<222> LOCATION: (7)..(7)
<223> OTHER INFORMATION: Xaa is a Arg
<220> FEATURE:
<221> NAME/KEY: Misc_feature
<222> LOCATION: (8)..(8)
<223> OTHER INFORMATION: Xaa is a Thr
<220> FEATURE:
<221> NAME/KEY: Misc_feature
<222> LOCATION: (9)..(9)
<223> OTHER INFORMATION: Xaa is an empty residue, histidine (His),
      acylated histidine (acyHis), arginine (Arg), acylated arginine
      (acyArg), lysine (Lys), or acylated lysine (acyLys)
<220> FEATURE:
<221> NAME/KEY: Misc_feature
<222> LOCATION: (10)..(10)
<223> OTHER INFORMATION: Xaa is glycine (Gly), a nonproteinogenic amino
      acid, or an empty residue
<220> FEATURE:
<221> NAME/KEY: Misc_feature
<222> LOCATION: (12)..(12)
<223> OTHER INFORMATION: Xaa is arginine (Arg), histidine (His), and
      lysine (Lys), or a nonproteinogenic amino acid and an empty
      residue
<220> FEATURE:
<221> NAME/KEY: Misc_feature
<222> LOCATION: (13)..(13)
<223> OTHER INFORMATION: Xaa is phenylalanine (Phe), leucine (Leu),
      tyrosine (Tyr), a nonproteinogenic amino acid or an empty residue

```
<220> FEATURE:
<221> NAME/KEY: Misc_feature
<222> LOCATION: (15)..(15)
<223> OTHER INFORMATION: Xaa is  serine (Ser), threonine (Thr), tyrosine
      (Tyr), a nonproteinogenic amino acid, or an empty residue
<220> FEATURE:
<221> NAME/KEY: Misc_feature
<222> LOCATION: (17)..(17)
<223> OTHER INFORMATION: Xaa is a serine (Ser), threonine (Thr),
      tyrosine (Tyr), glutamine (Gln), asparagine (Asn), a
      nonproteinogenic amino acid, or an empty residue
<220> FEATURE:
<221> NAME/KEY: Misc_feature
<222> LOCATION: (18)..(18)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (19)..(19)
<223> OTHER INFORMATION: Xaa is a  glutamine (Gln), asparagine (Asn),
      Asp, Glu, a nonproteinogenic amino acid, or an empty residue;
<220> FEATURE:
<221> NAME/KEY: Misc_feature
<222> LOCATION: (20)..(20)
<223> OTHER INFORMATION: Xaa is a  histidine (His), arginine (Arg),
      lysine (Lys), glutamine (Gln), asparagine (Asn), a
      nonproteinogenic amino acid, or an empty residue
<220> FEATURE:
<221> NAME/KEY: Misc_feature
<222> LOCATION: (21)..(21)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (22)..(22)
<223> OTHER INFORMATION: Xaa is a valine (Val), alanine (Ala), glycine
      (Gly), isoleucine (Ile), leucine (Leu), serine (Ser), threonine
      (Thr), tyrosine (Tyr), a nonproteinogenic amino acid, or an empty
      residue
<220> FEATURE:
<221> NAME/KEY: Misc_feature
<222> LOCATION: (23)..(23)
<223> OTHER INFORMATION: Xaa is a histidine (His), arginine (Arg),
      lysine (Lys), a nonproteinogenic amino acid, or an empty residue
<220> FEATURE:
<221> NAME/KEY: Misc_feature
<222> LOCATION: (24)..(24)
<223> OTHER INFORMATION: Xaa is an empty residue, glutamine (Gln),
      asparagine (Asn), Asp, Glu, a nonproteinogenic amino acid, or an
      empty residue
<220> FEATURE:
<221> NAME/KEY: Misc_feature
<222> LOCATION: (25)..(25)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (26)..(26)
<223> OTHER INFORMATION: Xaa is a tryptophan (Trp), phenylalanine (Phe),
      serine (Ser), threonine (Thr), tyrosine (Tyr), a nonproteinogenic
      amino acid, or an empty residue
<220> FEATURE:
<221> NAME/KEY: Misc_feature
<222> LOCATION: (27)..(27)
<223> OTHER INFORMATION: Xaa is a glutamine (Gln), glutamic acid (Glu),
      aspartic acid (Asp), asparagine (Asn), a nonproteinogenic amino
      acid, or an empty residue
<220> FEATURE:
<221> NAME/KEY: Misc_feature
<222> LOCATION: (28)..(28)
<223> OTHER INFORMATION: Xaa is a tryptophan (Trp), phenylalanine (Phe),
      valine (Val), alanine (Ala), glycine (Gly), isoleucine (Ile),
      leucine (Leu), a nonproteinogenic amino acid, or an empty residue
<220> FEATURE:
<221> NAME/KEY: Misc_feature
<222> LOCATION: (29)..(29)
```

-continued

```
<223> OTHER INFORMATION: Xaa is a serine (Ser), threonine (Thr), and
      tyrosine (Tyr); methionine (Met), tryptophan (Trp), phenylalanine
      (Phe), a nonproteinogenic amino acid, or an empty residue.

<400> SEQUENCE: 235

Xaa Xaa Xaa Xaa Xaa Xaa Xaa Xaa Xaa Xaa Cys Xaa Xaa Gly Xaa Cys
1               5                   10                  15

Xaa Xaa Xaa Xaa Xaa Xaa Xaa Xaa Xaa Xaa Xaa Xaa Xaa
            20                  25

<210> SEQ ID NO 236
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: Xaa is an empty residue, histidine (His),
      acylated histidine (acyHis), arginine (Arg), acylated arginine
      (acyArg), lysine (Lys), or acylated lysine (acyLys)
<220> FEATURE:
<221> NAME/KEY: Misc_feature
<222> LOCATION: (2)..(2)
<223> OTHER INFORMATION: Xaa is glycine (Gly), a nonproteinogenic amino
      acid, or an empty residue
<220> FEATURE:
<221> NAME/KEY: Misc_feature
<222> LOCATION: (4)..(4)
<223> OTHER INFORMATION: Xaa is arginine (Arg), histidine (His), and
      lysine (Lys), or a nonproteinogenic amino acid and an empty
      residue
<220> FEATURE:
<221> NAME/KEY: Misc_feature
<222> LOCATION: (5)..(5)
<223> OTHER INFORMATION: Xaa is phenylalanine (Phe), leucine (Leu),
      tyrosine (Tyr), a nonproteinogenic amino acid or an empty residue
<220> FEATURE:
<221> NAME/KEY: Misc_feature
<222> LOCATION: (7)..(7)
<223> OTHER INFORMATION: Xaa is  serine (Ser), threonine (Thr), tyrosine
      (Tyr), a nonproteinogenic amino acid, or an empty residue
<220> FEATURE:
<221> NAME/KEY: Misc_feature
<222> LOCATION: (9)..(9)
<223> OTHER INFORMATION: Xaa is a serine (Ser), threonine (Thr),
      tyrosine (Tyr), glutamine (Gln), asparagine (Asn), a
      nonproteinogenic amino acid, or an empty residue
<220> FEATURE:
<221> NAME/KEY: Misc_feature
<222> LOCATION: (10)..(10)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (11)..(11)
<223> OTHER INFORMATION: Xaa is a  glutamine (Gln), asparagine (Asn),
      Asp, Glu, a nonproteinogenic amino acid, or an empty residue;
<220> FEATURE:
<221> NAME/KEY: Misc_feature
<222> LOCATION: (12)..(12)
<223> OTHER INFORMATION: Xaa is a  histidine (His), arginine (Arg),
      lysine (Lys), glutamine (Gln), asparagine (Asn), a
      nonproteinogenic amino acid, or an empty residue;
<220> FEATURE:
<221> NAME/KEY: Misc_feature
<222> LOCATION: (13)..(13)
<223> OTHER INFORMATION: Xaa is a valine (Val), alanine (Ala), glycine
      (Gly), isoleucine (Ile), leucine (Leu), a nonproteinogenic amino
      acid, or an empty residue
<220> FEATURE:
<221> NAME/KEY: Misc_feature
<222> LOCATION: (14)..(14)
<223> OTHER INFORMATION: Xaa is a valine (Val), alanine (Ala), glycine
```

```
         (Gly), isoleucine (Ile), leucine (Leu), serine (Ser), threonine
         (Thr), tyrosine (Tyr), a nonproteinogenic amino acid, or an empty
         residue
<220> FEATURE:
<221> NAME/KEY: Misc_feature
<222> LOCATION: (15)..(15)
<223> OTHER INFORMATION: Xaa is a histidine (His), arginine (Arg),
         lysine (Lys), a nonproteinogenic amino acid, or an empty residue
<220> FEATURE:
<221> NAME/KEY: Misc_feature
<222> LOCATION: (16)..(16)
<223> OTHER INFORMATION: Xaa is an empty residue, glutamine (Gln),
         asparagine (Asn), Asp, Glu, a nonproteinogenic amino acid, or an
         empty residue
<220> FEATURE:
<221> NAME/KEY: Misc_feature
<222> LOCATION: (17)..(17)
<223> OTHER INFORMATION: Xaa is a valine (Val), alanine (Ala), glycine
         (Gly), isoleucine (Ile), leucine (Leu), a nonproteinogenic amino
         acid, or an empty residue;
<220> FEATURE:
<221> NAME/KEY: Misc_feature
<222> LOCATION: (18)..(18)
<223> OTHER INFORMATION: Xaa is a tryptophan (Trp), phenylalanine (Phe),
         serine (Ser), threonine (Thr), tyrosine (Tyr), a nonproteinogenic
         amino acid, or an empty residue
<220> FEATURE:
<221> NAME/KEY: Misc_feature
<222> LOCATION: (19)..(19)
<223> OTHER INFORMATION: Xaa is a glutamine (Gln), glutamic acid (Glu),
         aspartic acid (Asp), asparagine (Asn), a nonproteinogenic amino
         acid, or an empty residue
<220> FEATURE:
<221> NAME/KEY: Misc_feature
<222> LOCATION: (20)..(20)
<223> OTHER INFORMATION: Xaa is a tryptophan (Trp), phenylalanine (Phe),
         valine (Val), alanine (Ala), glycine (Gly), isoleucine (Ile),
         leucine (Leu), a nonproteinogenic amino acid, or an empty residue
<220> FEATURE:
<221> NAME/KEY: Misc_feature
<222> LOCATION: (21)..(21)
<223> OTHER INFORMATION: Xaa is a serine (Ser), threonine (Thr), and
         tyrosine (Tyr); methionine (Met), tryptophan (Trp), phenylalanine
         (Phe), a nonproteinogenic amino acid, or an empty residue.

<400> SEQUENCE: 236

Xaa Xaa Cys Xaa Xaa Gly Xaa Cys Xaa Xaa Xaa Xaa Xaa Xaa Xaa Xaa
1               5                   10                  15

Xaa Xaa Xaa Xaa Xaa
            20

<210> SEQ ID NO 237
<211> LENGTH: 6
<212> TYPE: PRT
<213> ORGANISM: Artificial Sequence
<220> FEATURE:
<223> OTHER INFORMATION: Synthetic sequence

<400> SEQUENCE: 237

Ser Ser Pro His Ser Tyr
1               5

<210> SEQ ID NO 238
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 238

Ile Ser Pro Gln Gly Tyr
1               5
```

<210> SEQ ID NO 239
<211> LENGTH: 20
<212> TYPE: PRT
<213> ORGANISM: Artificial Sequence
<220> FEATURE:
<223> OTHER INFORMATION: Synthetic sequence

<400> SEQUENCE: 239

Ala Ser Pro Ala Ala Pro Ala Pro Ala Ser Pro Ala Ala Pro Ala Pro
1               5                   10                  15

Ser Ala Pro Ala
            20

<210> SEQ ID NO 240
<211> LENGTH: 20
<212> TYPE: PRT
<213> ORGANISM: Artificial Sequence
<220> FEATURE:
<223> OTHER INFORMATION: Synthetic sequence

<400> SEQUENCE: 240

Ala Ala Pro Ala Ser Pro Ala Pro Ala Ala Pro Ser Ala Pro Ala Pro
1               5                   10                  15

Ala Ala Pro Ser
            20

<210> SEQ ID NO 241
<211> LENGTH: 20
<212> TYPE: PRT
<213> ORGANISM: Artificial Sequence
<220> FEATURE:
<223> OTHER INFORMATION: Synthetic sequence

<400> SEQUENCE: 241

Ala Ser Ala Ala Ala Pro Ala Ala Ala Ser Ala Ala Ala Ser Ala Pro
1               5                   10                  15

Ser Ala Ala Ala
            20

<210> SEQ ID NO 242
<211> LENGTH: 1
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: This amino acid residue may be repeated

<400> SEQUENCE: 242

Gly
1

<210> SEQ ID NO 243
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(5)
<223> OTHER INFORMATION: This stretch of amino acid residues may be
      repeated

<400> SEQUENCE: 243

```
Gly Gly Gly Gly Ser
1               5

<210> SEQ ID NO 244
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (2)..(6)
<223> OTHER INFORMATION: This stretch of amino acid residues may be
      repeated

<400> SEQUENCE: 244

Ser Gly Gly Gly Gly Ser
1               5

<210> SEQ ID NO 245
<211> LENGTH: 11
<212> TYPE: PRT
<213> ORGANISM: Artificial Sequence
<220> FEATURE:
<223> OTHER INFORMATION: Synthetic sequence

<400> SEQUENCE: 245

Asp Ile Cys Leu Pro Arg Trp Gly Cys Leu Trp
1               5                   10

<210> SEQ ID NO 246
<211> LENGTH: 29
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_Feature
<222> LOCATION: (1)..(1)
<223> OTHER INFORMATION: Xaa is an empty residue, acylated histidine
      (acy-His), acylated arginine (acy-Arg), acylated lysine (acy-Lys),
      acylated serine (acy-Ser), acylated threonine (acy-Thr), acylated
      tyrosine (acy-Tyr), acylated aspartic acid (acy-Asp), or acylated
      glutamic
<220> FEATURE:
<221> NAME/KEY: Misc_Feature
<222> LOCATION: (2)..(2)
<223> OTHER INFORMATION: Xaa is Val, Ala, Gly, Ile, Cys, or Leu
<220> FEATURE:
<221> NAME/KEY: Misc_Feature
<222> LOCATION: (3)..(3)
<223> OTHER INFORMATION: Xaa is, Gln, Glu, Asp, Cys, or Asn
<220> FEATURE:
<221> NAME/KEY: Misc_Feature
<222> LOCATION: (4)..(4)
<223> OTHER INFORMATION: Xaa is His, Arg, Lys, Gln, Cys, or Asp
<220> FEATURE:
<221> NAME/KEY: Misc_Feature
<222> LOCATION: (5)..(5)
<223> OTHER INFORMATION: Xaa is Val, Ala, Gly, Ile, Cys, or Leu
<220> FEATURE:
<221> NAME/KEY: Misc_Feature
<222> LOCATION: (6)..(6)
<223> OTHER INFORMATION: Xaa is Val, Ala, Gly, Ile, Leu, Ser, Th, Cys,
      or Tyr
<220> FEATURE:
<221> NAME/KEY: Misc_Feature
<222> LOCATION: (7)..(7)
<223> OTHER INFORMATION: Xaa is His, Arg, Cys, or Lys
<220> FEATURE:
<221> NAME/KEY: Misc_Feature
<222> LOCATION: (8)..(8)
<223> OTHER INFORMATION: Xaa is Gln, and Asn, His, Arg, Cys, or Lys
```

-continued

```
<220> FEATURE:
<221> NAME/KEY: Misc_Feature
<222> LOCATION: (9)..(9)
<223> OTHER INFORMATION: Xaa is Val, Ala, Gly, Ile, Cys, or Leu
<220> FEATURE:
<221> NAME/KEY: Misc_Feature
<222> LOCATION: (10)..(10)
<223> OTHER INFORMATION: Xaa is Trp, Phe, Ser, Thr, Cys, or Tyr
<220> FEATURE:
<221> NAME/KEY: Misc_Feature
<222> LOCATION: (11)..(11)
<223> OTHER INFORMATION: Xaa is Gln, Glu, Asp, Cys, or Asn
<220> FEATURE:
<221> NAME/KEY: Misc_Feature
<222> LOCATION: (12)..(12)
<223> OTHER INFORMATION: Xaa is Trp, Phe, Val, Ala, Gly, Ile, Cys, or
     Leu
<220> FEATURE:
<221> NAME/KEY: Misc_Feature
<222> LOCATION: (13)..(13)
<223> OTHER INFORMATION: Xaa is Ser, Thr, and Tyr; Met, Trp, Cys, or Phe
<220> FEATURE:
<221> NAME/KEY: Misc_Feature
<222> LOCATION: (14)..(14)
<223> OTHER INFORMATION: Xaa is Gln, Glu, Asp, Asn, Val, Ala, Gly, Ile,
     Cys, or Leu
<220> FEATURE:
<221> NAME/KEY: Misc_Feature
<222> LOCATION: (15)..(15)
<223> OTHER INFORMATION: Xaa is His, Arg, Lys, Val, Ala, Gly, Ile, Leu,
     Cys, or Pro
<220> FEATURE:
<221> NAME/KEY: Misc_Feature
<222> LOCATION: (16)..(16)
<223> OTHER INFORMATION: Xaa is Gln, Glu, Asp, Asn, Val, Ala, Gly, Ile,
     Cys, or Leu
<220> FEATURE:
<221> NAME/KEY: Misc_Feature
<222> LOCATION: (17)..(17)
<223> OTHER INFORMATION: Xaa is Val, Ala, Gly, Ile, Cys, or Leu
<220> FEATURE:
<221> NAME/KEY: Misc_Feature
<222> LOCATION: (18)..(18)
<223> OTHER INFORMATION: Xaa is Ser, Thr, Cys, or Tyr
<220> FEATURE:
<221> NAME/KEY: Misc_Feature
<222> LOCATION: (19)..(19)
<223> OTHER INFORMATION: Xaa is Val, Ala, Gly, Ile, Cys, or Leu
<220> FEATURE:
<221> NAME/KEY: Misc_Feature
<222> LOCATION: (20)..(20)
<223> OTHER INFORMATION: Xaa is Val, Ala, Gly, Ile, Leu, Cys, or Pro
<220> FEATURE:
<221> NAME/KEY: Misc_Feature
<222> LOCATION: (21)..(21)
<223> OTHER INFORMATION: Xaa is His, Arg, Lys, Val, Ala, Gly, Ile, Cys,
     or Leu
<220> FEATURE:
<221> NAME/KEY: Misc_Feature
<222> LOCATION: (22)..(22)
<223> OTHER INFORMATION: Xaa is Ser, Thr, Tyr, Gln, Glu, Asp, Cys, or
     Asn
<220> FEATURE:
<221> NAME/KEY: Misc_Feature
<222> LOCATION: (23)..(23)
<223> OTHER INFORMATION: Xaa is His, Arg, Lys, Val, Ala, Gly, Ile, Leu,
     Cys, or Pro
<220> FEATURE:
<221> NAME/KEY: Misc_Feature
<222> LOCATION: (24)..(24)
<223> OTHER INFORMATION: Xaa is Ser, Thr, Tyr, Val, Ala, Gly, Ile, Cys,
     or Leu
<220> FEATURE:
<221> NAME/KEY: Misc_Feature
<222> LOCATION: (25)..(25)
<223> OTHER INFORMATION: Xaa is Ser, Thr, Cys, or Tyr
<220> FEATURE:
<221> NAME/KEY: Misc_Feature
<222> LOCATION: (26)..(26)
```

```
<223> OTHER INFORMATION: Xaa is Val, Ala, Gly, Ile, Leu, Cys, or Pro
<220> FEATURE:
<221> NAME/KEY: Misc_Feature
<222> LOCATION: (27)..(27)
<223> OTHER INFORMATION: Xaa is Val, His, Arg, Lys, Gln, Glu, Asp, Cys,
      or Asn
<220> FEATURE:
<221> NAME/KEY: Misc_Feature
<222> LOCATION: (28)..(28)
<223> OTHER INFORMATION: Xaa is Val, Ala, Gly, Ile, Leu, Ser, Thr, Cys,
      or Tyr
<220> FEATURE:
<221> NAME/KEY: Misc_Feature
<222> LOCATION: (29)..(29)
<223> OTHER INFORMATION: Xaa isSer, Thr, Cys, or Tyr

<400> SEQUENCE: 246

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 247
<211> LENGTH: 6
<212> TYPE: PRT
<213> ORGANISM: Artificial Sequence
<220> FEATURE:
<223> OTHER INFORMATION: Synthetic sequence

<400> SEQUENCE: 247

Ala Glu Gly Pro Ser Thr
1               5
```

PEPTIDE ANALOGS

CROSS REFERENCE

This application claims benefit and is a Divisional of U.S. application Ser. No. 16/016,235, filed Jun. 22, 2018, which claims benefit of U.S. Provisional Patent Application No. 62/527,680, filed Jun. 30, 2017, which application is incorporated herein by reference in its entirety.

INCORPORATION BY REFERENCE OF SEQUENCE LISTING PROVIDED AS A TEXT FILE

A Sequence Listing is provided herewith in a text file, ADPT-003_SEQ_LISTING_20220216_ST25, created on Feb. 17, 2022, and having a size of 126,931 bytes. The contents of the text file are incorporated herein by reference in its entirety.

The present embodiments relate to superagonists and superantagonists of the adrenomedullin (ADM)/calcitonin gene-related peptide (CGRP)/intermedin (adrenomedullin 2, IMD) family of peptide hormones and therapeutic uses thereof. Also provided are multiple receptor ligands (MRLs) that regulate CLR/RAMP receptors, and a second G protein-coupled receptor (GPCR), including somatostatin receptors, neurotensin receptors, apelin receptor, bradykinin receptors, and type 1 angiotensin II receptor.

BACKGROUND

G protein-coupled receptors (GPCRs) are cell surface receptors and represent one of the largest protein families in the human genome. Based on phylogenetic criteria, the large superfamily of human GPCRs can be subdivided into the five main subfamilies: Glutamate, Rhodopsin, Adhesion, Frizzled/Taste and Secretin ('GRAFS' nomenclature), among which the Rhodopsin and Secretin families (resembling the class A and B GPCR family in the Kolakowski/NC-IUPHAR extended nomenclature system) are among the most studied subclass. More than one-third of all existing drugs target GPCRs.

The canonical view of GPCR signal transduction is focused on the activation of intracellular heterotrimeric guanine nucleotide binding proteins (G proteins)(Lagerstrom et al. (2008) Nat Rev Drug Discov; 7:339-357). The ability of a ligand to elicit a receptor-mediated cellular response is addressed by the term 'efficacy' (Kenakin (2013) Br J Pharmacol 168:554-575; Rajagopal (2013) Nat Rev Drug Discov 12:483). Historically, the efficacy of a ligand is derived from concentration-effect curves and quantified by the efficacy concentration (EC50) and maximum effect ($E_{max}$) relative to $E_{max}$ of a standard compound such as the endogenous ligands (Langmead and Christopoulos (2013) Br J Pharmacol 169:353-356).

Drugs that induce the maximum response in a system may nevertheless differ in efficacy, because the fraction of receptors required to be agonist-bound can depend on the individual efficacy for receptor activation. Therefore, the response usually has a certain assay-dependent limit. GPCR ligands are usually classified according to their efficacy, i.e. the ability to elicit a receptor-mediated pharmacological response (Smith et al. (2011) Mol Cell Endocrinol 331:241-247).

Crystallographic efforts with GPCRs in their active state show that both agonist binding and binding of a G protein are important to capture the protein in a fully active state (Rasmussen et al. (2011) Nature 477:549-555). Moreover, recent studies show that GPCR agonists stabilize only a subset of possible conformational states (Kobilka and Deupi (2007) Trends Pharmacol Sci 28:397-406; Kenakin (2013) Br J Pharmacol 168:554-575). Therefore, diverse agonists of a given receptor protein may stabilize different subsets of conformations with distinct efficacies for the activation of specific signaling pathways (Kenakin (2013) Br J Pharmacol 168:554-575). Therefore, a 'strong' agonist could populate a set of conformations similar to the more uniform and fully active conformation generated by a highly efficacious agonist.

Consequently, supraphysiological efficacy of compounds stabilizing a more uniform conformation than the endogenous agonist represents a superagonist (Schrage et al. (2015) Br J Pharmacol doi: 10.1111/bph.13278). In the largest and most 'druggable' class of GPCRs (the rhodopsin-like class or class A), a few synthetic compounds have been described to exhibit greater intrinsic efficacy than the endogenous ligands. These compounds include those for Somatostatin sst4 receptor, ghrelin receptor, α2A-adrenoceptor, thyrotropin-releasing hormone TRH1 receptor, and muscarinic M2 cholinoceptor (Schrage et al. (2015) Br J Pharmacol doi: 10.1111/bph.13278). There are examples (Carlier et al. (2002) Bioorg Med Chem Lett 12:1985-1988; Ihara et al. (2004) Biosci Biotechnol Biochem 68:761-763) for supraphysiological agonist efficacy at ligand-gated ion channels as well. Examples include the GABA receptors.

The ADM/CGRP/IMD peptide family includes calcitonin gene-related peptides (CGRPα and CGRPβ), adrenomedullin (ADM), intermedin/adrenomedullin 2 (IMD/ADM2), calcitonin (CT) and amylin. Among them, CGRPs, ADM and IMD are structurally similar and signal through receptor complexes consisting of two transmembrane components, the calcitonin receptor-like receptor (CLR) and one of the three receptor activity-modifying proteins (RAMP1, 2, and 3). Co-expression of the calcitonin receptor-like receptor (CLR) and receptor activity-modifying proteins (RAMPS) is required to generate functional receptors for CGRPs, ADM and IMD. Whereas CGRPs mainly act through the CLR/RAMP1 receptor, ADM has high affinity for CLR/RAMP2 and 3 receptors. On the other hand, IMD exhibits no distinct preference for the three CLR/RAMP receptors.

The 52-amino-acid ADM is produced in adrenal gland, lung, kidney, heart muscle and other organs; whereas CGRP peptides are neurotransmitters. The plasma levels of ADM, CGRPs, and IMD are in the picomolar range. Activation of the CLR/RAMP receptors leads to intracellular elevation of adenosine 3',5'-cyclic monophosphate (cAMP) in the receptor-bearing cells. CLR/RAMP receptors are present on different cell types in almost all organs including endothelial cells. These peptides are thought to be metabolized by neutral endopeptidase and are predominantly cleared by the kidney, or in the lung where CLR/RAMP receptors are highly expressed [Gibbons C, Dackor R, Dunworth W, Fritz-Six K, Caron K M, Mol Endocrinol 21(4), 783-796 (2007)].

Although ADM and IMD were first characterized as potent vasotone regulators, subsequent investigations have revealed that the functions of these peptides go far beyond the hemodynamic/hypotensive effects, and they exhibit pleiotropic effects in a variety of organs. Studies of transgenic mice have shown that ADM, CLR, and RAMP2 are essential for normal development of blood and lymphatic vasculatures during embryonic development and throughout adulthood. Infusion of ADM or IMD has been shown to reduce vasoconstriction, peripheral vascular resistance, and edema, and to increase cardiac output and renal glomerular filtration in animals. These peptides have also been shown to have beneficial effects on heart failure and myocardial infarction in humans, sheep, and rodents; pulmonary arterial hypertension in humans, pigs, and rats. Furthermore, it is generally accepted that ADM and IMD are counter-regulatory hormones that are increased in diseased state as a compensatory response to injury and hypoxia. In addition, ADM has been shown to ameliorate acute or chronic lung injuries induced by lipopolysaccharide (LPS), elastase, monocrotaline, bleomycin, ischemia-reperfusion, and carrageenan in a variety of animal models.

In addition, exogenous ADM and IMD have been shown to stimulate the proliferation and migration of endothelial and lymphendothelial cells in vitro as well as to revascularize damaged lymphatic and blood vessels in a variety of animal models. Furthermore, these hormones exhibit neuroprotective, renoprotective, diuresis and/or natriuresis effects in animals with heart failure, myocardial infarction, stroke, resistant hypertension, pulmonary arterial hypertension, preeclampsia, secondary lymphedema, and diabetic ulcer, by improving endothelial cell survival, angiogenesis and vascular integrity, cardiac output, and renal glomerular filtration. Moreover, ADM can mobilize and enhance the survival, differentiation, and the angiogenic potency of a variety of stem/progenitor cells.

CGRPs are sensory neuropeptides with potent vasodilatory, cardiotonic, and pain transmission action as described in U.S. Pat. No. 4,530,838 to Evans, et al. CGRP is present in both the central and peripheral nervous systems and is concentrated in those areas of the body receiving sensory input from the dorsal horn with limited amounts associated with autonomic input. In the brain, the peptide is present in the nuclei of sensory and motor cranial nerves and in cell bodies in the hypothalamus, preoptic area, ventromedial thalamus, hippocampus, and the like (Poyner, D. 1992, Pharmac. Ther. 56:23-51).

In addition, ADM/CGRP/IMD family peptides are known to have potent stimulatory effects on the proliferation of endothelial cells that serve as starter materials for blood vessels, angiogenesis, and vascular remodeling. Because ADM, CGRP, and IMD are among the most potent known vasodilators in humans, these peptides may be functionally important for maintaining high flow/low resistance circulation and feto-placental tissue development during normal physiology and pregnancy.

Agonists at the receptor level to CGRP, ADM, or IMD have been postulated to be useful in pathophysiologic conditions where endothelial dysfunction, insufficient vessel development, and aberrant vasodilation regulation has occurred. Pan-specific and receptor subtype-selective CLR/RAMP receptor superagonists could be of use as a tool for stimulating vascular CLR/RAMP receptors and thus stimulating tissue regeneration in pathological conditions such as heart failure, myocardial infarction, resistant hypertension, malignant hypertension, vasospasm, stroke, vasospasm, bronchopulmonary dysplasia, pulmonary arterial hypertension, lymphedema, wound healing, ulcerative colitis, acute lung injury, pressure ulcer, age-related macular degeneration, multiple sclerosis, Alzheimer's disease, Parkinson's disease, epilepsy, retinopathy, organ preservation, eclampsia, and preeclampsia. Pan-specific and receptor subtype-selective CLR/RAMP receptor super-antagonists could be of use as a tool for blocking angiogenesis and pain perception, and thus for the treatment of pathological conditions such as headache, migraine, tumor growth, angiogenesis and metastasis.

The physiological functions of the hormone peptides in the CT/CGRP family are determined by receptor-binding and receptor-activation specificity, and the tissue expression profiles of individual ligands and their respective receptors and have been shown to be involved in cardiovascular morphogenesis, hemodynamic regulation, sensory neurotransmission, inflammatory reactions, nociceptive behavior and glucose homeostasis (see, e.g., Hay, et al. (2001) Trends Pharmacol. Sci. 22:57-59; Shindo, et al. (2001) Circulation 104: 1964-1971; Zhang et al. 2001, Pain 89:265-273; Salmon et al. (1999) Neuroreport 10:849-854; Salmon, et al. (2001) Nat. Neurosci. 4:357-358; and Mulder, et al. (2000) Am. Physiol. 278:E684-E691).

Inhibitors at the receptor level to CGRP and ADM are postulated to be useful in pathophysiologic conditions where excessive CGRP and/or ADM receptor activation has occurred. Some of these include neurogenic vasodilation, neurogenic inflammation, migraine, cluster headache and other headaches, thermal injury, circulatory shock, menopausal flushing, and asthma. CGRP receptor activation has particularly been implicated in the pathogenesis of migraine headache (Edvinsson L. (2001) CNS Drugs 15(10):745-53; Williamson, D. J. (2001) Microsc. Res. Tech. 53: 167-178.; Grant, A. D. (2002) Brit. J Pharmacol. 135:356-362). Headache associated with migraines is thought to be a result of profound cerebral vasodilation associated with migraine events (Moskowitz (1992) Trends Pharmacol. Sci. 13:307-311). Migraine patients exhibit elevated basal CGRP levels compared to controls (Ashina, et al., (2000) Pain 86:133-8), and serum levels of CGRP are elevated during migraine (Goadsby, et al. (1990) Ann. Neurol. 28:183-7). Treatment with anti-migraine therapeutic candidates returns CGRP levels to normal coincident with alleviation of headache (Gallai, et al. (1995) Cephalalgia 15:384-90); whereas intravenous CGRP administration produces headache in migraineurs (Lassen, et al. (2002) Cephalalgia 22:54-61). Thus, CLR/RAMP1 subtype-selective receptor super-antagonists (or CGRP antagonists) could be useful for blocking cerebrovascular CGRP receptors and thus for the treatment of headache, migraine, neuropathic pain, and osteoarthritis pain.

Both small molecule and peptide antagonists of the CGRP receptor, such as intravenous olcegepant (BIBN4096 BS, Boehringer Ingelheim) and oral telcagepant (MK-0974, Merck & Co., Inc.) have been shown to be effective in clinical trials for the treatment of migraines. (See, Tepper and Stillman, (2008) Headache 48:1259-1268; and Durham and Vause (2010) CNS Drugs 24:539-548). However, select small molecule CGRP antagonist such as MK-3207 has been associated with asymptomatic liver test abnormalities in some patients.

Peptide antagonists of the CGRP receptor include peptides comprising the sequence of CGRP but lacking at least the first seven amino acids of the 37-amino-acid CGRP sequence (e.g., CGRP (8-37), CGRP (28-37), [Tyr$^o$]CGRP (28-37), CGRP (12-37), h-a-CGRP (9-37), h-a-CGRP (10-37), h-a-CGRP (11-37), [Ala 9]-h-a-CGRP (8-37), [Ala 10]-h-a-CGRP (8-37), [Ala n]-h-a-CGRP (8-37), [Ala 12]-h-a-CGRP (8-37), h-a-CGRP (19-37), h-a-CGRP (23-37) and acetyl-h-a-CGRP (19-37); Mimeault, M. et al., (1992) Med. Chem. 35:2163-2168; Rovero, P. et al. (1992) Peptides 13:1025-1027). While a number of CGRP receptor peptide antagonists have been shown to effectively compete with CGRP in vitro, these antagonists have not performed as well in in vivo models of migraine-like pathologies due to low bioactivities.

Inhibitors at the receptor level to ADM include ADM22-52. Tertiary structure analyses indicated that the binding domain of ADM family peptides is characterized by an unstructured string. Because (1) ADM acts as a mitogenic factor for tumor cells and surrounding vessels in tumors with a lung, breast, colon, brain, pancreas, endometrium, ovary, kidney, or prostate origin, (2) ADM expression in tumors is associated with the aggressiveness of tumors, distant metastasis and poor patient prognosis, and (3) blockage of CLR/RAMP receptor signaling reduces growth, microvessel density, tumor-associated macrophage-induced angiogenesis, and metastasis of tumor xenografts, CLR/RAMP2 and/or CLR/RAMP3 receptor antagonists are antiangiogenic drug candidates for cancer therapy.

Previous approaches to block CLR/RAMP receptor signaling include the use of (1) synthetic peptide antagonists (e.g., CGRP8-37 and ADM22-52, which are specific for CGRP-mediated CLR/RAMP1 and ADM-mediated CLR/RAMP2 signaling, respectively), (2) small molecule CGRP receptor antagonist (e.g., telcagepant), (3) anti-ligand antibodies (e.g., anti-CGRP or anti-ADM antibody), and (4) anti-receptor antibodies (e.g., anti-CLR or anti-RAMP antibody). However, existing therapeutic candidates are associated with efficacy or safety concerns. First, peptide antagonists such as CGRP8-37 and ADM22-52 have extremely short half-lives and low potencies, and are receptor-specific. Second, the small molecule CLR/RAMP1 receptor antagonists suffer liver toxicity in humans. Third, the anti-ligand and anti-receptor antibodies are specific for one of the ligands or receptor components; therefore, they only act on a small subgroup of targets. Fourth, the antibodies have low volume of distribution when compared to small molecules and peptides, and have limited access to CLR/RAMP receptors in the central nervous system.

The most widely studied CLR/RAMP receptor agonist, ADM, is known to be safe, effective and well tolerated in early clinical trials for the acute treatment of heart failure, ulcerative colitis, and pulmonary hypertension. However, due to limited potency of the agonist and the short half-life, pharmacological effect is inadequate.

Somatostatin was first identified as an inhibitor of the secretion of growth hormone secretion, and is known as somatotropin release-inhibiting factor (SRIF). Somatostatin is also a regulatory hormone of the gastrointestinal tract and is involved in the proliferation of both normal and tumorigenic cells. Somatostatin is produced by the δ-cells of the pancreas, paracrine cells in the gastrointestinal tract, and in the hypothalamus. Somatostatin-14 and -28 are produced from the somatostatin precursor, the 116-amino-acid pre-prosomatostatin. Somatostatin triggers numerous physiological processes by acting on five somatostatin receptor subtypes, SSTR1-5. The related neuropeptides cortistatin-17 and -29 are also endogenous ligands for the five SSTRs. For decades, somatostatin-related drugs have been of interest in the areas of endocrinology and oncology. Somatostatin was initially viewed as an attractive candidate for the treatment of cancer due to its ability to block hormone release after binding to its receptors. So far, somatostatin analogs have been used to treat gastrointestinal disorders such as bleeding peptic ulcers, ulcerative colitis, and gallbladder fistulae as well as acromegaly resulting from excessive production of growth hormone.

As somatostatin receptors are overexpressed in select types of tumors, somatostatin can also be used in cancer treatment. In addition to alleviating the symptoms of functional neuroendocrine tumors, activation of somatostatin receptors can inhibit the growth of neuroendocrine tumors. Clinical studies showed that somatostatins and peptidomimetics can halt tumor progression by both directly and indirectly controlling tumor growth. The direct antimitotic effect is mediated by somatostatin receptors on tumor cells. Indirect effects of somatostatins are mediated by the inhibition of growth factor secretion, inhibition of angiogenesis, and immunomodulatory effects on target tissues. By suppressing the synthesis and secretion of growth factors, such as insulin-like growth factor (IGF1), somatostatin analog such as octreotide exerts antiproliferative and antiangiogenesis effects and reduces tumor growth. Somatostatins may also exert antiangiogenic effects by inhibiting angiogenic growth factors (eg, platelet-derived growth factor, IGF-1, and epidermal growth factor) in endothelial and smooth muscle cell proliferation. Somatostatin analogs may also regulate inflammatory and immune mechanisms and enhance their antiproliferative activity. Accordingly, octreotide (SEQ ID NO: 215) and related analogs are used to treat and prevent perioperative carcinoid crisis, a life-threatening condition in patients with metastatic neuroendocrine tumors. Carcinoid crisis is characterized by a profound decrease in or elevation of blood pressure, tachycardia, elevated blood glucose, and severe bronchospasm. It has been shown that octreotide is effective in inhibiting carcinoid crisis in patients with metastatic functional neuroendocrine tumors, and that the 2012 NCCN guidelines on neuroendocrine tumors specifically state that octreotide therapy should be initiated in all patients before resection of primary or metastatic functional (carcinoid) endocrine tumors.

In addition, octreotide and related analog lanreotide have been shown to control symptoms in up to 50-80% of patients with metastatic carcinoid endocrine tumors and stabilize disease progression, and that long-acting somatostatins were effective in exerting antiproliferative activity. An agent that can activate somatostatin receptors and antagonize CLR/RAMP receptors could provide a further improvement in the treatment of patients with a variety of metastatic neuroendocrine tumors.

Neurotensin is a tridecapeptide (SEQ ID NO: 221) that induces antinociception and hypothermia. Neurotensin behaves as a neurotransmitter or neuromodulator in the CNS, and signal through two neurotensin receptors (NTR1 and NTR2). Most of the activity mediated by neurotensin (neurotensin 1-13) can be observed with the shorter fragment, neurotensin (8-13 (SEQ ID NO: 222)). Based on studies in animals, it has been postulated that neurotensin and its analogs can be used to provide pain relief, and to reduce core body temperature during situation that hypothermia is beneficial (e.g., during the treatment of stroke). Agents that can activate neurotensin receptor and CLR/RAMP receptors represent useful additive or synergistic vasoprotective and neuroprotective agents for the treatment of vascular injuries such as cerebral vessel damages. Agents that can activate neurotensin receptor but antagonize CLR/RAMP receptors can be useful for the treatment of neuropathic pains such as migraine, headache, and osteoarthritis pain.

Apelin is a peptide agonist for G protein-coupled APJ receptor (AGTRL1). Apelin gene encodes a pre-proprotein of 77 amino acids, and generates active fragments including, 36-amino-acid apelin 36 (SEQ ID NO: 227), 17-amino-acid apelin 17 (SEQ ID NO: 226) and 13-amino-acid apelin 13 (SEQ ID NO: 225). Apelin has potent effects on the contractility of heart and exert positive inotropic activities, diuretic effect, and direct myocardial protection from ischemia reperfusion injury (See Tatemoto et al. (2001) Regul Pept 99:87-92; Seyedabadi et al. (2002) Auton Neurosci 101:32-38; Szokodi et al. (2002) Circ Res 91:434-440; Katugampola et al. (2001) Br J Pharmacol 132:1255-60; Lee et al. (2000) J Neurochem 74:34-41; Shah (1996) Cardiovasc Res 31:847-67; De Falco et al. (2002) In Vivo 16:333-336). Apelin can also enhance vasodilation. Apelin appears to exert its effects at least in part by activating $Na_+/H_+$ exchanger or by activating $Na_+/Ca_{++}$ exchanger (Szokodi et al. (2002) Circ Res. 91:434-440; Tatemoto et al. (2001) Regul Pept, 99:87-92; Lee et al. (2000) J Neurochem. 74:34-41). Apelin circulates as pyroglutamylated apelin-13 (SEQ ID NO: 225). Agents that can activate apelin receptor and CLR/RAMP receptors represent useful additive or synergistic vasoprotective and cardioprotective agents for the treatment of a variety of cardiovascular disease that may benefit from improved heart contractility and/or vasodilation.

Bradykinin or kinin-9 is a vasoactive 9-amino-acid peptide (SEQ ID NO: 230) that is formed locally in body fluids and tissues from the plasma precursor kininogen during inflammatory processes. It is a potent agent of arteriolar dilation and increased capillary permeability. Bradykinin is a powerful blood-vessel dilator, increasing vascular permeability and causing a fall in blood pressure, as well as an edema-producing agent. Bradykinin is also released from mast cells during asthma attacks, from gut walls as a gastrointestinal vasodilator. Bradykinin is also one of the most potent peripheral pain mediators. A number of bradykinin effects have been shown to be mediated by products of the arachidonic acid-cyclooxygenase cascade. In various models of persistent inflammation, bradykinin has been shown to play important role in the maintenance of hyperalgesia with or without concomitant activation. The carrageenan-induced mechanical hyperalgesia was diminished by bradykinin receptor antagonists. Bradykinin receptor antagonism also reduced carrageenan-induced edema (see Pethö and Reeh, (2012) Physiological Reviews 92:1699-1775; R. M. Burch, et al., (1990) Med. Res. Rev., 10:237-269; Clark, W. G. (1979) Handbook of Experimental Pharmacology, Vol. XXV: Bradykinin, Kallidin, and Kallikrein. Erdo, E.G. (Ed.), 311-322). As a pain mediator from damaged tissues, bradykinin signals by activating (i) phospholipase A2 and (ii) phospholipase C pathways (See e.g., Oxford Dictionary of Biochemistry and Molecular Biology, Oxford University Press (2001)). Bradykinin antagonists were shown to ameliorate pain and hyperalgesia in mammals including humans. (See, Costello, A. H. et al., (1989) European Journal of Pharmacology, 171:259-263 and Steranka, et al., (1987) Neurobiology, 85:3245-3249). These observations thus suggested that bradykinin receptor antagonists could be of use as protector of vascular permeability and as analgesics for the treatment of bone and joint pain (osteoarthritis), repetitive motion pain, dental pain, pain associated with cancer, myofascial pain (muscular injury, fibromyalgia), perioperative pain (general surgery, gynecological), inflammatory pain such as inflammatory airways disease (chronic obstructive pulmonary disease), and chronic pain such as migraine headache.

Bradykinin receptor antagonists have been studied extensively for the treatment of pain and aberrant vascular permeability such as that found in hereditary angioedema (HAE) patients. HAE is a rare genetic disorder, characterized by recurrent and unpredictable episodes of angioedema including in the gastrointestinal tract, such as abdominal attack; skin, such as peripheral, facial, and genital attack; as well as the upper airways such as laryngeal attack. In HAE, deficiency of C1-esterase inhibitor (C1-INH; a key regulator of the kallikrein-kinin plasma cascade system and classical complement pathway) leads to an over production of the bradykinin. There are two pharmacotherapeutic approaches to treat acute HAE attack. One is the C1-INH replacement therapy. The other is to inhibit bradykinin either by blocking the enzyme kallikrein or preventing the binding of bradykinin with the receptor. Clinically, bradykinin receptor antagonist such as icatibant has been successfully used to reduce vasodilatation, vascular permeability and angioedema in HAE patients (Craig et al., (2014) Int Arch Allergy Immunol; 165:119-127). An agent providing a bradykinin receptor antagonist and a CLR/RAMP receptor agonist could be of greater use for the treatment of HAE when compared to a bradykinin receptor antagonist alone. In addition, such an agent provides drug candidates for protecting blood-brain barrier and vascular integrity in patients with impaired blood-brain barrier such as those with multiple sclerosis, Alzheimer's disease, cerebral edema, or epilepsy as well as for the treatment of asthma, inflammatory bowel disease, wound healing, ulcerative colitis, rheumatoid arthritis and edema resulting from trauma associated with burns, sprains or fracture.

An agent that provides bradykinin receptor antagonist and a CLR/RAMP receptor antagonist could be of usage in the treatment or prevention of pain including, for example, bone and joint pain (osteoarthritis), repetitive motion pain, dental pain, pain associated with cancer, myofascial pain (muscular injury, fibromyalgia), perioperative pain (general surgery, gynecological), inflammatory pain such as inflammatory airways disease (chronic obstructive pulmonary disease), and chronic pain such as migraine headache. These compounds may also be used subsequent to surgical intervention (e.g. as post-operative analgesics) and to treat inflammatory pain of varied origins (e.g. osteoarthritis, rheumatoid arthritis, rheumatic disease, tenosynovitis, wounds and gout), as well as for the treatment of pain associated with angina, menstruation, or cancer.

Angiotensin II is an 8-amino-acid hormone (SEQ ID NO: 232) that causes vessel constriction, leading to high blood pressure and strain on the heart. Angiotensin II receptor signaling blockers are used to prevent angiotensin II from binding to the type 1 angiotensin II receptor (or AT1 receptor) in vessels, thereby resulting in lower blood pressure. Therefore, blockers of AT1 receptor signaling such as renin inhibitors, angiotensin converting enzyme [ACE] inhibitors, and angiotensin II receptor antagonists [ARBs] have been widely used as antihypertensives and to prevent cardiovascular diseases such as congestive heart failure, among other indications in the last three decades. Importantly, evidence suggests that reduction of the blood pressure by 5 mmHg with these antihypertensive drugs can decrease the risk of stroke by 34%, of ischemic heart diseases by 21%, and reduce the likelihood of dementia, heart failure, and mortality from cardiovascular disease. Despite these advances, physicians are having difficulties to achieve controlled blood pressure in patients with resistant hypertension (RHTN). In fact, there is scant evidence for beneficial outcomes using additional drug treatment after three antihypertensives have failed to achieve target blood pressure in RHTN patients. The situation could be related to the fact that most of the existing antihypertensive drugs mainly target the (1) renin-angiotensin-aldosterone axis, (2) the sympathetic nervous activities, and (3) the endothelin signaling pathway, and act by blocking these signaling pathways.

In addition, angiotensin II signaling has been implicated in the pathogenesis of pulmonary injury in neonates. AT1 receptor antagonist was shown to attenuate lung fibrosis in hyperoxia-exposed newborn rats (Chou et al., (2012) J Pharmacol Exp Ther. 340:169-175). Because the nature of vascular diseases is generally multifactorial; therefore, the simultaneous manipulation of the angiotensin II signaling system and CLR/RAMP receptors in circulation or in localized tissues by an agent that is capable of blocking the angiotensin II signaling and activating the CLR/RAMP receptor signaling could hold great therapeutic potential for the treatment of RHTN and neonatal lung injury when compared to angiotensin II blocker alone or CLR/RAMP receptor agonist alone.

Publications, each of which are herein specifically incorporated by reference, include:
Hong et al. (2012) Br J Pharmacol 166:110-120
Watkins et al. (2013) Br J Pharmacol 170:1308-1322
Booe et al. (2015) Mol Cell 58:1040-1052
Hinson et al. (2000) Endocr Rev 21:138-167 (2000)
Takei et al. (2004) FEBS Lett 556:53-58.
McLatchie et al. (1998). Nature 393: 333-339
Bell, D. & McDermott, B. J. (2008) Br J Pharmacol 153 Suppl 1, S247-262
Muff, R. et al. (1998). FEBS Lett 441, 366-368
Hay et al. (2005) Mol Pharmacol 67:1655-1665
Robinson et al. (2009) J Pharmacol Exp Ther 331:513-521
Yin et al. (2009) J Biol Chem 284:12328-12338
van Der Lee et al. (2008) J Biomol Screen 13:986-998

SUMMARY OF THE INVENTION

Compositions and methods are provided for adrenomedullin and intermedin/adrenomedullin 2 analogs that exhibit superagonistic or superantagonist activity on CLR/RAMP receptors (i.e., CLR/RAMP1, 2, and 3). It is shown herein that analogs of adrenomedullin and intermedin analogs that contain N-terminal acylation with or without a polyethylene glycol (PEG) moiety exhibit superior agonistic receptor-activation activities toward CLR/RAMP1, CLR/RAMP2, and/or CLR/RAMP3 receptor in term of EC50 when compared to adrenomedullin, CGRP, or intermedin. Such analogs may be referred to herein as pan-specific superagonists.

In some embodiments of the invention, adrenomedullin analogs are provided that contain N-terminal acylation with or without PEG moieties, which analogs exhibit superagonistic activity toward CLR/RAMP2 and/or CLR/RAMP3 receptor, when compared to wild type ligands. Such analogs may be referred to herein as CLR/RAMP2-receptor selective superagonists.

In other embodiments, antagonistic analogs comprising sequences of adrenomedullin, CGRPs and intermedin with N-terminal acylation, with or without PEG moieties, are provided, which exhibit superior antagonistic activities toward CLR/RAMP1, CLR/RAMP2, and/or CLR/RAMP3 receptors in term of IC50 when compared to known CLR/RAMP receptor antagonist. Such analogs may be referred to herein as pan-specific, CLR/RAMP1-selective, or CLR/RAMP2-selective superantagonists.

It has been surprisingly found that certain modifications in the N-terminal portion of the ADM, CGRPs, intermedin, or their analogs as disclosed and described herein, are responsible for the specificity and potency of peptide agonist activity toward CLR/RAMP1, 2, and/or 3. It is shown herein that modification in the N-terminal portion of the ADM, CGRPs, and IMD analogs can tune the activity from a normal agonist or antagonist to a superagonist or superantagonist of CLR/RAMP receptors. Additional substitutions or modifications can provide additional desirable characteristics to the peptides of the present invention.

In some embodiments a specific improvement is provided, where a CLR/RAMP1 receptor super-antagonist, as described herein, comprises an amino terminal modification $R_1$ where $R_1$ is a functional group comprising a structure of Formula (W')(X')n(Y')n'(Z')n'', wherein W' is a fatty acid, a fatty diacid, a fatty acid derivative or empty; X' is a PEG group, glutamic acid, γ-glutamic acid, a proteinogenic or non-proteinogenic amino acid, Lys or empty; Y' is a PEG group, glutamic acid, γ-glutamic acid, a proteinogenic or non-proteinogenic amino acid, Lys, or empty; Z' is a proteinogenic amino acid, a non-proteinogenic amino acid, Lys, or empty; and each of n, n' and n'' is an independently selected integer from 1 to 20. $R_1$ can be located on any side chain group of an amino acid in the peptide.

In other embodiments multiple receptor ligands (MRLs) are provided, which comprise or consist of (i) a CLR/RAMP receptor ligand and (ii) a ligand of a second GPCR, which may be selected from, without limitation, somatostatin receptors, neurotensin receptors, apelin receptor, bradylinin receptors and type 1 angiotensin II receptor. An MRL may comprise chimeric sequences of a CLR/RAMP receptor ligand, e.g. a pan-specific superagonist, a CLR/RAMP2-receptor selective superagonist, a pan-specific super-antagonist, a CLR/RAMP1-selective super-antagonist, or a CLR/RAMP2-selective superantagonist as described herein; and a ligand for a second GPCR.

Conjugation of a ligand for a second GPCR in an MRL with the CLR/RAMP receptor superagonists or superantagonists generates agents that are capable of modulating not only CLR/RAMP receptors but also the second GPCR. This observation is surprising, as previous modifications with other GPCR ligands such as GnRH, kisspeptin, enkephalin, dynorphin and endomorphin, either lead to the decimation of CLR/RAMP receptor-regulatory activity and/or the inactivation of the second GPCR ligand in the chimera peptides. Likewise, simple chimeras that consist of two ligands without a linker sequence are devoid of potent multiple receptor-regulatory activities. In addition, MRLs can provide first-ligand receptor-tissue-specific targeting of the second ligand in vivo, and vice versa. This capability is beneficial to prevent unwanted side effects of nonspecific distribution of the first and the second ligands when administered alone or in combination. MRLs described herein are novel agents for the treatment of a variety of cardiovascular, pulmonary, cutaneous, renal, endocrine, and neuronal diseases that are associated with defective signaling in somatostatin receptors, neurotensin receptors, apelin receptor, bradylinin receptors, type 1 angiotensin II receptor, and/or CLR/RAMP receptors.

One embodiment provides sequence modification(s) of MRLs, site specific sequence variations, and spatial or steric interference considerations such that the desired structure-activity relationship relative to CLR/RAMP receptor and a second GPCR is retained.

Also provided are pharmaceutical compositions that comprise a therapeutically effective amount of the CLR/RAMP receptor superagonists, CLR/RAMP receptor super-antagonists, or MRLs. Methods are provided for treating a disease or disorder associated with signaling of CLR/RAMP receptors, somatostatin receptors, neurotensin receptors, apelin receptor, bradykinin receptors, and type 1 angiotensin II receptor, in a subject, by administering a therapeutically effective amount of the agonists, antagonists, or MRLs.

Without being limited by the mechanism of action, the activity exhibited by any of the analog polypeptides described herein may in part be explained by the formation of stable ligand-receptor complex when compared to wild type ligands.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE EMBODIMENTS

The following definitions are set forth to illustrate and define the meaning and scope of the various terms used to describe the embodiments.

The amino acid sequences of the present invention contain the conventional one letter and three letter codes for naturally occurring amino acids, as well as generally accepted three letter codes for other amino acids, such as Aib (a-aminoisobutyric acid), Orn (ornithin), Dab (2,4-diamino butyric acid), Dap (2,3-diamino propionic acid), Nle (nor-leucine), GABA (γ-aminobutyric acid) or Ahx (ε-amino-hexanoic acid). For the avoidance of doubt, in the definitions provided herein, it is generally intended that the peptidic compounds of the present invention comprise a linear backbone of amino carboxylic acids linked by peptide, i.e. carboxamide bonds. All amino acid residues in peptides of the invention are preferably of the L-configuration. However, D-configuration amino acids may also be present.

The following are abbreviations that are at times used in this specification: EC50=negative logarithm base 10 of the agonist concentration required to produce half maximum effect; SEM=standard error of the mean; MW=molecular weight; cAMP=adenosine 3',5'-cyclic monophosphate; cDNA=complementary DNA; kb=kilobase (1000 base pairs); kDa=kilodalton; ATP=adenosine 5'-triphosphate; nt=nucleotide; bp=base pair; nm=nanomolar.

As used herein, "agonist" refers to a biologically active ligand that binds to its complementary biologically active receptor and activates the latter either to cause a biological response in the receptor or to enhance preexisting biological activity of the receptor. An antagonist refers to a biologically active ligand that binds to a biologically active receptor and decreases the response. As used herein, "antagonist" refers to a biologically active ligand which inhibits the physiological response of the receptor.

As used herein, a superagonist is an agonist that has a greater biological activity than the native ligand, including without limitation the wild-type human intermedin/adrenomedullin 2, adrenomedullin or calcitonin gene-related peptides (CGRPs). Reference may be made to the activity of a specific ligand/receptor pair, for example the calcitonin receptor-like receptor (CLR) and one of the three receptor activity-modifying proteins (RAMP1, 2, and 3). Co-expression of the calcitonin receptor-like receptor (CLR) and receptor activity-modifying proteins (RAMPs) is required to generate functional receptors for CGRPs, ADM and IMD. Whereas CGRPs mainly act through the CLR/RAMP1 receptor, ADM has high affinity for CLR/RAMP2 and 3 receptors. IMD exhibits no distinct preference for the three CLR/RAMP receptors. A peptide may be a superagonist for a specific receptor, relative to the native ligand for the receptor, or may be a superagonist with respect to multiple receptors, and any native ligand for one of the receptors.

In some embodiments a superagonist has activity that is greater than about 105%, 110%, 125%, 150%, 175%, 2-fold, 3-fold, 5-fold or more relative to a native ligand for the receptor or receptors.

Specific superagonist. A specific superagonist has high activity for a selected receptor, where the superagonist may be greater than about 3-fold, greater than about 5-fold, greater than about 10-fold, greater than about 20-fold or more, activity against one member of the CLR/RAMP receptor family. In some embodiments a superagonist is selective for CLR/RAMP1 relative to CLR/RAMP2. In other embodiments a superagonist is selective for CLR/RAMP2 relative to CLR/RAMP1.

A super-antagonist, or antagonist herein inhibits the biological activity of one or more receptors, particularly a receptor activated by ADM, IMD and CGRPs. A super-antagonist may inhibit the activity to a degree greater than the inhibition of a native ligand-derived antagonist. An antagonist or superantagonist may inhibit receptor activity by 105%, 110%, 125%, 150%, 175%, 2-fold, 3-fold, 5-fold or more, for example in the presence of a commonly known antagonistic ligand. A super-antagonist or antagonist may be pan-specific or receptor-selective.

A pan-specific superagonist, agonist, super-antagonist, or antagonist has activity for two or more receptors. In some embodiments the receptors include two or more of CLR/RAMP1, CLR/RAMP2 and CLR/RAMP3. In some embodiments the receptors are CLR/RAMP1, CLR/RAMP2 and/or CLR/RAMP3.

PEG moiety. A polyethylene glycol (PEG) moiety is defined as:

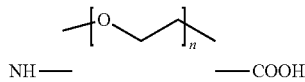

in which n is an integer number. Examples include a mini-PEG as defined by CAS number: 166108-71-0; Fmoc-NH-(PEG)-COOH, or Fmoc-8-amino-3,6-dioxaoctanoic acid; Molecular weight: 385.42 g/mol; having a structure:

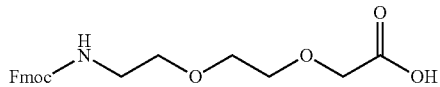

In a coupling reaction, a PEG moiety can behave similarly to amino acids: the free acid end of the PEG moiety will react with free amino group of the last N-terminus amino acid to form a peptide bond. In the following deprotecting procedure, the protecting group Fmoc is cleaved off to expose the free amino group of the PEG moiety.

Native adrenomedullin, intermedin or calcitonin gene-related peptides (CGRPs). As used herein, the term refers to the common wild-type counterparts of these peptides as known in the art. Included are the wild-type human peptides, although other mammalian counterparts may also find use, e.g. non-human primates, apes, canines, equines, murines, felines, lagomorphs, bovines, ovines, porcines, and the like.

The term "neurotensin receptor ligand" as used herein refers to any molecule that binds to a neurotensin receptor and agonizes or antagonizes a neurotensin receptor response. Neurotensin receptor ligands include, without limitation, neurotensin polypeptides and peptidic analogs. For example, a neurotensin receptor agonist can be a polypeptide such as neurotensin and analogs (e.g., [Lys 8,9] neurotensin) as known in the art, for example SEQ ID NOS:221 and 222. Typically, neurotensin receptor agonists induce neurotensin receptor responses such as antinociception, hypothermia, diminished food consumption, blockade of muscle rigidity (catalepsy) caused by antipsychotic drugs (e.g., haloperidol), and inhibition of climbing behavior caused by the dopamine receptor agonist apomorphine. Neurotensin receptor responses can be measured using any method. For example, neurotensin receptor effects can be measured in cells expressing recombinant neurotensin receptor by measuring the formation of second messengers (e.g., release of inositol phosphates or increase in intracellular levels of calcium ions). Neurotensin receptor ligands that can be used as described herein also can be peptidomimetic compounds designed on the basis of the amino acid sequences of neurotensin polypeptides. Peptidomimetic neurotensin compounds are synthetic compounds having a three-dimensional conformation (i.e., a "peptide motif) that is substantially the same as the three-dimensional conformation of a selected neurotensin polypeptide, and thus can confer the same or similar function as the selected polypeptide. Peptidomimetic analogs can be designed to mimic any of the neurotensin analogs provided herein. Several types of chemical bonds (e.g., ester, thioester, thioamide, retroamide, reduced carbonyl, dimethylene and ketomethylene) and modifications (acylation, pegylation, amino acid conjugation, and cyclization) can be used in the construction of peptidomimetic compounds.

The term "somatostatin receptor ligand" as used herein refers to any molecule that binds to a somatostatin receptor (SSTR1-5) and agonizes or antagonizes a somatostatin receptor response. Somatostatin receptor ligands include, without limitation, somatostatin polypeptides and peptidic analogs. For example, a somatostatin receptor agonist can be a polypeptide such as somatostatin-14 (SEQ ID NO: 216) and octreotide (SEQ ID NO: 215), and analogs as known in the art, for example somatostatin-28 (SEQ ID NO: 217). Typically, somatostatin receptor agonists induce somatostatin receptor responses such as inhibition of growth hormone release, growth factor release, blockade of tumor cell growth and proliferation. Somatostatin receptor responses can be measured using any method. For example, somatostatin receptor effects can be measured in cells expressing recombinant somatostatin receptor by measuring the formation of second messengers (e.g., release of inositol phosphates or increase in intracellular levels of calcium ions). Somatostatin receptor ligands that can be used as described herein also can be peptidomimetic compounds designed on the basis of the amino acid sequences of somatostatin polypeptides (e.g., octretide and lanreotide). Peptidomimetic somatostatin compounds are synthetic compounds having a three-dimensional conformation (i.e., a "peptide motif) that is substantially the same as the three-dimensional conformation of a selected somatostatin polypeptide, and thus can confer the same or similar function as the selected polypeptide. Peptidomimetic analogs can be designed to mimic any of the somatostatin analogs provided herein. Several types of chemical bonds (e.g., ester, thioester, thioamide, retroamide, reduced carbonyl, dimethylene and ketomethylene) and modifications (acylation, pegylation, amino acid conjugation, and cyclization) can be used in the construction of peptidomimetic somatostatin analogs.

The term "apelin receptor ligand" as used herein refers to any molecule that binds to an apelin receptor and agonizes or antagonizes an apelin receptor response. Apelin receptor ligands include, without limitation, apelin polypeptides and peptidic analogs. For example, an apelin receptor agonist can be a polypeptide such as apelin 13, and analogs described in prior publications (See Patent WO2014099984A1; U.S. Pat. Nos. 7,947,280 B2; 6,492, 324). Typically, apelin receptor agonists induce apelin receptor responses such as increases of cardiac output, changes in hemodynamics, protection cardiac cells against oxidative stress and injuries. Apelin receptor responses can be measured using any method. For example, Apelin receptor effects can be measured in cells expressing recombinant apelin receptor by measuring the formation of second messengers (e.g., release of inositol phosphates or increase in intracellular levels of calcium ions). Apelin receptor ligands that can be used as described herein also can be peptidomimetic compounds designed on the basis of the amino acid sequences of apelin polypeptides (e.g., apelin 13 (SEQ ID NO:225)). Peptidomimetic apelin compounds are synthetic compounds having a three-dimensional conformation (i.e., a "peptide motif) that is substantially the same as the three-dimensional conformation of a selected apelin polypeptide, and thus can confer the same or similar function as the selected polypeptide. Peptidomimetic apelin analogs can be designed to mimic any of the apelin analogs provided herein. Several types of chemical bonds (e.g., ester, thioester, thioamide, retroamide, reduced carbonyl, dimethylene and ketomethylene) and modifications (acylation, pegylation, amino acid conjugation, and cyclization) can be used in the construction of peptidomimetic compounds.

The term "bradykinin receptor ligand" as used herein refers to any molecule that binds to a bradykinin receptor and agonizes or antagonizes a bradykinin receptor response. Bradykinin receptor ligands include, without limitation, bradykinin polypeptides and peptidic analogs. For example, a bradykinin receptor antagonist can be a polypeptide such as R 715 (KRPPGFS-DβNal-I), and analogs described in prior publications. Typically, bradykinin receptor agonists induce bradykinin receptor responses such as increases of vascular permeability, vasodilation, increase of blood-brain barrier and inflammatory responses, and increases of oxidative stress and injuries; whereas bradykinin receptor antagonists block these responses. Bradykinin receptor responses can be measured using any method. For example, bradykinin receptor effects can be measured in cells expressing recombinant bradykinin receptor by measuring the formation of second messengers (e.g., release of inositol phosphates or calcium flux). Bradykinin receptor ligands that can be used as described herein also can be peptidomimetic compounds designed on the basis of the amino acid sequences of bradykinin polypeptides (e.g., bradykinin, HOE140, and KRPPGFS-DβNal-I). Peptidomimetic compounds are synthetic compounds having a three-dimensional conformation (i.e., a "peptide motif) that is substantially the same as the three-dimensional conformation of a selected polypeptide, and thus can confer the same or similar function as the selected polypeptide. Peptidomimetic analogs can be designed to mimic any of the bradykinin analogs provided herein. Several types of chemical bonds (e.g., ester, thioester, thioamide, retroamide, reduced carbonyl, dimethylene and ketomethylene) and modifications (acylation, pegylation, amino acid conjugation, and cyclization) can be used in the construction of peptidomimetic compounds.

The term "angiotensin II receptor ligand" as used herein refers to any molecule that binds to an angiotensin II receptor and agonizes or antagonizes an angiotensin II receptor response. Angiotensin II receptor ligands include, without limitation, angiotensin II polypeptides angiotensin II (for example SEQ ID NO: 232) and peptidic analogs. For example, an angiotensin II receptor antagonist can be a polypeptide such as telmisartan or saralasin (Sar-RVYVHPA; SEQ ID NO: 233), and analogs as known in the art. Typically, angiotensin II receptor agonists induce angiotensin II receptor responses such as increases in vessel constriction and elevation of blood pressure, increase of vessel rigidity and fibrosis, and stimulation of prothrombotic potential through adhesion and aggregation of platelets, and activation on the adrenal cortex, causing it to release aldosterone; whereas angiotensin II signaling antagonists block these responses. Angiotensin II receptor responses can be measured using any method. For example, angiotensin II receptor effects can be measured in cells expressing recombinant angiotensin II receptor by measuring the formation of second messengers (e.g., release of inositol phosphates or calcium flux). Angiotensin II receptor ligands that can be used as described herein also can be peptidomimetic compounds designed on the basis of the amino acid sequences of angiotensin II polypeptides (e.g., telmisartan and saralasin). Peptidomimetic angiotensin II compounds are synthetic compounds having a three-dimensional conformation (i.e., a "peptide motif) that is substantially the same as the three-dimensional conformation of a selected anagiotensin II polypeptide, and thus can confer the same or similar function as the selected polypeptide. Peptidomimetic analogs can be designed to mimic any of the angiotensin II analogs provided herein. Several types of chemical bonds (e.g., ester, thioester, thioamide, retroamide, reduced carbonyl, dimethylene and ketomethylene) and modifications (acylation, pegylation, amino acid conjugation, and cyclization) can be used in the construction of peptidomimetic compounds.

The term "MRL" refers to a peptide or derivative thereof that exhibits agonistic or antagonistic activity towards CLR/RAMP receptor(s) covalently or non-covalently linked to a second moiety that reacts with a second GPCR (that is a nonCLR/RAMP receptor). MRLs provide a unique therapeutic profile. A superagonistic or super-antagonistic CLR/RAMP receptor ligand together with or without a ligand of a second GPCR provides particular benefits for the treatment of disorders where the need for multiple signaling pathways and patient care with prescribed treatment are a challenge. For the treatment of disorders that are mediated by multiple signaling pathways, including but not limited to, cardiovascular, pulmonary, neurogenic, cutaneous, renal, gastrointestinal, skeletal, and metabolic diseases, one embodiment provides a multiple-pronged action toward multiple cell surface receptor signaling pathways.

Preferably a CLR/RAMP receptor agonist or antagonist is an ADM, CGRP, or IMD derivative or variant that can exhibit pan-specific or receptor-selective activity towards CLR/RAMP receptor1, 2 and/or 3. A CLR/RAMP1 ligand generally is a selective CLR/RAMP1 agonist or antagonist with less activity towards CLR/RAMP2 (e.g., CGRP alpha, CGRP beta and CGRP8-37). A CLR/RAMP2 ligand generally is a selective CLR/RAMP2 agonist or antagonist with less activity towards CLR/RAMP1 (e.g., ADM and ADM22-52). A pan-specific CLR/RAMP agonist or antagonist generally is a nonselective CLR/RAMP agonist or antagonist toward CLR/RAMP1 and 2. The second GPCR may be selected from somatostatin receptors, neurotensin receptors, apelin receptor, bradykinin receptors, and type 1 angiotensin II receptors.

A CLR/RAMP receptor agonist or antagonist for these purposes is not limited to agonist or antagonist, but can also include partial agonists and partial antagonist. Likewise, the definition of an MRL ligand for the second GPCR agonist or antagonist component is not limited to agonist or antagonist, but can also include partial agonist and partial antagonist. The receptor activity may be assessed in an adenosine 3',5'-cyclic monophosphate (cAMP), calcium, or an arrestin-linked signaling assay.

In one embodiment, provided herein is an MRL consisting of a somatostatin receptor ligand, a neurotensin receptor ligand, an apelin receptor ligand, a bradykinin receptor ligand, or an angiotensin II receptor ligand covalently linked to a CLR/RAMP receptor ligand. In another embodiment, provided herein is a pharmaceutical composition comprising a therapeutically effective amount of an MRL. In another embodiment, provided herein is a method for treating a disease or disorder associated with an MRL, in a subject, the method comprising: administering to said subject a therapeutically effective amount of an MRL.

The terms "comprising", "containing", and "including," are used herein in their open, non-limiting sense. "Conjugate" or "link" means a chemical compound that has been formed by the joining of two or more compounds.

The term "pharmaceutical composition" indicates a mixture containing ingredients that are compatible when mixed and which may be administered. A pharmaceutical composition may include one or more medicinal drugs. Additionally, the pharmaceutical composition may include carriers, buffers, acidifying agents, alkalizing agents, solvents, adjuvants, tonicity adjusters, emollients, expanders, preservatives, and chemical stabilizers (e.g. surfactants, antioxidants and other components), whether these are considered active or inactive ingredients. Guidance for the skilled in preparing pharmaceutical compositions may be found, for example, in Remington: The Science and Practice of Pharmacy, (20th ed.) ed. A. R. Gennaro A. R., (2000) Lippencott Williams & Wilkins and in R. C. Rowe et al (Ed), Handbook of Pharmaceutical Excipients, PhP, May 2013 update.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. "Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

As used herein, "pharmaceutically acceptable salt" refers to the non-toxic alkali metal, alkaline earth metal, and ammonium salts commonly used in the pharmaceutical industry including the sodium, potassium, lithium, calcium, magnesium, barium, ammonium, and protamine zinc salts. The term also includes non-toxic acid addition salts, which are generally prepared by reacting the ligand disclosed herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Thus, the term refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable salts as prodrugs, see Bundgaard, H. ed., 1985 *Design of Prodrugs*, Elsevier Science Publishers, Amsterdam.

As used herein, "pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H. ed. 1985 *Design of Prodrugs*, Elsevier Science Publishers, Amsterdam. The alcohol component of the ester will generally comprise (i) a $C_2$-$C_{20}$ aliphatic alcohol that can or cannot contain one or more double bonds and can or cannot contain branched carbons or (ii) a $C_7$-$C_{20}$ aromatic or heteroaromatic alcohols.

As used herein, "C-terminal amide" refers to an amide moiety which replaces the C-terminal hydroxyl moiety usually present at the carboxy-terminus of a polypeptide, such that the polypeptide ends with a carboxamide (i.e., C(=O)—$NH_2$ rather than a C-terminal carboxy (i.e. C(=O)—OH) moiety. These amides are typically formed from the corresponding carboxylic acid and an amine. Generally, amide formation can be accomplished via conventional synthetic techniques. See, for example, Mark, et al. 1980 *Encyclopedia of Chemical Technology*, John Wiley & Sons, New York.

As used herein, "pharmaceutically acceptable carrier" refers to a carrier medium which does not interfere with the effectiveness of the biological activity of the active ingredients and which is not toxic to the host or patient.

As used herein, "stereoisomer" refers to an entity having the same molecular weight, chemical composition, and bonding sequence as another, but having its atoms grouped differently in space about one or more chiral centers. That is, stereoisomers of the same chemical formula will contain identical chemical moieties located in different spatial orientations about at least one chiral center. When pure, stereoisomers have the ability to rotate plane-polarized light. The peptides disclosed herein may have one or more asymmetrical carbon atoms and therefore include various stereoisomers. All stereoisomers are included within the scope of the embodiments.

As used herein, "therapeutically" or "pharmaceutically-effective amount" as applied to the compositions as disclosed herein refers to the amount of composition sufficient to induce a desired biological result. That result can be alleviation of the signs, symptoms, or causes of a disease, or any other desired alteration of a biological system.

As used herein, the terms "peptide residue" and "peptidic structure" are intended to include peptides comprised of naturally-occurring L-amino acids and the corresponding D-amino acids, as well as peptide derivatives, peptide analogues and peptidomimetics of the naturally-occurring L-amino acid, or D-amino acid structures. Approaches to designing peptide analogues, derivatives and mimetics are known in the art. For example, see Veber and Freidinger (1985) *TINS* p. 392; Evans, et al. (1987) *J. Med. Chem.* 30:229. Peptidomimetics that are structurally similar to therapeutically useful peptides may be used to produce an equivalent or enhanced therapeutic or prophylactic effect, by methods known in the art and further described in the following references: Spatola, A. F. (1983) in: *Chemistry and Biochemistry of Amino Acids, Peptides, and Proteins*, B. Weinstein, eds., Marcel Dekker, New York, p. 267; Holladay, et al. (1983) *Tetrahedron Lett.* 24:4401-4404.

Systematic substitution of one or more amino acids of a consensus sequence with a D-amino acid of the same type (for example, D-lysine in place of L-lysine) may be used to generate more stable peptides. In addition, constrained peptides comprising a consensus sequence or a substantially identical consensus sequence variation may be generated by methods known in the art (Rizo, et al. (1992) *Ann. Rev. Biochem.* 61:387); for example, by adding internal cysteine residues capable of forming intramolecular disulfide bridges which cyclize the peptide, adding cyclic lactam bridge, or the use of flexible 6-aminohexanoic acid (Ahx), rigid aminoisobutyric acid (Aib), non-proteinogenic amino acid or D-amino acid residues to alter the stability of the ligand.

As used herein, a "derivative" of a compound, for example, a peptide or amino acid, refers to a form of that compound in which one or more reactive groups in the compound have been derivatized with a substituent group. Examples of peptide derivatives include peptides in which an amino acid side chain, the peptide backbone, or the amino- or carboxy-terminus has been derivatized (for example, peptidic compounds with methylated amide linkages or hydroxylated amino acids).

As used herein an "analogue" or "analog" of a compound refers to a compound which retains chemical structures of the reference compound necessary for functional activity of that compound yet which also contains certain chemical structures which differ from the reference compound. As used herein, a "mimetic" of a compound refers to a compound in which chemical structures of the referenced compound necessary for functional activity of that compound have been replaced with other chemical structures that mimic the conformation of the referenced compound. Examples of peptidomimetics include peptidic compounds in which the peptide backbone is substituted with one or more benzodiazepine molecules, peptides in which L-amino acids are substituted with the corresponding D-amino acids and "retro-inverso" peptides (see U.S. Pat. No. 4,522,752 by Sisto, James, G. L. et al. (1993) *Science* 260:1937-1942, and Goodman et al. (1981) *Perspectives in Peptide Chemistry* pp. 283-294). Other derivatives include substitution with non-proteinogenic amino acid, C-terminal hydroxymethyl derivatives, O-modified derivatives (for example, C-terminal hydroxymethyl benzyl ether) and N-terminally modified derivatives including substituted amides such as alkylamides and hydrazides.

As used herein, the term "amino acid structure" is intended to include the amino acid, as well as analogues, derivatives and mimetics of the amino acid that maintain the functional activity of the compound. For example, the term "phenylalanine" structure is intended to include phenylalanine as well as pyridylalanine and homophenylalanine. The term "leucine" structure is intended to include leucine, as well as substitution with valine, isoleucine or other natural or non-natural amino acid having an aliphatic side chain, such as norleucine.

The amino- and/or carboxy-terminus of the peptide compounds disclosed herein can be standard amino and carboxy termini as seen in most proteins. Alternatively, the amino- and/or carboxy-terminus of the peptide compound can be chemically altered by the addition or replacement of a derivative group. Amino-derivative groups which can be present at the N-terminus of a peptide compound include acetyl, aryl, aralkyl, acyl, epoxysuccinyl, PEG, and cholesteryl groups. Carboxy-derivative groups which can be present at the C-terminus of a peptide compound include alcohol, aldehyde, epoxysuccinate, acid halide, carbonyl, halomethane, diazomethane groups and carboxamide. Carboxamide is preferred.

As used herein, "imaging agent" refers to materials, which when covalently attached to a compound, permit detection of the compound, including but not limited to, detection in vivo in a patient to whom a CLR/RAMP receptor superagonist or supe-rantagonist has been administered. Suitable imaging agents are well known in the art and include, by way of example, radioisotopes, fluorescent labels (for example, fluorescein), and the like. Selection of the label relative to such factors is well within the skill of the art. Covalent attachment of the detectable label to the peptide or peptidomimetic is accomplished by conventional methods well known in the art. For example, when the $^{125}$I radioisotope is employed as the imaging agent, covalent attachment of $^{125}$I to the peptide or the peptidomimetic can be achieved by incorporating the amino acid tyrosine into the peptide or peptidomimetic and then iodinating the peptide (see, for example, Weaner, et al. (1994) Synthesis and Applications of Isotopically Labelled Compounds; pp. 137-140).

As used herein the term "therapeutic agent" means an agent capable of having a desired therapeutic effect for a specific disease indication, including without limitation, a heart failure or blood pressure-reducing agent.

As used herein, "modified" refers to a polypeptide which retains the overall structure of a related polypeptide but which differs by at least one residue from that related polypeptide. As used herein a "modified C-terminus" is a C-terminus of a polypeptide that has a chemical structure other than a standard peptide carboxy group, an example of such a modified C-terminus being a C-terminal carboxamide.

In addition, constrained peptides comprising a consensus sequence or a substantially identical consensus sequence variation may be generated by methods known in the art (Rizo, et al. (1992) Ann. Rev. Biochem. 61:387); for example, by adding internal cysteine residues or organic linkers capable of forming intramolecular bridges which cyclize the peptide, adding cyclic lactam bridge, or the use of flexible 6-aminohexanoic acid (Ahx), rigid aminoisobutyric acid (Aib) or D-amino acid residues to alter the stability of the ligand.

Synthetic non-proteinogenic amino acid or non-naturally occurring amino acids refer to amino acids which do not naturally occur in vivo but which, nevertheless, can be incorporated into the peptide structures described herein.

The modified peptides described herein can be prepared by, for example, by using standard solid phase techniques or liquid phase techniques (See Merrifield, (1963). Am. Chem. Soc. 85:2149; J. M. Stewart and J. D. Young, (1984) Solid Phase Peptide Syntheses 2nd Ed., Pierce Chemical Company). These procedures can also be used to synthesize peptides in which amino acids other than the 20 naturally occurring, genetically encoded amino acids are substituted at one, two, or more positions of any of the modified peptides as disclosed herein. For instance, naphthylalanine can be substituted for tryptophan, facilitating synthesis. Other synthetic amino acids that can be substituted into the peptides of the present embodiments include but are not limited to L-hydroxypropyl, L-3, 4-dihydroxy-phenylalanyl, d amino acids such as L-d-hydroxylysyl and D-d-methylalanyl, L-a-methylalanyl, β-amino acids, and isoquinolyl. D amino acids and non-naturally occurring synthetic amino acids can also be incorporated into the peptides of the present embodiments (see Roberts, et al. (1983) Unusual Amino/Acids in Peptide Synthesis 5:341-449). In some embodiments, the naturally occurring side chains of the 20 genetically encoded amino acids, or any other side chain as disclosed herein can be transposed to the nitrogen of the amino acid, instead of the α-carbon as typically found in peptides.

In some embodiments, the method of synthesis may comprise the step of chemically modifying one of more amino acid side chains in a precursor peptide, a conjugation or a truncation of the amino acid sequences to yield a compound of the invention. Such modification may, for example, introduce a non-naturally occurring amino acid, convert one or more amino acids into non-naturally occurring amino acids, introduce an intramolecular bridge between two amino acid side chains, e.g. by forming a lactam ring between a Glu and a Lys residue, or introduce a lipophilic substituent at a lysine, arginine, or histidine residue.

One or more of the amino acids of a CLR/RAMP receptor agonists and antagonists as well as MRLs compound may be a non-proteinogenic (non-naturally occurring) amino acid. Examples of non-proteinogenic amino acids may include, but are not limited to, para amino benzoic acid (PABA), 2-amino benzoic acid, anthranilic acid, p-hydroxybenzoic acid (PHBA), 3-amino benzoic acid, 4-aminomethyl benzoic acid, 4-amino salicylic acid (PAS), 4-amino cyclohexanoic acid 4-amino-phenyl acetic acid, 4-amino-hippuric acid, 4-amino-2-chlorobenzoic acid, 6-aminonicotinic acid, methyl-6-aminonicotinate, 4-amino methyl salicylate, 2-amino thiazole-4-acetic acid, 2-amino-4-(2-aminophenyl)-4-oxobutanoic acid (L-kynurenine), O-methyl serine, acetylamino alanine, β-alanine, β-(acetylamino)alanine, β-aminoalanine, β-chloroalanine, citrulline, homocitrulline, hydroxyproline, homoarginine, homoserine, homotyrosine, homoproline, ornithine, 4-amino-phenylalanine, sarcosine, biphenylalanine, homophenylalanine, 4-nitro-phenylalanine, 4-fluoro-phenylalanine, 2,3,4,5,6-pentafluoro-phenylalanine, norleucine, cyclohexylalanine, /V-methyl-alanine, /V-methyl-glycine, V-methyl-glutamic acid, tert-butylglycine, a-aminobutyric acid, a-aminoisobutyric acid (Aib), 2-aminoisobutyric acid, 2-aminoindane-2-carboxylic acid, selenomethionine, lanthionine. dehydroalanine, γ-aminobutyric acid, naphthylalanine, aminohexanoic acid, phenylglycine, pipecolic acid, 2,3-diaminoproprionic acid, tetrahydroisoquinoline-3-carboxylic acid, taurine, tert-leucine, tert-butylalanine, cyclohexylglycine, diethylglycine, and dipropylglycine. Non-proteinogenic amino acids may include D amino acids of alanine, arginine, aspartate, asparagine, cysteine, glutamate, glutamine, glycine, histidine, isoleucine, leucine, lysine, methionine, phenylalanine, proline, serine, threonine, tryptophan, tyrosine, and valine.

Some embodiments provide modified peptide agonists, antagonists, and MRLs that have 60%-99% amino acid sequence identity with a full-length polypeptide sequence as disclosed herein (e.g., SEQ ID NOS: 28-51, 69-70, 77-78, 92, 94, 101, 103, 110, 112, 114, 119-120, 121-125, 139-140, 142, 145-149, 150-159, 190-192, 210-211, 213-214, 218, 223-224, 228, 231, and 234) or any other specifically defined fragment of a full-length polypeptide sequence as disclosed herein.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Variations in the sequence of the agonist, antagonist, or MRL peptides described herein, can be made, for example, using any of the techniques and guidelines for conservative and non-conservative mutations set forth, for instance, in U.S. Pat. No. 5,364,934 (Drayna et al., issued Nov. 15, 1994). Variations may be a substitution, deletion or insertion of the agonist or antagonist peptides that results in a change in the amino acid sequence of the agonist, antagonist, or MRL peptides as compared with the reference peptide sequences. In some embodiments, the superagonist or superantagonists or MRLs of the invention may comprise functional fragments or variants thereof that have at most 34, 33, 32, 31 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions compared to one or more of the specific sequences recited below. Further, the compounds of the present invention may additionally have chemical modification of one or more of its amino acid side groups, a-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, follower alkyl, N-di-lower alkyl, PEG, and N-acyl modifications. Modifications of the terminal carboxy group include, without limitation, the amide, lower alkyl amide, dialkyl amide, and lower alkyl ester modifications. Furthermore, one or more side groups, or terminal groups, may be cyclized or protected by protective groups known to the ordinarily-skilled peptide chemist.

Stabilized superagonistic and super-antagonistic peptide derivatives are provided where the sequence and/or side chains of the peptide derivatives are altered. The bioactivity of the derivatives toward CLR/RAMP receptors is superior when compared to wild-type ADM, CGRP, or IMD. The stabilized superagonistic peptides also show superior pharmacological action as compared to wild-type peptides on the basis of their specific action on receptor-activation activities. Another embodiment of the invention comprises a functional group covalently attached to a CLR/RAMP agonist or antagonist. The functional group is chosen for its ability to act as a ligand of another cell surface receptor, for example somatostatin, neurotensin, apelin, bradykinin, and angiotensin II receptors, or other chemical moiety (e.g., acylation and pegylation) that improve the receptor-regulatory activities and/or increase the stability of the compounds. In an embodiment, such an agonist, antagonist, or MRL comprises a CLR/RAMP receptor ligand and a second functional group. The second functional group is acting as an extra payload of the compound, which is capable of acting on multiple GPCRs on the cell surface.

In an alternative embodiment, the two separate ligand components of an MRL are linked with a chemical bond that does not substantially affects the function of the CLR/RAMP receptor-regulatory activity. Linkers that are useful to link the two moieties have minimal immunogenicity and toxicity to the host. Examples of such linkers may be found in Roberts et al., (2002) Adv. Drug Del. Rev., vol. 54, pp. 459-476. Examples of suitable chemical moieties, in particular PEGs and equivalent polymers, are described in Greenwald et al., (2003) Adv. Drug Del. Rev., vol. 55, pp. 217-250. For example, styrene-maleic anhydride neocarzinostatin copolymer, hydroxylpropyl methacrylamide copolymer, dextran, polyglutamic acid, hydroxyethyl starch, and polyaspartic acid are other polymeric systems that can be employed to accomplish delivery and pharmacokinetic characteristics similar to a PEG system. In a preferred embodiment of the modified MRLs, the linker group is an amino acid, a {Gly}, 2 {Beta-Ala}, {GABA}, {Ava}, {Ahx}, {8-Aoc}, {AEA}, aminoethoxyacetic acid, {Mini-PEG}, AEEA, {Mini-PEG2}, AEEEP, {Mini-PEGS}, {PEG4}, {PEG6}, {PEG8}, {PEG11}, {PEG-12}, {Ado}, a succinimide, an acetamide, or a PEG group of 2-40 kDa. Furthermore, the linker may be vinyl sulphone or orthopyridyl disulfide.

Optionally, the modified peptide derivatives described herein are covalently linked to a heterologous moiety, which may comprise a polymer, an Fc, an FcRn binding ligand, immunoglobulin, albumin, a collagen-binding motif, a RGD motif, and an albumin-binding ligand, or by N-methylation. A covalently linked polymer may be selected from the group consisting of optionally substituted, saturated, or mono- or di-unsaturated, linear or branched C3-C100 carboxylic acids, preferably C4-C30 carboxylic acids and C4-C30 carboxylic diacids (acylation or lipidation), a polyethyleneglycol (PEG) moiety, a polypropylenglycol (PPG) moiety, a PAS moiety, which is an amino acid sequence comprising mainly alanine and serine residues or comprising mainly alanine, serine, and proline residues, the amino acid sequence forming random coil conformation under physiological conditions [US No. 2010/0292130 and WO 2008/155134], and a hydroxyethylstarch (HES) moiety [WO 02/080979], a Fc, a FcRn binding ligand, albumin and an albumin-binding ligand as well as an XTEN moiety (see Schellenberger, et al., (2009) Nature Biotechnology 27:1186-1192).

Where the covalent linkage is to PEG, the PEG molecular weight may be between about 0.2 kDa and about 100 kDa for ease in handling and manufacturing. For example, the PEG may have an average molecular weight of about 200, 500, 1000, 2000, 4000, 8000, 16,000, 32,000, 64,000, or 100,000 kDa. In some embodiments, the PEG may have a branched structure (U.S. Pat. No. 5,643,575; Morpurgo et al. (1996) Appl. Biochem. Biotechnol. 56:59-72; Vorobjev et al, (1999) Nucleosides Nucleotides 18:2745-2750; and Caliceti et al, (1999) Bioconjug. Chem. 10:638-646).

Optionally, modified peptide derivatives comprise one or more substitutions of disulfide bonds with lactam bridges to increase the metabolic stability of the peptides. Cystathiones are resistant towards thiol reduction. Therefore, substitutions of disulfides with thioethers, or selenosulfide, diselenide and ditelluride bridges can provide protection against reduction [Knerr et al., (2011) ACS Chem Biol, 6:753-760; Muttenthaler et al. (2010) J Med Chem., 53:8585-8596]. Peptide disulfide bond mimics based on diaminodiacids can also be used to improve the stability of analogs (Cui et al., (2013) Angew Chem, 125:9737-9741). The disulfide bridge can also be modified either by the insertion of linkers or bridges of a different nature.

The peptide compounds can be incorporated into polymer matrices that contain a drug molecule in a noncovalently bound state can be injectable as solution, hydro gels, micro particles or micelles [D. H. Lee et al, (2003) J. Contr. Rel., 92:291-299]. Permanent PEGylation of peptides or proteins can be used to enhance their solubility, reduce immunogenicity and increase half live by reducing renal clearance is known in the art [Caliceti P, Veronese F M. (2003) Adv. Drug Deliv. Rev. 55:1261-1277; T. Peleg-Shulman et al. (2004) J. Med. Chem., 47:4897-4904]. Optionally, modified peptide derivatives are modified by the addition of one or more alkane, fatty acid, carboxylic diacid, γ-glumatic acid, cholesterol, PEG-fatty acid, or PEG-cholesterol moieties to increase the metabolic stability of the peptides. For example, the peptide may comprise an amino terminal modification $R_1$ where $R_1$ is a functional group comprising a structure of Formula (W')(X')n(Y')n'(Z')n", wherein W' is a fatty acid, a long-chain fatty dicarboxylic acid, a fatty acid derivative or empty; X' is a PEG group, glutamic acid, γ-glutamic acid, a proteinogenic or non-proteinogenic amino acid, Lys, or empty; Y' is a PEG group, glutamic acid, γ-glutamic acid, a proteinogenic or non-proteinogenic amino acid, Lys, or empty; Z' is a proteinogenic amino acid, a non-proteinogenic amino acid, Lys, or empty; and each of n, n' and n" is an independently selected integer from 1 to 20, where R1 can be located on any side chain group of an amino acid in the peptide.

In another embodiment, stapled peptide analogs of the present invention, via the introduction of a synthetic brace (staple), can be synthesized using ring-closing metathesis to lock a peptide in a specific conformation and reduce conformational entropy.

MRLs are agonists or antagonists as determined by the observation that they are capable of regulating signaling of multiple GPCRs. In vitro potency determination in cellular assays of agonists or antagonists is quantified by determining the concentrations of EC50 or IC50, respectively. EC50 and IC50 values may be used as a numerical measure of agonist or antagonist potency at a given receptor. For example, an EC50 value is a measure of the concentration of a compound required to achieve half of that compound's maximal activity in a particular assay. Thus, for example, a compound having EC50 for CLR/RAMP1 lower than the EC50 for CLR/RAMP1 of wild type ADM or CGRP in a particular assay may be considered to have superior potency at the CLR/RAMP1 receptor than wild-type peptide(s). In some embodiments of the present invention, the EC50 for CLR/RAMP1 and/or EC50 for CLR/RAMP2 is below 10 nM, below 9 nM, below 8 nM, below 7 nM, below 6 nM, below 5 nM, below 4 nM, below 3 nM, below 2 nM, below 1 nM, below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, e.g. when assessed using the assay described in the Examples. In any given assay, the EC50 value of a compound may be assessed relative to the EC50 of human ADM or CGRP. Thus, the ratio of the EC50 value of the test compound to the EC50 value of wild type human ADM or CGRP at a given receptor may be less than 10, less than 5, less than 1, less than 0.1, less than 0.05 or less than 0.01. The ratio of the EC50 value of the test compound to the EC50 value of wild type CGRP (EC50[test compound]/EC50[CGRP]) at the CLR/RAMP1 or 2 receptor may be less than 10, less than 5, less than 1, less than 0.1, less than 0.05 or less than 0.01. The ratio of the EC50 value of the test compound to the EC50 value of wild type ADM (EC50[test compound]EC50[ADM]) at the CLR/RAMP1 or 2 receptor may be less than 10, less than 5, less than 1, less than 0.1, less than 0.05 or less than 0.01.

According to another embodiment, the somatostatin, neurotensin, and apelin receptor ligand components of the MRLs of the invention exhibit a relative agonistic activity of at least 0.1%, preferably at least 0.5%, compared to that of wild-type somatostatin-14, neurotensin 13, or apelin 13, respectively.

According to another embodiment, the bradykinin and angiotensin II receptor ligand component of the MRLs of the invention exhibit a relative activity of at least 0.1%, preferably at least 0.5%, compared to that of a common bradykinin receptor antagonist or an angiotensin II receptor antagonist (e.g., telmisartan), respectively.

In another embodiment, the somatostatin receptor ligand component of an MRL comprises a homolog, a variant, or a functional fragment of somatostatin-14 (SEQ ID NO: 216) or somatostatin 28 (SEQ ID NO: 217). In another embodiment, the somatostatin receptor ligand comprises an amino acid sequence that is about 60%, 65%, 70%, 75%, 80%, 85%, 90%, or 95% identical to somatostatin 14. Somatostatin ligands may include, for example, SEQ ID NO: 215-217, and derivatives thereof. The term somatostatin receptor ligand, as used herein, may refer to any functional peptide analogs which exhibits EC50 of a somatostatin receptor at least >0.1% compared to that of somatostatin-14. In one embodiment, the somatostatin receptor ligand is an octreotide or lanreotide analog. A somatostatin receptor ligand within the MRLs of the present invention, however, can be shorter (e.g., 6-13 or less amino acids in length) or longer (e.g., 15-40 or more amino acids in length). Each possibility represents a separate embodiment of the present invention. A somatostatin MRL may have the sequence set forth in SEQ ID NO: 218.

In another embodiment, the neurotensin receptor ligand component of an MRL comprises a homolog, a variant, or a functional fragment of a neurotensin (SEQ ID NO: 221), including without limitation the sequence of SEQ ID NO: 221-224. In another embodiment, neurotensin receptor ligand comprises an amino acid sequence that is about 60%, 65%, 70%, 75%, 80%, 85%, 90%, or 95% identical to (SEQ ID NO: 221). The term neurotensin receptor ligand, as used herein, may refer to any functional peptide analog which exhibits EC50 of a neurotensin receptor at least >0.1% compared to that of the wild-type neurotensin 13. In one embodiment, the neurotensin receptor ligand is a neurotensin 13 analog. A neurotensin receptor ligand within the MRLs of the present invention, however, can be shorter (e.g., 6-12 or less amino acids in length) or longer (e.g., 14-40 or more amino acids in length). Each possibility represents a separate embodiment of the present invention.

In another embodiment, the apelin receptor ligand component of an MRL comprises a homolog, a variant, or a functional fragment of apelin 13 and 36, including without limitation the sequence of SEQ ID NO; 225, 226 or 227. In another embodiment, the apelin ligand component comprises an amino acid sequence that is about 60%, 65%, 70%, 75%, 80%, 85%, 90%, or 95% identical to SEQ ID NOS: 225-227. The term apelin receptor ligand, as used herein, may refer to any functional peptide analog which exhibits EC50 of APJ receptor at least >0.1% compared to that of apelin 13. In one embodiment, the apelin receptor ligand is an apelin 13 analog. An apelin receptor ligand of the present invention, however, can be shorter (e.g., 6-12 or less amino acids in length) or longer (e.g., 14-40 or more amino acids in length). Each possibility represents a separate embodiment of the present invention. An apelin MRL may comprise the sequence of SEQ ID NO: 228.

In another embodiment, the bradykinin receptor ligand component of an MRL comprises a homolog, a variant, or a functional fragment of a bradykinin receptor antagonist, for example SEQ ID NO: 230; Firazyr or icatibant. In another embodiment, bradykinin receptor ligand comprises an amino acid sequence that is about 60%, 65%, 70%, 75%, 80%, 85%, 90%, or 95% identical to SEQ ID NO: 230 or icatibant. The term bradykinin receptor ligand, as used herein, may refer to any functional peptide analog which exhibits IC50 of a bradykinin receptor at least >0.1% compared to that of a common bradykinin antagonist. In one embodiment, the bradykinin receptor ligand is an analog of a bradykinin receptor antagonist. A bradykinin receptor ligand within the MRLs of the present invention, however, can be shorter or longer (e.g., 5-8 or less amino acids in length) or longer (e.g., 10-40 or more amino acids in length). Each possibility represents a separate embodiment of the present invention. A bradykinin MRL may comprise the sequence set forth in SEQ ID NO: 231.

In another embodiment, the angiotensin II receptor ligand component of an MRL comprises a homolog, a variant, or a functional fragment of an angiotensin II receptor antagonist (e.g., telmisartan or saralasin; SEQ ID NO: 233). In another embodiment, angiotensin II receptor ligand comprises an amino acid sequence that is about 60%, 65%, 70%, 75%, 80%, 85%, 90%, or 95% identical to SEQ ID NO: 233. The term angiotensin II receptor ligand, as used herein, may refer to any functional peptide analog which exhibits IC50 of a type 1 angiotensin II receptor at least >0.1% compared to that of telmisartan or saralasin. In one embodiment, the angiotensin II receptor ligand is a saralasin or telmisartan analog. An angiotensin II receptor ligand within the MRLs of the present invention, however, can be shorter or longer (e.g., 2-7 or less amino acids in length) or longer (e.g., 9-40 or more amino acids in length). Each possibility represents a separate embodiment of the present invention. An angiotensin MRL may comprise the sequence of SEQ ID NO: 234.

The compounds described herein are particularly suitable for the treatment or prevention of diseases or disorders caused by, associated with and/or accompanied by the metabolic syndrome, hypertension, diabetes, atherogenic dyslipidemia, atherosclerosis, arteriosclerosis, coronary heart disease, vascular injury, wound injury, pain, migraine, tumor angiogenesis, cancer metastasis, HAE, pulmonary injury, chronic kidney diseases, or stroke. Their effects in these conditions may be as a result of or associated with their effect on tissue regeneration, angiogenesis, hemodynamics, anti-ischemia, or may be independent thereof. Thus, the compounds of the invention can be used for direct or indirect therapy of any condition caused or characterized by hypertension, endothelial dysfunction, damages to cardiovascular tissues, heart failure, coronary heart disease, ischemic and/or hemorrhagic stroke, macrovascular disease, microvascular disease, diabetic heart (including diabetic cardiomyopathy and heart failure as a diabetic complication) coronary heart disease, peripheral artery disease, peripheral arterial occlusive disease, pre-eclampsia, resistant hypertension, refractory hypertension, intradialysis hypertension, hypertensive crisis, blood or fetal-placental circulation, edematous diseases, pulmonary dysfunction, traumatic wounds, bronchopulmonary dysplasia (BPD), acute lung injury/acute respiratory distress syndrome (ALI/ARDS), trauma and/or burns, and/or ventilator induced lung injury (VILI), pulmonary fibrosis, mountain sickness, chronic kidney diseases, acute kidney injury, lymphedema, lymphatic vessel regeneration, inflammatory bowel disease, inflammatory disease, or ocular disorders associated with disturbed vascular function, topical wounds, diabetic ulcer, headache, migraine, inflammatory pain, neuropathic pain, tumors, metastasis, angiogenesis, degeneration of cartilage, osteoarthritis, and cancers.

Further preferred medical uses include treatment or prevention of degenerative disorders, particularly neurodegenerative disorders such as Alzheimer's disease, Parkinson's disease, Huntington's disease, ataxia, e.g spinocerebellar ataxia, myotonic dystrophy, Lewy body dementia, multisystemic atrophy, amyotrophic lateral sclerosis, spinal muscular atrophy, cerebral β-amyloid angiopathy, retinal ganglion cell degeneration in glaucoma, synucleinopathies, tauopathies, dementia, hereditary cerebral hemorrhage with amyloidosis, Alexander disease, seipinopathies, familial amyloidotic neuropathy, senile systemic amyloidosis, serpinopathies, Retinitis pigmentosa with rhodopsin mutations, medullary thyroid carcinoma, cardiac atrial amyloidosis, pituitary prolactinoma, hereditary lattice corneal dystrophy, cutaneous lichen amyloidosis, Mallory bodies, corneal lactoferrin amyloidosis, pulmonary alveolar proteinosis, cystic fibrosis, sickle cell disease or critical illness myopathy (CIM).

Without wishing to be bound by any particular theory, the modification of the CLR/RAMP receptor agonists and antagonists as well as MRLs appears to provide significant improvement on receptor-activation or receptor-blocking activities toward at least one of the CLR/RAMP receptors and may increase/enhance the stability of the peptide towards enzymatic degradation and in vivo clearance.

Without wishing to be bound by any particular theory, the addition of a PEG moiety and/or a fatty acid derivative to the CLR/RAMP receptor agonists and antagonists as well as MRLs appears to provide significant pan-specific activity for at least the CLR/RAMP1 and 2 receptors and may increase potency at least one of the CLR/RAMP receptors.

Without wishing to be bound by any particular theory, it is believed that the addition of a PEG moiety and/or a fatty acid derivative to MRLs may be performed without affecting the CLR/RAMP receptor-regulatory activity.

Without wishing to be bound by any particular theory, the addition of a somatostatin receptor agonist to a CLR/RAMP receptor agonist or antagonist may generate an MRL that is capable of regulating CLR/RAMP receptors and somatostatin receptors.

Without wishing to be bound by any particular theory, the addition of a neurotensin receptor agonist to a CLR/RAMP receptor agonist or antagonist may generate an MRL that is capable of regulating CLR/RAMP receptors and neurotensin receptors.

Without wishing to be bound by any particular theory, the addition of an apelin receptor agonist to a CLR/RAMP receptor agonist or antagonist may generate an MRL that is capable of regulating CLR/RAMP receptors and apelin receptor.

Without wishing to be bound by any particular theory, the addition of a bradykinin receptor antagonist to a CLR/

RAMP receptor agonist or antagonist may generate an MRL that is capable of regulating CLR/RAMP receptors and bradykinin receptors.

Without wishing to be bound by any particular theory, the addition of an angiotensin II receptor antagonist to a CLR/RAMP receptor agonist or antagonist may generate an MRL that is capable of regulating CLR/RAMP receptors and type 1 angiotensin II receptor.

The present invention also includes prodrugs of the compounds, i.e. compounds which themselves can be biologically active or inactive, but are converted (for example metabolically or hydrolytically) into active compounds in the body. Prodrugs may be based on masking amine functionalities, or masking the phenolic group of a tyrosine (the internal nucleophile assisted cleavage of a carbamate on the phenolic group); and the like.

Polymer based prodrugs are provided that comprise superagonistic peptide, super-antagonistic peptides, or MRLs described herein. A prodrug is any compound that undergoes biotransformation before exhibiting its pharmacological effects. Carrier-linked prodrug (Carrier prodrug) comprises a temporary linkage of a given active substance with a transient carrier group that produces improved physicochemical or pharmacokinetic properties and that can be removed in vivo, by a biochemical cleavage. PEG-based carrier prodrugs need enzymatic activation of the linker between the active drug and the carrier, mostly initiated by enzymatic hydrolysis. Commonly used cascading linkers attach an amine functionality in the peptide or protein. In cascading linkers a masking group is removed as the rate limiting step in the cascade. This activates the linker to decompose in a second position to release the peptide or protein. Commonly the masking group can be removed by an enzymatic mechanism [R. B. Greenwald et al. in WO 2002/089789, Greenwald, et al. (1999) J. Med. Chem. 42:3657-3667, F. M. H. DeGroot et al. in WO 2002/083180 and WO 2004/043493, and D. Shabat et al. in WO 2004/019993]. An alternative not relying on enzymatic activation (see WO 2005/099768) utilizes a masking group on a phenol, which removed in a purely pH dependent manner by the attack of an internal nucleophile. This activates the linker for further decomposition (see U.S. Pat. No. 8,680,315). Upon pH triggered decomposition the drug is released. Another approach optimized for phenols, e.g. tyrosine, is based on a carbamate that is pH dependently attacked by a nucleophilic amine under release of the phenol and generation of a cyclic urea attached to the macromolecule as described in WO 2013/064455.

The pharmacokinetic properties of peptides can be adjusted by lipidation. Lipidation can occur to the N-terminus or to the side chain functionalities of amino acids within the peptide sequence. Lipidation is described in publications and patents (Zhang et al. (2012) Curr Med 19:1602-1; Gerauer et al. (2009) Wiley Encyclopedia of Chemical Biology, Volume 2, 520-530, (Hrsg. Begley, T. P.). John Wiley & Sons, Hoboken, N.J.). Lipidation of an ADM sequence is described in WO 2012/138867. Labeled ADM derivatives for use as imaging and also therapeutic agent are known [J. Depuis et al. in CA 2567478 and WO 2008/138141]. In these ADM derivatives a complexating cage like molecular structure capable of binding radioactive isotopes was attached to the N terminus of ADM in a direct manner or via a spacer unit potentially also including short PEG spacers. The diagnostic or therapeutic value of theses drugs arises from the targeted delivery of the radioactive molecule.

In certain aspects, the compounds of the invention are provided in which one or more of the amino acid side chains may be conjugated to a lipophilic moiety. Without wishing to be bound by theory, it is thought that the lipophilic substituent binds albumin and other serum proteins in the blood stream, thus shielding the compounds employed in the context of the invention from enzymatic degradation and kidney clearance. For example, in certain aspects acylated CLR/RAMP receptor agonists have been shown to have longer half-life when compared to wild-type peptides. The superagonists and super-antagonists as well as MRLs provided herein in which a PEG and/or fatty acid moiety is attached to the amino group of an amino acid directly or via a linker. In certain aspects a linker is incorporated between the amino acid and the fatty acid (or fatty acid derivative). This linker can be an amino acid such as γ-glutamic acid, a PEG linker, or a PEG-γ-glutamic acid linker, or an alternative linker such as, but not limited to, beta alanine and aminohexanoic acid. The fatty acid could have one or two carboxylic acid groups (e.g., a fatty diacid). In the context of the present invention, these modifications lead to the generation of analogs that exhibit superagonistic and super-antagonistic activities toward CLR/RAMP1 and/or 2.

In certain embodiments, only one amino acid side chain is conjugated to a lipophilic and/or PEG moiety. In other embodiments, multiple amino acid side chains are conjugated to a lipophilic and/or PEG moiety. When a compound contains two or more lipophilic substituents, the lipophilic or PEG moiety may be the same or different. The lipophilic/PEG moiety may be covalently bonded to an atom in the amino acid side chain, or alternatively may be conjugated to the amino acid side chain by one or more spacers to provide a spacing between the compound and the lipophilic moiety via an ester, a sulphonyl ester, a thioester, an amide or a sulphonamide. The spacer may be, for example, a residue of any naturally occurring or unnatural amino acid. For example, the spacer may be a residue of Gly, Pro, Ala, Val, Leu, Ile, Met, Cys, Phe, Tyr, Trp, His, Lys, Arg, Gln, Asn, a-Glu, γ-Glu, ε-Lys, Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8-amino-3,6-dioxaoctanoyl. In certain embodiments, the spacer is a residue of Glu, γ-Glu, ε-Lys, β-Ala (i.e. 3-aminopropanoyl), 4-aminobutanoyl, 8-aminooctanoyl, 8-amino-3,6-dioxaoctanoyl, or a PEG group. In the present context, γ-Glu and isoGlu are used interchangeably. In some embodiments, the amino acid linker may be selected from γ-Glu, a-Glu, a-Asp, β-Asp, Ala, β-Ala (3-aminopropanoic acid), Dapa (2,3-diaminopropanoic acid), Dab (2,4-diaminobutanoic acid), and Gaba (4-aminobutanoic acid). Other suitable amino acids include β-Ala (3-aminopropanoic acid) and Gaba (4-aminobutanoic acid) and similar ω amino acids. It will be understood that where more than one carboxylic acid or amino moiety is present, connection may be at any moiety as appropriate. The amino acid side chain to which the lipophilic moiety is conjugated is a side chain, e.g., of a Glu, Lys, Ser, Cys, Dbu, Dpr or Orn residue. For example, it may be a side chain of a Lys, Arg, His, Glu, Asp, or Cys residue. Where two or more side chains carry a lipophilic moiety they may be independently selected from these residues. Thus the amino acid side chain includes a carboxy, hydroxyl, thiol, amide or amine group, for forming an ester, a sulphonyl ester, a thioester, an amide, or a sulphonamide with the spacer or lipophilic substituent. The lipophilic moiety may include a hydrocarbon chain having 6 to 28 carbon atoms. The hydrocarbon chain may be linear or branched and may be saturated or unsaturated. Furthermore, it can include a functional group in the end of the lipophilic chain, e.g., carboxylic acid which may or may not be protected during synthesis. The hydrocarbon chain is substituted with acyl, and accordingly the hydrocarbon chain may be part of an alkanoyl group, for example a dodecanoyl, 2-butyloctanoyl, tetradecanoyl, hexadecanoyl, heptadecanoyl, octadecanoyl or eicosanoyl group. The fatty chain may also have one or more cycloalkylene or heterocycloalkylene moieties in its length, and additionally or alternatively may have one or more arylene or heteroarylene moieties in its length. For example, the fatty chain may incorporate a phenylene or piperazinylene moiety in its length. Examples of linear saturated fatty acids from which suitable fatty chains may be derived include tridecylic (tridecanoic) acid, myristic (tetradecanoic) acid, pentadecylic (pentadecanoic) acid, palmitic (hexadecanoic) acid, and margaric (heptadecanoic) acid. Examples of linear unsaturated fatty acids from which suitable fatty chains may be derived include myristoleic acid, palmitoleic acid, sapienic acid and oleic acid. Optional substituents on the fatty chain may be independently selected from fluoro, Ci-4alkyl, preferably methyl; trifluoromethyl, hydroxymethyl, amino, hydroxyl, Ci-alkoxy, preferably methoxy; oxo, and carboxyl, and may be independently located at any point along the chain. In some embodiments, each optional substituent is selected from fluoro, methyl, and hydroxy I. Where more than one substituent is present, substituents may be the same or different. The lipophilic moiety could also be combined with additional amino acid(s) and PEG moieties in any order to provide additional spacing and protection as well as to enhance bioactivity. Examples of lipophilic moieties include, but are not limited to, hexadecanoyl-isoGlu-PEG3, hexadecanoyl-isoGlu-PEG3-PEG3, hexadecanoyl-PEG3-isoGlu, [19-carboxy-nonadecanoyl]-isoGlu, [19-carboxy-nonadecanoyl]-PEG3-isoGlu, [19-carboxy-nonadecanoyl]-isoGlu-Peg3-Peg3, [17-carboxy-heptadecanoyl]-isoGlu-Peg3-Peg3, [19-carboxy-nonadecanoyl]-isoGlu-PEG3, [19-carboxy-nonadecanoyl]-isoGlu-PEG3. This combination of lipophilic moiety and spacer, conjugated to an amino acid residue, may be referred to by the shorthand notation K(Hexadecanoyl-γ-Glu), e.g., when shown in formulae of specific compounds. γ-Glu can also be referred to as isoGlu, and a hexadecanoyl group as a palmitoyl group. Thus it will be apparent that the notation (hexadecanoyl-γ-Glu) is equivalent to the notations (isoGlu(Pal)) or (isoGlu(Palmitoyl)).

The present invention also encompasses all suitable isotopic variants of the compounds according to the invention. An isotopic variant of a compound is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound may be beneficial, for example, for the examination of the mechanism of action or of the active compound distribution in the body. In addition, the incorporation of isotopes, for example of deuterium, can lead to particular therapeutic benefits as a consequence of greater metabolic stability of the compound, for example an extension of the half-life in the body or a reduction in the active dose required.

Peptide Compositions and Formulations

Provided herein are compounds of the formula (I)-(V) and the salts thereof, solvates thereof and solvates of the salts thereof. The compounds may be specifically set forth as working examples. The inventive peptide may be subjected to directed chemical modifications, such as maleimide capping, polyethylene glycol (PEG) attachment, maleidification, acylation, alkylation, esterification, and amidification, to produce structural analogs of the peptide. One skilled in the art would appreciate the existence of a variety of chemical modification techniques and moieties, see for example U.S. Pat. Nos. 5,554,728, 6,869,932, 6,828,401, 6,673,580, 6,552,170, 6,420,339, U.S. Pat. Pub. 2006/0210526 and Intl. Pat. App. WO 2006/136586. Preferably, chemical modifications are performed on isolated peptide, e.g., to increase functional efficiencies.

The peptides described herein are optionally provided as a miniaturized molecular mass that facilitates the permeation and diffusion of molecules in vivo, and the access to the central nervous system, thereby increasing the onset of treatment and volume of distribution as well as improving the utility in the treatment of diseases. The generation of miniaturized receptor agonists or antagonists, or MRLs with miniaturized CLR/RAMP ligand not only facilitates the diffusion of the peptides within extracellular fluid, but also allows the molecules to enter limited space that is too small to allow the entrance of a larger analog. Prior ADM or IMD analogs were 39 and 40 amino-acid long, respectively; and CGRP and ADM antagonistic analogs were 30 amino acids in length. The peptides provided herein comprise examples of miniaturized superagonists of 35-36 amino-acid in length, and miniaturized super-antagonists of 17-28 amino-acid in length. The miniaturized analogs are also unique in that no CLR/RAMP receptor ligands that contain a truncation in the middle of the continuous sequences of the wild type peptides have been previously described.

Agonists and Superagonists

In some embodiments, a CLR/RAMP receptor superagonist has the structure of Formula I:

$$B^a\text{-}C^a\text{-}D^a \qquad (I)$$

wherein $B^a$ is a modified N-terminal fragment of adrenomedullin peptide family member comprising from twenty to twenty eight amino acid residues, wherein two amino acid residues of the N-terminal fragment are cysteine (Cys), and wherein the C-terminal residue of the fragment is threonine (Thr). $B^a$ may be represented by the structure: ($B^0\text{-}B^1\text{-}B^2\text{-}C\text{-}B^4\text{-}B^5\text{-}G\text{-}B^7\text{-}C\text{-}B^9\text{-}B^{10}\text{-}B^{11}\text{-}B^{12}\text{-}B^{13}\text{-}B^{14}\text{-}B^{15}\text{-}B^{16}\text{-}B^{17}\text{-}B^{18}\text{-}B^{19}\text{-}B^{20}\text{-}B^{21}$; SEQ ID NO:1);

$C^a$ is a central core consist of 3-12 amino acids; and $D^a$ is a modified C-terminal fragment of intermedin (IMD) or ADM comprising 3-6 amino acid residues with a C-terminal amide, where at least one amino acid of $D^a$ is selected from proline (P), serine (Ser), and tyrosine (Tyr).

In some embodiments, $B^a$ is characterized by two cysteines present in the sequence that form a disulfide bond. Residues between the two cys residues involved in the disulfide bond are unconstrained in sequence. The aforementioned disulfide bond stabilizes the structure of $B^a\text{-}C^a\text{-}D^a$, facilitating both formation of an alpha-helix, and binding of $B^a\text{-}C^a\text{-}D^a$ to the binding domain component of a target receptor.

Introduction of a mini-PEG together with an acylation modification at the N-terminus, or an acylation modification in the absence of mini-PEG at the N-terminus of a peptide of Formula I results in a superagonist activity of the molecule in interactions with a CLR/RAMP1 or a CLR/RAMP2 receptor when compared to the wild-type ADM (SEQ ID NOS: 53-54), IMD (SEQ ID NO: 52), or a chimeric peptide with inappropriate sequences (SEQ ID NOS: 55-68). Such modifications yield a molecule that occupies the receptor and activates the signal transduction pathway at a greater than about 3-fold increase in receptor-activation potency for at least one of the CLR/RAMO receptors when compared with the wild-type ADM, IMD, CGRP, or chimeric ligands in the absence of such acylation and/or pegylation modification. In some embodiments, a superagonist comprises acylation modification in the absence of mini-PEG.

Addition of residues N-terminal to the first cysteine of $B^a$-$C^a$-$D^a$ may not affect the superagonistic characteristics of the polypeptide. In some embodiments the peptide is joined to an amino acid residue or polypeptide at the residues N-terminal to the first cysteine of the peptide of Formula I. The peptide of formula I may be joined to a polypeptide, e.g. a serum polypeptide such as albumin, an immunoglobulin, including an immunoglobulin constant region, and the like.

In some embodiments, a CLR/RAMP receptor superagonist of Formula I comprises, consists or consists essentially of an amino acid sequence selected from the group consisting of (where "pal" signifies a palmitate moiety, and "ace" signifies acetylated terminus):

(SEQ ID NO: 28)
mini-PEG-K(PAL)GCRFGTCTVQKLAHQIYQFTDKDKDNSAPVDPSSPHSY-$NH_2$ (SEQ ID NO: 29)
mini-PEG-K(PAL)GCRFGTCTVQKLAHQIYQFTPAGRQDSAPVDPSSPHSY-$NH_2$ (SEQ ID NO: 30)
Pal-KGCRFGTCTVQKLAHQIYQFTDKDKDNSAPVDPSSPHSY-$NH_2$ (SEQ ID NO: 31)
Pal-KGCRFGTCTVQKLAHQIYQFTPAGRQDSAPVDPSSPHSY-$NH_2$ (SEQ ID NO: 32)
Ace-K(PAL)GCRFGTCTVQKLAHQIYQFTDKDKDNSAPVDPSSPHSY-$NH_2$ (SEQ ID NO: 33)
Ace-K(PAL)GCRFGTCTVQKLAHQIYQFTPAGRQDSAPVDPSSPHSY-$NH_2$ (SEQ ID NO: 34)
Pal-KGCRFGTCTVQKLAHQIYQFTDKDKDNVAPVDPSSPHSY-$NH_2$, (SEQ ID NO: 35)
Pal-KGCRFGTCTVQKLAHQIYQFTDKDKQDSAPVDPSSPHSY-$NH_2$, (SEQ ID NO: 36)
Pal-KGCRFGTCTVQKLAHQIYQFTDKGRQDSAPVDPSSPHSY-$NH_2$, (SEQ ID NO: 37)
Pal-K(Pal)GCRFGTCTVQKLAHQIYQFTDKDKDNSAPVDPSSPHSY-$NH_2$, (SEQ ID NO: 38)
Pal-KTKKTLRTGCRFGTCTVQKLAHQIYQFTDKDKDNSAPVDPSSPHSY-$NH_2$, (SEQ ID NO: 39)
Ace-TK(Pal)KTLRTGCRFGTCTVQKLAHQIYQFTDKDKDNSAPVDPSSPHSY-$NH_2$;

(SEQ ID NO: 40)
Pal-KTKKTLRTGCRFGTCTVQKLAHQIYQFTDKDKDNVAPVDPSSPHSY-$NH_2$,

-continued (SEQ ID NO: 41)
Ace-TK(Pal)KTLRTGCRFGTCTVQKLAHQIYQFTDKDKDNVAPVDPSSPHSY-$NH_2$.

(SEQ ID NO: 42)
miniPEG-TK(Pal)KTLRTGCRFGTCTVQKLAHQIYQFTDKDKDNVAPVDPSSPHSY-$NH_2$.

(SEQ ID NO: 43)
miniPEG-K(PAL)CRFGTCTVQKLAHQIYQFTDKDKDNSAPVDPSSPHSY-$NH_2$.

(SEQ ID NO: 44)
Pal-KCRFGTCTVQKLAHQIYQFTDKDKDNSAPVDPSSPHSY-$NH_2$.

(SEQ ID NO: 45)
Pal-GCRFGTCTVQKLAHQIYQFTDKDKDNSAPVDPSSPHSY-$NH_2$.

(SEQ ID NO: 46)
miniPEG-K(PAL)GCRFGTCTVQKLAHQIYQFTDKDKDSAPVDPSSPHSY-$NH_2$.

(SEQ ID NO: 47)
miniPEG-K(PAL)GCRFGTCTVQKLAHQIYQFTDKDKSAPVDPSSPHSY-$NH_2$.

(SEQ ID NO: 48)
miniPEG-K(PAL)GCRFGTCTVQKLAHQIYQFTDKDSAPVDPSSPHSY-$NH_2$.

(SEQ ID NO: 49)
miniPEG-K(PAL)GCRFGTCTVQKLAHQIYQFTPAGRQDSAPVDPSSPHSY-$NH_2$.

(SEQ ID NO: 50)
miniPEG-K(PAL)GCRFGTCTVQKLAHQIYQFTDKDKDNVAPVDPSSPHSY-$NH_2$.

(SEQ ID NO: 51)
miniPEG-K(PAL)GCRFGTCTVQKLAHQIYQFTDKDKQDSAPVDPSSPHSY-$NH_2$ (SEQ ID NO: 69)
mini-PEG-K(PAL)GCRFGTCTVQKLAHQIYQFTDKDKDNVAPRSKISPQGY-$NH_2$ (SEQ ID NO: 70)
miniPEG-K(PAL)TKKTLRTGCRFGTCTVQKLAHQIYQFTDKDKDNVAPRSKISPQGY-$NH_2$ (SEQ ID NO: 92)
Pal-KGCRFGTCTVQKLAHQIYQFTDKDSAPVDPSSPHSY-$NH_2$.

(SEQ ID NO: 94)
miniPEG-K(PAL)GCRFGTCTVQKLAHQIYQFTDKDKDNVDPSSPHSY-$NH_2$ (SEQ ID NO: 101)
miniPEG-K(PAL)GCRFGTCTVQKLAHQIYQFTDKDVAPRSKISPQGY-$NH_2$ (SEQ ID NO: 103)
Pal-KGCRFGTCTVQKLAHQIYQFTDKDVAPRSKISPQGY-$NH_2$ (SEQ ID NO: 110)
Pal-KGCRFGTCTVQKLAHQIYQFTDKDAPVDPSSPHSY-$NH_2$ The peptides may comprise fragments derived from ADM and/or IMD, as evident by an alignment of the sequences.

In some embodiments, one or more amino acid residues are fused N-terminally to $B^1$, thereby generating a polypeptide with an N-terminal extension of residues with respect to $B^1$. In some embodiments the extension does not affect the bioactivity of the superagonist.

In some embodiments the superagonist of Formula I, as disclosed herein, comprises a central core $C^a$ comprising 3 to 12 amino acid residues. The length of the central core is constrained not by the number of residues but by the steric considerations that require $B^a$ and $D^a$ to be positioned so that they may interact with a target receptor at the cell membrane surface. In some embodiments of the CLR/RAMP receptor superagonist having the structure of Formula I, the central core comprises a fragment of adrenomedullin or intermedin from any of a range of species, including without limitation mammalian species. In some embodiments, $C^a$ has sequence identity of at least 60%, of at least 85%, of at least 90%, of at least 95%, of at least 99%, or 100% with the sequence DKDKDNVAPRSK (SEQ ID NO: 18), DKDKDNSAPVDP (SEQ ID NO: 19), PAGRQDSAPVDP (SEQ ID NO: 20), DKDKDNVAPVDP (SEQ ID NO: 21), DKDKQDSAPVDP (SEQ ID NO: 22), DKGRQDSAPVDP (SEQ ID NO: 23), DKDKDSAPVDP (SEQ ID NO: 24), DKDKSAPVDP (SEQ ID NO: 25), or DKDSAPVDP (SEQ ID NO: 26). In some embodiments, $C^a$ has an 60% or greater sequence identity with any of SEQ ID NO: 18-26.

$D^a$ is a C-terminal fragment of IMD or ADM peptide comprising 3, 4, 5, 6, or more amino acid residues from the C-terminus of intermedin or adrenomedullin. $D^a$ has a C-terminal amide. At least one amino acid of $D^a$ is selected from proline (Pro), histidine (His), tyrosine (Tyr), and serine (Ser). Like $C^a$ above, $D^a$ is constrained not by its sequence but by its ability to interact with CLR/RAMP1 and/or CLR/RAMP2 receptors. In the case of $D^a$ that requirement is that it interacts with a target receptor at a site in its extracellular domain such that when the agonist binds the receptors become activated.

In some embodiments $D^a$ comprises at least one tyrosine residue. In some embodiments the C-terminus of $D^a$ is modified so that it comprises an amidated carboxy (—C(=O)NH$_2$) moiety.

In some embodiments a CLR/RAMP2 receptor-selective superagonist comprises, consists or consists essentially of the peptide of SEQ ID NOS: 69, 70, 94, 101, 103, 110, 210, 211, or 214.

In some embodiments herein a CLR/RAMP receptor superagonist is provided herein that retains the sequence of an agonist that binds the CLR/RAMP receptors at the cellular membrane, but that differs at least one amino acid residue from the wild-type sequence. In a preferred embodiment, the chimeric superagonists derived from ADM and IMD are part of the structure used to increase efficacy of the superagonist or super-antagonist.

In some embodiments $B^a$ is selected from the group consisting of the peptide of SEQ ID NOS:1-16. In some embodiments a CLR/RAMP receptor superagonist of Formula I comprises a first peptide fragment having from about nineteen amino acid residues or more from an ADM sequence, including without limitation human ADM, a second peptide fragment having from about three amino acid residues or more from ADM and IMD, including without limitation human ADM and IMD, and a third peptide fragment from IMD or ADM, including without limitation human IMD or ADM. In some embodiments a CLR/RAMP receptor superagonist of Formula I, comprises a contiguous second and third peptide fragment.

Antagonists and Superantagonists

Certain select amino acids in the N-terminal portion of the ADM/CGRP/IMD family peptides are responsible for the peptide agonist activity. Truncation or substituting of certain amino acids in the N-terminal portion of these peptides can tune the activity from an agonist to an antagonist. It has been discovered that additional substitutions or modifications can provide additional desirable characteristics to the antagonists. For example, the blockage of CGRP signaling may be useful for preventing the development or progression of migraine headache; whereas the blockage of CLR/RAMP2 signaling represents an anti-angiogenesis approach to reduce tumor growth and cancer progression. However, existing CLR/RAMP receptor antagonists are associated with efficacy concerns. Peptide antagonists such as CGRP8-37 and ADM22-52 have extremely short half-lives and low potencies, and are receptor-specific.

In some embodiments, a CLR/RAMP receptor super-antagonist is provided, said antagonist having the structure of Formula II:

$$R1-B^b-C^b-D^b-R2 \qquad (II)$$

wherein $B^b$ is an N-terminal fragment of adrenomedullin peptide family member comprising from four to thirteen amino acid residues, wherein $B^b$ may be represented by the structure: $(B^0-B^1-B^2-B^3-B^4-B^5-B^6-B^7-B^8-B^9-B^{10}-B^{11}-B^{12}$; SEQ ID NO:16);

$C^b$ is a central core consisting of from about 3, about 4, about 5, about 6, about 7, about 8, about 9, about 10, about 11, about 12 amino acids; and $D^b$ is a modified C-terminal fragment of intermedin (IMD) comprising of from about 3, about 4, about 5, about 6 amino acid residues with a C-terminal amide, where at least one amino acid of the C-terminal fragment is selected from histidine (His), proline (P), serine (Ser), tyrosine (Tyr).

In some embodiments a pan-specific, CLR/RAMP1-selective, and CLR/RAMP2-selective receptor super-antagonist comprises, consists or consists essentially of:

```
                                          (SEQ ID NO: 77)
Pal-TVQKLAHQIYQFTDKDKDNSAPVDPSSPHSY-NH2

(SEQ ID NO: 78)
miniPEG-K(Pal)VQKLAHQIYQFTDKDKDNSAPVDPSSPHSY-NH2

(SEQ ID NO: 112)
miniPEG-K(Pal)VQKLAHQIYQFTDKDSAPVDPSSPHSY-NH2

(SEQ ID NO: 114)
miniPEG-K(Pal)VQKLAHQIYSAPVDPSSPHSY-NH2

(SEQ ID NO: 119)
Pal-KVQKLAHQIYQFTDKDVAPRSKISPQGY-NH2

(SEQ ID NO: 120)
Pal-KVQNLSHRLWQLMGPAGSAPVDPSSPHSY-NH2

(SEQ ID NO: 121)
Pal-KVQKLAHQIYQFTDKDSAPVDPSSPHSY-NH2

(SEQ ID NO: 122)
Pal-KVQKLAHQIYSAPVDPSSPHSY-NH2

(SEQ ID NO: 123)
Pal-KVQKLAHQISAPVDPSSPHSY-NH2
```

Pal-KVQKLAHQSAPVDPSSPHSY-NH$_2$ (SEQ ID NO: 124)

Pal-KVQKLAHQIYQFTDKSAPVDPSSPHSY-NH$_2$ (SEQ ID NO: 125)

Pal-KVQKLSAPVDPSSPHSY-NH$_2$. (SEQ ID NO: 139)

In some embodiments a CLR/RAMP receptor super-antagonist comprises an amino acid sequence having greater than 60%, greater than 70%, greater than 80%, greater than 90%, greater than 95% sequence identity to the amino acid sequence of SEQ ID NOS: 77-78, 112, 114, 119, 120-125, 139, 140, 142, 145, 146, 148, or 149 wherein said peptide retains antagonist activity. A CLR/RAMP receptor super-antagonist may comprise a stereoisomer, derivative, or peptidomimetics to the amino acid sequence of SEQ ID NOS: 77-78, 112, 114, 119, 120-125, 139, 140, 142, 145, 146, 148, 149, or 190-192.

In some embodiments of the CLR/RAMP receptor super-antagonists having the structure of Formula II, the antagonist comprises a third peptide fragment (db) having 6 amino acid residues or less, wherein said third peptide fragment has a sequence from ADM or IMD. In some embodiments of the CLR/RAMP receptor super-antagonists having the structure of Formula II, the second peptide fragment and the third peptide fragment are contiguous.

In some embodiments of the modified super-antagonist having the structure of Formula II, III or IV the sequence comprises a fragment of an ADM, CGRP or IMD from any of a range of species. In some embodiments, the analogs can have a 60%, 65%, 70%, 75%, 80%, 85%, 90%, or 95% sequence identity with the SEQ ID NOS: 77-78, 112, 114, 119, 120-125, 139, 140, 142, 145, 146, 148, 149, or 190-192.

In some embodiments of a CLR/RAMP receptor super-antagonist having the structure of Formula II: B$^b$ is a modified N-terminal fragment of ADM and IMD peptide family member comprising from four to thirteen amino acid residues; C$^b$ is a central core comprising from three to six amino acid residues; and D$^b$ is a C-terminal fragment of IMD or ADM comprising from three to six amino acid residues with a C-terminal amide, where at least one amino acid of the C-terminal fragment is proline (P), serine (Ser), or tyrosine (Tyr), or pharmaceutically acceptable salt thereof. The length of the B$^b$, C$^b$, and D$^b$ is constrained not by the number of residues per se but by the steric considerations that allow the analogs to interact with a target receptor at the cell membrane surface and at an extracellular domain (i.e., a functional requirement), respectively, in competition with wild type ADM/CGRP/IMD family peptides.

In some embodiments, said CLR/RAMP receptor super-antagonists have a loss of the activation activity of the molecule in interactions with a CLR/RAMP receptor or with a member of the calcitonin/CGRP family of receptors as compared to the wild-type molecule, but may not affect the binding to the receptor. As a result, said CLR/RAMP receptor super-antagonists represent a molecule which can occupy the receptor, but which antagonize rather than activates the signal transduction pathway by making the receptor unavailable for binding by signal-transducing agonists or by repelling the hydrophilicity of ligands.

In some embodiments, super-antagonists have the structure of Formula II, wherein the B$^b$ fragment comprises: (B$^0$-B$^1$-B$^2$-B$^3$-B$^4$-B$^5$-B$^6$-B$^7$-B$^8$-B$^9$-B$^{10}$-B$^{11}$-B$^{12}$, SEQ ID NO: 16), where: B$^0$ can be selected from the group consisting of a natural amino acid or absent; B$^1$, B$^2$, B$^3$, B$^4$, B$^5$, B$^6$, B$^7$, B$^8$, B$^9$, B$^{10}$, B$^{11}$, and B$^{12}$ can be selected from the group consisting of valine (Val), leucine (Leu), alanine (Ala), isoleucine (Ile), cysteine (Cys), serine (Ser), and tyrosine (Tyr), arginine (Arg), asparagine (Asn), aspartic acid (Asp), glutamic acid (Glu), glutamine (Gln), histidine (His), lysine (Lys), and tyrosine (Tyr), phenylalanine (F), or absent.

In some embodiments a super-antagonist has a structure of Formula III:

(III) (SEQ ID NO: 246)

R1-B$^0$-B$^1$-B$^2$-B$^3$-B$^4$-B$^5$-B$^6$-B$^7$-B$^8$-B$^9$-B$^{10}$-B$^{11}$-B$^{12}$-B$^{13}$-

B$^{14}$-B$^{15}$-B$^{16}$-B$^{17}$-B$^{18}$-B$^{19}$-B$^{20}$-B$^{21}$-B$^{22}$-B$^{23}$-B$^{24}$-B$^{25}$ B$^{26}$-

B$^{27}$-B$^{28}$-NH$_2$ where: B$^0$ is selected from the group consisting of an empty residue, acylated histidine (acy-His), acylated arginine (acy-Arg), acylated lysine (acy-Lys), acylated serine (acy-Ser), acylated threonine (acy-Thr), acylated tyrosine (acy-Tyr), acylated aspartic acid (acy-Asp), acylated glutamic acid (acy-Glu), acylated glutamine (acy-Gln), acylated asparagine (acy-Asn); acylated valine (acy-Val), acylated alanine (acy-Ala), acylated glycine (acy-Gly), acylated isoleucine (acy-Ile), acylated leucine (acy-Leu), acylated phenylalanine (acy-Phe), acylated tryptophan (acy-Trp), acylated proline (acy-Pro), acylated methionine (acy-Met), acylated cysteine (acy-Cys), double acylated histidine (acy-His(acy)), ace-histidine(acy) (ace-His(acy)), mini-PEG-acylated-histidine (mini-PEG-His(acy)), double acylated arginine (acy-Arg(acy)), ace-arginine(acy) (ace-Arg(acy)), mini-PEG-acylated-arginine (mini-PEG-Arg(acy)), lysine (Lys), double acylated lysine (acy-Lys(acy)), ace-lysine (acy) (ace-Lys(acy)), and mini-PEG-acylated-lysine (mini-PEG-Lys(acy);

B$^1$ is selected from the group consisting of an empty residue, Val, Ala, Gly, Ile, Cys, and Leu B$^2$ is selected from the group consisting of an empty residue, Gln, Glu, Asp, Cys, and Asn;

B$^3$ is selected from the group consisting of an empty residue, His, Arg, Lys, Gln, Cys, and Asp;

B$^4$ is selected from the group consisting of an empty residue, Val, Ala, Gly, Ile, Cys, and Leu;

B$^5$ is selected from the group consisting of an empty residue, Val, Ala, Gly, Ile, Leu, Ser, Th, Cys, and Tyr;

B$^6$ is selected from the group consisting of an empty residue, His, Arg, Cys, and Lys;

B$^7$ is selected from the group consisting of an empty residue, Gln, and Asn, His, Arg, Cys, and Lys;

B$^8$ is selected from the group consisting of an empty residue, Val, Ala, Gly, Ile, Cys, and Leu;

B$^9$ is selected from the group consisting of an empty residue, Trp, Phe, Ser, Thr, Cys, and Tyr;

B$^{10}$ is selected from the group consisting of an empty residue, Gln, Glu, Asp, Cys, and Asn;

B$^{11}$ is selected from the group consisting of an empty residue, Trp, Phe, Val, Ala, Gly, Ile, Cys, and Leu;

B$^{12}$ is selected from the group consisting of an empty residue, Ser, Thr, and Tyr; Met, Trp, Cys, and Phe;

B$^{13}$ is selected from the group consisting of an empty residue, Gln, Glu, Asp, Asn, Val, Ala, Gly, Ile, Cys, and Leu;

B$^{14}$ is selected from the group consisting of an empty residue, His, Arg, Lys, Val, Ala, Gly, Ile, Leu, Cys, and Pro;

B$^{15}$ is selected from the group consisting of an empty residue, Gln, Glu, Asp, Asn, Val, Ala, Gly, Ile, Cys, and Leu;

B¹⁶ is selected from the group consisting of an empty residue, Val, Ala, Gly, Ile, Cys, and Leu;
B¹⁷ is selected from the group consisting of an empty residue, Ser, Thr, Cys, and Tyr;
B¹⁸ is selected from the group consisting of an empty residue, Val, Ala, Gly, Ile, Cys, and Leu;
B¹⁹ is selected from the group consisting of an empty residue, Val, Ala, Gly, Ile, Leu, Cys, and Pro;
B²⁰ is selected from the group consisting of an empty residue, His, Arg, Lys, Val, Ala, Gly, Ile, Cys, and Leu;
B²¹ is selected from the group consisting of an empty residue, Ser, Thr, Tyr, Gln, Glu, Asp, Cys, and Asn;
B²² is selected from the group consisting of an empty residue, His, Arg, Lys, Val, Ala, Gly, Ile, Leu, Cys, and Pro;
B²³ is selected from the group consisting of an empty residue, Ser, Thr, Tyr, Val, Ala, Gly, Ile, Cys, and Leu;
B²⁴ is selected from the group consisting of an empty residue, Ser, Thr, Cys, and Tyr;
B²⁵ is selected from the group consisting of an empty residue, Val, Ala, Gly, Ile, Leu, Cys, and Pro;
B²⁶ is selected from the group consisting of an empty residue, His, Arg, Lys, Gln, Glu, Asp, Cys, and Asn;
B²⁷ is selected from the group consisting of an empty residue, Val, Ala, Gly, Ile, Leu, Ser, Thr, Cys, and Tyr;
B²⁸ is selected from the group consisting of an empty residue, Ser, Thr, Cys, and Tyr.

A super-antagonist may be provided as a pharmaceutical composition comprising one of super-antagonist peptides. The pharmaceutical composition can be used in a method for treating headache, migraine, arthritis pain, tumor-associated pain, neuropathic pain, endometriosis, morphine tolerance, macular degeneration, tumor angiogenesis, tumor metastasis, or angioedema in an individual, the method comprising administering to an individual an effective amount of a CLR/RAMP receptor super-antagonist. Some embodiments provide a pharmaceutical composition comprising a pharmaceutically acceptable excipient and the super-antagonist as disclosed and described herein.

Some embodiments provide a method of treating a headache or a tumor in an individual, the method comprising administering to the individual an effective amount of the super-antagonist as disclosed and described herein. In some embodiments, the method can further comprise identifying a subject suffering from headache or tumor. In some embodiments, the headache is a migraine.

Some embodiments provide a method of treating a condition associated with aberrant levels of CGRP comprising the administration of the super-antagonist as disclosed and described herein, to an individual, the method comprising administering to the individual an effective amount of a super-antagonist as disclosed and described herein. In some embodiments, the condition is a migraine.

An MRL compound can have the structure of Formula IV, where

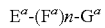   (IV) wherein:

$E^a$ is a ligand of a GPCR;
$F^a$ is a PEG group; n is an integral number from 1 to 200; and
$G^a$ is a CLR/RAMP receptor ligand, comprising the structure of Formula I, II, III, or IV.

In particular $E^a$ can be a ligand of any one of a somatostatin receptor, an apelin receptor, a bradykinin receptor, a neurotensin receptor, or an angiotensin II receptor.

In some embodiments $E^a$ is an agonist of human somatostatin receptors (SSTR1, SSTR2, SSTR3, SSTR4, and SST5). In some embodiments $E^a$ is selected from somatostatin, Octreotide, Octreotate, Lanreotide, Vapreotide, Pasireotide, Dotatate, Cortistatin 14, Cortistatin 17, BIM 23052, CH 275, (1R,1'S,3'R/1R,1'R,3'S)-L-054,264, L-803,087 trifluoroacetate, L-817,818, NNC 26-9100, RC 160, Seglitide, somatostatin-14, somatostatin-28, TC-G 1003, BIM 23056, TT 232, and analogs thereof.

In some embodiments $E^a$ is an agonist of human neurotensin receptor 1 and 2 (NSTR1 and NSTR2). In some embodiments $E^a$ is a neurotensin analog and having the primary sequence Tn-A1-A2-Pro-A4-A5-Leu-Tc where A1 is Arg, Lys or a non-proteinogenic amino acid, A2 is Lys, Asn, Gly, Ile, His, Arg or a non-proteinogenic amino acid, A4 is Trp, Tyr or a non-proteinogenic amino acid, A5 is Phe, Ile or a non-proteinogenic amino acid; TN is an amino terminal portion wherein TN, includes N-acetyl, pyroglutamyl-glycinyl or pGlu-Leu-Tyr-Glu-Asn-Lys-pro, and Tc is a non-amidated carboxyl terminal portion; optionally comprising neurotensin, neurotensin (8-13), N-acetyl-neurotensin (8-13), JMV 449, Kinetensin, Neuromedin N, TC NTR1 17, Xenin 8, and analogs thereof.

In some embodiments $E^a$ is an agonist of a human apelin receptor (APJ receptor or APLNR). In some embodiments $E^a$ comprises a sequence of [Pyr1]-Apelin-13, Apelin-17, Apelin-36, Apela/ELABELA/Toddler, ML 233, and analogs thereof.

In some embodiments $E^a$ is an antagonist of human bradykinin receptor B1 and/or B2 (BDKRB1 and BDKRB2). In some embodiments $E^a$ comprises Icatibant (or HOE 140), MEN 11270, Noscapine hydrochloride, R 715, R 892, WIN 64338 hydrochloride, (D-Arg⁰,Hyp³,Igl⁵,D-Igl⁷,Oic⁸)-Bradykinin, Lys-(Des-Arg⁹,Leu⁸)-Bradykinin, (Des-Arg⁹,Leu⁸)-Bradykinin, (N-Me-D-Phe⁷)-Bradykinin, (1-Adamantaneacetyl-D-Arg⁰, Hyp³,β-(2-thienyl)-Ala⁵,⁸,D-Phe⁷)-Bradykinin, Lys-Lys-(Hyp³,β-(2-thienyl)-Ala⁵,⁸,D-Phe⁷)-Bradykinin, and analogs thereof.

In some embodiments $E^a$ is an antagonist of a human type 1 angiotensin II receptor (AGTR1). In some embodiments $E^a$ comprises saralasin, sarilesin, sarthran, losartan, irbesartan, olmesartan, candesartan, valsartan, fimasartan, eprosartan, telmisartan, azilsartan, and analogs thereof.

General Peptide Modification

In some embodiments, one or more residues, acylation, and pegylation are fused N-terminally to $B^b$ of the agonist in formula I and antagonist in formula II and III as well as the N-terminus of the CLR/RAMP receptor ligand components of the MRLs. In some embodiments this extension affects the bioactivity and stability of the agonist, the antagonist, or the MRL after administration. In some embodiments, the modification is a combination of one or more amino acid residues, PEG moieties and fatty acids, for example a functional group comprising a structure of Formula (W')(X')n(Y')n'(Z')n" as defined above. Examples of this modification include, but are not limited to, hexadecanoyl-isoGlu-PEG3, hexadecanoyl-isoGlu-PEG3-PEG3, hexadecanoyl-PEG3-isoGlu, [19-carboxy-nonadecanoyl]-isoGlu, [19-carboxy-nonadecanoyl]-PEGS-isoGlu, [19-carboxy-nonadecanoyl]-isoGlu-Peg3-Peg3, [17-carboxy-heptadecanoyl]-isoGlu-Peg3-Peg3, [19-carboxy-nonadecanoyl]-isoGlu-PEG3, [19-carboxy-nonadecanoyl]-isoGlu-PEG3.

In some embodiments, addition of residues N-terminal or C-terminal to $B^b$ of the agonist or antagonist, for example, an XTENS sequence comprising Ala, Glu, Gly, Pro, Ser and Thr (SEQ ID NO:247), may extend the stability of the analog (Schellenberger et al., 2009, Nature Biotechnology 27 (12): 1186-1192). In some embodiments the addition of residues N-terminal or C-terminal may increase the half-life of an administered drug. These changes are contemplated herein; a person having ordinary skill in the art will know how this can be done.

Some embodiments provide a method of identifying a CLR/RAMP receptor binding ligand by providing the super-antagonist bound to a CLR/RAMP receptor, providing a test compound or library of test compounds, and identifying compounds which are capable of dissociating the super-antagonist from the CLR/RAMP receptor. Such compounds identified by this method may be further screened against other CLR/RAMP receptor binding agents to identify selective CLR/RAMP receptor binding ligands.

In some embodiments of the invention a CLR/RAMP receptor superagonist, a CLR/RAMP receptor super-antagonist, or an MRL is provided in which the peptide comprises, consists or consists essentially of an amino acid sequence having at least 60%, at least 70%, at least 80%, at least 90%, at least 95% or more sequence identity to the amino acid sequence of SEQ ID NOS: 28-51, 69-70, 77-78, 92, 94, 101, 103, 110, 112, 114, 119, 120-125, 139, 140, 142, 145-159, 190-192, 210, 211, 213, 214, 218, 223, 224, 228, 231, and 234, wherein said peptide retains agonist or antagonist activity.

Also provided are therapeutic agents, e.g. drugs, therapeutic polypeptides, etc. that are linked to a CLR/RAMP receptor superagonist or super-antagonist of the invention, where the CLR/RAMP receptor superagonist or super-antagonist acts as a targeting moiety for the therapeutic agent. Also provided are methods of delivering the therapeutic agent linked to a CLR/RAMP receptor superagonist or super-antagonist of the invention, the method comprising administering an effective dose of the linked therapeutic agent to an individual in need thereof. In some embodiments, the therapeutic agent is an imaging agent, a toxin, or a chemotherapeutic agent. Labeled CLR/RAMP receptor ligand (e.g., adrenomedullin derivatives) for use as imaging and also therapeutic agent is described by J. Depuis et al. in CA 2567478 and WO 2008/138141). In these ADM derivatives a complexating cage like molecular structure capable of binding radioactive isotopes was attached to the N terminus of ADM in a direct manner or via a spacer unit potentially also including short PEG spacers. The diagnostic or therapeutic value of theses drugs arises from the targeted delivery of the radioactive molecule.

Some embodiments provide a method of identifying a CLR/RAMP receptor by providing a CLR/RAMP receptor superagonist or super-antagonist bound to a CLR/RAMP receptor, providing a test compound or library of test compounds, and for imaging CLR/RAMP receptors in vivo.

In some embodiments, a heterologous moiety is linked to the superagonist or super-antagonist. In some embodiments the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. The skilled person is aware that an amino acid polymer also may form random coil conformation when residues other than alanine, serine, and proline are added as a minor constituent in the PAS sequence. The amino acids different from alanine, serine and proline may be selected from the group consisting of Arg, Asn, Asp, Cys, Gln, Glu, Gly, His, He, Leu, Lys, Met, Phe, Thr, Trp, Tyr, and Val. Under physiological conditions, the PAS sequence stretch forms a random coil conformation and thereby can mediate an increased in vivo and/or in vitro stability. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which could provide advantages over synthetic polymers such as PEG.

Non-limiting examples of the PAS sequences forming random coil conformation comprise an amino acid sequence selected from the group consisting of ASPAAPA-PASPAAPAPSAPA, AAPASPAPAAPSAPAPAAPS, and AS AAAP AAAS AAAS AP S AAA, or any combinations thereof (see US Pat. Publ. No. 2010/0292130 A1 and PCT Appl. Publ. No. WO 2008/155134 A1).

In certain embodiments, a heterologous moiety that is linked to the superagonist or super-antagonist is hydroxyethyl starch (HES) or a derivative thereof. HES is a derivative of naturally occurring amylopectin and is degraded by alpha amylase in the body, and exhibits advantageous biological properties. It is used as a blood volume replacement agent and in hemodilution therapy in the clinics (Sommermeyer et al., Krankenhauspharmazie, 8, 271-278 (1987); and Weidler et al, (1991) Arzneim. Forschung/Drug Res. 41:494-498).

In certain embodiments, a heterologous moiety linked to the superagonist or super-antagonist is a mixture of hydroxyethyl starches having different mean molecular weights and/or different degrees of substitution and/or different ratios of C2: C6 substitution.

In certain embodiments, a heterologous moiety that is linked to the superagonist or super-antagonist is a polysialic acid (PSAs) or a derivative thereof. PSAs are naturally occurring unbranched polymers of sialic acid produced by certain bacterial strains and in mammals in certain cells (Roth J., et al. (1993) in Polysialic Acid: From Microbes to Man, eds Roth J., Rutishauser U., Troy F. A. (Birkhauser Verlag, Basel, Switzerland), pp 335-348). Sialic acid may also be found in alternating copolymers with monomers other than sialic acid. Polysialic acids have important biological functions including the evasion of the immune and complement systems by pathogenic bacteria and the regulation of glial adhesiveness of immature neurons during fetal development (wherein the polymer has an anti-adhesive function; Cho and Troy, PNAS, USA, (1994) 91:11427-11431). Various methods of attaching or conjugating polysialic acids to a peptide or polypeptide have been described (see U.S. Pat. No. 5,846,951; WO-A-0187922, and US 2007/0191597 A1).

In certain embodiments, the heterologous moiety that is linked to the superagonist or super-antagonist is a glycine-rich homo-amino-acid polymer (HAP). The HAP sequence can comprise a repetitive sequence of glycine, which has at least 50 amino acids, at least 100 amino acids, 200 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)n (SEQ ID NO:242), (Gly4Ser)n (SEQ ID NO:243) or S(Gly4Ser)n (SEQ ID NO:244), wherein n is 1-200.

In certain aspects, a compound of the invention is covalently linked to at least one heterologous moiety that is or comprises an XTEN polypeptide or fragment, variant, or derivative thereof. As used here "XTEN polypeptide" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

In certain aspects, an XTEN moiety can increase pharmacokinetic properties such as longer in vivo half-life or increased area under the curve (AUC), so that a compound or conjugate of the invention stays in vivo for an increased period of time compared to a compound or conjugate with the same but without the XTEN heterologous moiety (See International Patent Publication Nos. WO 2010091122 A1, WO 2010144502 A2, WO 2010144508 A1, WO 2011028228 A1, WO 2011028229 A1, or WO 2011028344 A2).

Within the meaning of the present invention, the term "Fc" is to be understood as immunoglobulin constant region or a portion thereof, such as an Fc region or a FcRn binding partner. In certain embodiments, the compound or conjugate is linked to one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region in a biologically active peptide derivative of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

An Fc in a biologically active peptide derivative of the invention can include, for example, a change (e.g., a substitution) at one or more of the amino acid positions disclosed in Intl PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; U.S. Pat. Publ. Nos. US US2007/0237766, US2007/0237767, US2007/0243188, US2007/0248603, US2007/0286859, US2008/0057056. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

An Fc region used in the invention may also comprise an art recognized amino acid substitution which alters its glycosylation. For example, the Fc has a mutation leading to reduced glycosylation (e.g., N- or O-linked glycosylation) or may comprise an altered glycoform of the wild-type Fc moiety (e.g., a low fucose or fucose-free glycan). In certain embodiments, the compound or conjugate of the invention is linked to a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481 A1, 2008/0261877 A1, or 2008/0153751 A1 or PCT Appl. Publ. Nos. 2008/033413 A2, 2009/058322 A1, or 2007/021494 A2.

In one embodiment, the heterologous moiety is albumin, a fragment, or a variant thereof which is further linked to a heterologous moiety selected from the group consisting of an immunoglobulin constant region or portion thereof (e.g., an Fc region), a PAS sequence, HES, and PEG.

In certain embodiments, the heterologous moiety is an albumin binding moiety, which comprises an albumin binding peptide, a bacterial albumin binding domain, an albumin-binding antibody fragment, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) J. Immunol. Methods 218:73-83). Other examples of albumin binding peptides that can be used as conjugation partner are, for instance, those as described in US patent application 2003/0069395 or Dennis et al. (2002) J. Biol. Chem. 277: 35035-35043). Examples of albumin-binding peptides include a series of peptides having the core sequence DICLPRWGCLW (SEQ ID NO:245) (See, Dennis et al, (2002) J. Biol. Chem 277:35035-35043). Albumin-binding antibody fragments are disclosed in Muller and Kontermann, Curr. Opin. Mol. Ther. (2007) 9:319-326, and Holt et al, (2008) Prot. Eng. Design Sci., 21:283-288.

The described superagonist, super-antagonist, and MRL may exist in a cyclized form with an intramolecular disulfide bond between the thiol groups of additional cysteines. Other embodiments include analogs of these disulfide derivatives in which one of the sulfurs has been replaced by a C3/4 group or other isostere for sulfur. The described superagonist, and super-antagonist, and MRL may exist in a cyclized form with lactam bridges or inter-side chain linkages between the side chain of any pair of amino acids. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an oc-haloacetic acid, for example, oc-chloroacetic acid, oc-bromoacetic acid, or oc-iodoacetic acid. The peptides of the present embodiments can be cyclized or dimerized via displacement of the leaving group by the sulfur of the cysteine or homocysteine residue. See, for example, Andreu, et al. (1994) Meth. Mol. Bio. 35:91-169; Barker, et al. (1992) Med. Chem. 35:2040-2048; and Or, et al. (1991) Org. Chem. 56:3146-3149).

According to an embodiment of the present invention, the compounds of formula (I)-(V) can be further modified by N-methylation or acetylation of at least one amide bond. The influence of N-methylation on the metabolic stability of peptides has been described for various peptides. For example, cyclosporine is a naturally occurring, cyclic, multiply N-methylated peptide that exhibits an excellent pharmacokinetic profile. N-methylation in general blocks enzymatic degradation—by proteases as they are unable to cleave N-methylated peptide bonds. Multiple N-methylation was shown to improve the metabolic stability and intestinal permeability of peptides [Chatterjee J, Gilon C, Hoffman A, Kessler H, (2008)N-methylation of peptides: a new perspective in medicinal chemistry, Acc Chem Res., 41:1331-1342]. Cyclization combined with Af-methylation was used to modulate physicochemical properties of peptides, including metabolic stability, membrane permeability and oral bioavailability [Chatterjee J, Laufer B, Kessler H, (20120) Synthesis of Af-methylated cyclic peptides, Nat Protoc, 7:432-444]. Dong Q G et al. (2012; Improvement of enzymatic stability and intestinal permeability of deuterohemin-peptide conjugates by specific multi-site Af-methylation, Amino Acids. 43:2431-2441) describe that Af-Methylation at selected sites showed high resistance against proteolytic degradation. In diluted serum and intestinal preparation 50- to 140-fold higher half-life values were observed. In addition, Linde Y et al. (2008; Biopolymers 90:671-682) describe that cyclic Af-methylated analogues of the a-melanocyte stimulating hormone were more stable, however less biologically active than the parent peptide. It will be understood that two or more such modifications can be coupled in one peptidomimetic structure.

In some embodiments, the modified peptide agonists, antagonists, or MRLs as disclosed and described herein may also represent a prodrug: a prodrug is any compound that undergoes biotransformation before exhibiting its pharmacological effects. Prodrugs could also include a carrier-linked prodrug, a cascade prodrug.

Methods of Use

The present invention further provides a method for treatment and/or prevention of disorders, in particular the disorders mentioned above, using an active amount of the compounds according to the invention, including without limitation endothelial, cardiovascular, metabolic, pulmonary, lymphatic, renal, neuronal, nociceptive, cutaneous, edematous and/or inflammatory disorders. Some embodiments provide a method of treating a condition associated with aberrant levels of CGRP, ADM, IMD, somatostatins, neurotensins, apelin, bradykinin, and/or angiotensin II comprising the administration of the CLR/RAMP receptor super-agonists, super-antagonists, or MRLs as disclosed and described herein, to an individual, the method comprising administering to the individual an effective amount of a CLR/RAMP receptor superagonist, a CLR/RAMP receptor super-antagonist, or an MRL as disclosed and described herein.

For the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing, a disease, disorder, condition, or state, the development and/or progression thereof, and/or the symptoms thereof. The term prevention includes prophylaxis. Treatment or prevention of a disease, disorder, condition, or state may be partial or complete.

In light of the pharmacologic activities of CLR/RAMP receptor agonists, CLR/RAMP receptor antagonists, and MRLs, numerous clinical indications are evident, and include without limitation hypertension, for example pregnancy hypertension; preeclampsia; eclampsia; resistant hypertension, refractory hypertension, hypertensive crisis, malignant hypertension, pulmonary arterial hypertension, intradialysis hypertension, hypertension associated with diabetes, etc.; heart failure, stroke, myocardial infarction; cardiac hypertrophy; osteoarthritis; bronchopulmonary dysplasia (BPD); chronic obstructive pulmonary disease (COPD); emphysema; lung fibrosis; ulcerative colitis; wound healing; diabetic ulcer; lymphedema; rheumatoid arthritis; neuroprotection; tumor growth; tumor angiogenesis; tumor metastasis and the like as well as for the treatment or prevention of pain including, for example, bone and joint pain (osteoarthritis), repetitive motion pain, dental pain, pain associated with cancer, myofascial pain (muscular injury, fibromyalgia), perioperative pain (general surgery, gynecological), inflammatory pain such as inflammatory airways disease (chronic obstructive pulmonary disease), and chronic pain such as migraine headache. These compounds may also be used subsequent to surgical intervention (e.g. as post-operative analgesics) and to treat inflammatory pain of varied origins (e.g. osteoarthritis, rheumatoid arthritis, rheumatic disease, tenosynovitis, wounds and gout), as well as for the treatment of pain associated with angina, menstruation, or cancer. For example, clinical indications for which a superagonist of the invention may find use include particularly the treatment of malignant hypertension. The peptides of the invention provide for a decrease in blood pressure, e.g. systolic pressure of at least about 5%, at least about 10%, at least about 15%, at least about 20% or more.

In methods of use, an effective dose of a peptide of the invention is administered alone or in a cocktail of peptides, or combined with additional active agents for the treatment of a condition as listed above. The effective dose may be from about 1 ng/kg weight, 10 ng/kg weight, 100 ng/kg weight, 1 µg/kg weight, 10 µg/kg weight, 25 µg/kg weight, 50 µg/kg weight, 100 µg/kg weight, 250 µg/kg weight, 500 µg/kg weight, 750 µg/kg weight, 1 mg/kg weight, 5 mg/kg weight, 10 mg/kg weight, 25 mg/kg weight, 50 mg/kg weight, 75 mg/kg weight, 100 mg/kg weight, 250 mg/kg weight, 500 mg/kg weight, 750 mg/kg weight, and the like. The dosage may be administered multiple times as needed, e.g. every 30 minutes, every hour, every 2 hours, every 4 hours, every 6 hours, every 8 hours, every 12 hours, every 18 hours, daily, every 2 days, every 3 days, weekly, and the like. The dosage may also be administered as a continuous infusion, e.g. in acute treatment methods.

The peptides of the invention find use in reducing hypertension associated with preeclampsia and eclampsia, resistant hypertension, intradialysis hypertension and may be administered for a period of time sufficient to stabilize the subject and allow for safe delivery of the pregnancy.

Preeclampsia is new-onset hypertension and proteinuria after 20 wk gestation. Eclampsia is unexplained generalized seizures in patients with preeclampsia. Diagnosis is clinical and by urine protein measurement. Conventional treatment is usually with IV Mg sulfate and delivery at term. Preeclampsia affects 3 to 7% of pregnant women. Preeclampsia and eclampsia develop after 20 wk gestation; up to 25% of cases develop postpartum, most often within the first 4 days but sometimes up to 6 wk postpartum. Untreated preeclampsia usually smolders for a variable time, then suddenly progresses to eclampsia, which occurs in 1/200 patients with preeclampsia. Untreated eclampsia is usually fatal.

Preeclampsia may be asymptomatic or may cause edema or excessive weight gain. Nondependent edema, such as facial or hand swelling (the patient's ring may no longer fit her finger), is more specific than dependent edema. Reflex reactivity may be increased, indicating neuromuscular irritability, which can progress to seizures (eclampsia). Petechiae may develop, as may other signs of coagulopathy.

Diagnosis is of new-onset hypertension (BP>140/90 mm Hg) plus new unexplained proteinuria>300 mg/24 h after 20 wk. Diagnosis is suggested by symptoms or presence of hypertension, defined as systolic BP>140 mm Hg, diastolic BP>90 mm Hg, or both. Except in emergencies, hypertension should be documented in >2 measurements taken at least 4 h apart. Urine protein excretion is measured in a 24-h collection. Proteinuria is defined as >300 mg/24 h. Alternatively, proteinuria is diagnosed based on a protein:creatinine ratio 0.3 or a dipstick reading of 1+(used only if other quantitative methods are not available). Absence of proteinuria on less accurate tests (eg, urine dipstick testing, routine urinalysis) does not rule out preeclampsia.

In the absence of proteinuria, preeclampsia is also diagnosed if pregnant women have new-onset hypertension plus new onset of any of the following: Thrombocytopenia (platelets<100,000/μL); Renal insufficiency (serum creatinine>1.1 mg/dL or doubling of serum creatinine in women without renal disease), Impaired liver function (aminotransferases>2 times normal), Pulmonary edema, Cerebral or visual symptoms.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure, especially those with resistant hypertension or chronic kidney diseases, or those require routine hemodialysis. The subject peptides may be administered to reduce arterial blood pressure. In addition, a secondary effect of reducing hypertension is reduction of edema and inflammatory exudate volume.

Pharmaceutical compositions containing peptides of the invention are useful as cardioprotective agents, e.g. to ameliorate ischemic injury or myocardial infarct size consequent to myocardial ischemia. The development of new therapeutic agents capable of limiting the extent of myocardial injury, i.e., the extent of myocardial infarction, following acute myocardial ischemia is a major concern of modern cardiology. There has also been interest in the development of therapies capable of providing additional myocardial, renal, neuronal, and vascular protection which could be administered in conjunction with thrombolytic therapy, or alone, since retrospective epidemiological studies have shown that mortality during the first few years following infarction appears to be related to original infarct size.

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

The compounds of this invention can be normally administered parenterally, in the treatment of patients in need of cardioprotective therapy. The dosage regimen is that which insures maximum therapeutic response until improvement is obtained and thereafter the minimum effective level that gives relief. Thus, in general, the dosages are those that are therapeutically effective in producing a cardioprotective or vasoprotective effect, i.e., amelioration of ischemic injury or myocardial infarct size consequent to myocardial ischemia. It is also anticipated that the peptides would be useful as an injectable dosage form which may be administered in an emergency to a patient suffering from myocardial ischemia, etc.

The peptides of the invention also find use in the reduction of edema, for example in lymphedema, rheumatoid arthritis, edema secondary to brain tumors or irradiation for cancer, edema resulting from stroke, head trauma or spinal cord injury, post-surgical edema, hemodialysis, asthma and other respiratory diseases and cystoid macular edema of the eye.

On the basis of their pharmacological properties, the compounds according to the invention can be employed for treatment and/or prevention of cardiovascular diseases, in particular heart failure, especially chronic and acute heart failure, worsening heart failure, diastolic and systolic (congestive) heart failure, acute decompensated heart failure, cardiac insufficiency, coronary heart disease, angina pectoris, myocardial infarction, ischemia reperfusion injury, ischemic and hemorrhagic stroke, arteriosclerosis, atherosclerosis, hypertension, especially essential hypertension, malignant essential hypertension, secondary hypertension, renovascular hypertension and hypertension secondary to renal and endocrine disorders, hypertensive heart disease, hypertensive renal disease, pulmonary hypertension, especially secondary pulmonary hypertension, pulmonary hypertension following pulmonary embolism with and without acute corpulmonale, primary pulmonary hypertension, resistant hypertension, refractory hypertension, intradialysis hypertension, hypertensive crisis, ulcerative colitis, and peripheral arterial occlusive disease.

The compounds according to the invention are furthermore suitable for treatment and/or prevention of pulmonary disorders, such as chronic obstructive pulmonary disease, asthma, acute and chronic pulmonary edema, allergic alveolitis and pneumonitis due to inhaled organic dust and particles of fungal, actinomycetic or other origin, acute chemical bronchitis, acute and chronic chemical pulmonary edema, neurogenic pulmonary edema, acute and chronic pulmonary manifestations due to radiation, acute and chronic interstitial lung disorders, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS or acute pulmonary insufficiency following surgery, trauma or burns, ventilator induced lung injury (VILI), pulmonary fibrosis, and mountain sickness.

The compounds according to the invention are furthermore suitable for treatment and/or prevention of gestational [pregnancy-induced] edema and proteinuria with and without hypertension (pre-eclampsia and eclampsia).

The compounds according to the invention are furthermore suitable for treatment and/or prevention of chronic kidney diseases, renal insufficiency, diabetic nephropathy, hypertensive chronic kidney disease, glomerulonephritis, rapidly progressive and chronic nephritic syndrome, unspecific nephritic syndrome, nephrotic syndrome, hereditary nephropathies, acute and chronic tubulo-interstitial nephritis, acute kidney injury, acute kidney failure, traumatic and post procedural kidney injury, cardiorenal syndrome, and protection and functional improvement of kidney transplants.

The compounds are moreover suitable for treatment and/or prevention of diabetes mellitus and its consecutive symptoms, such as e.g. diabetic macro- and microangiopathy, diabetic ulcer, diabetic nephropathy and neuropathy.

The compounds according to the invention can be used for treatment and/or prevention of disorders of the central and peripheral nervous system such as migraine, cluster headache, epilepsy, stroke, vasospasm, viral and bacterial meningitis and encephalitis (e.g. Zoster encephalitis), traumatic and toxic brain injury, primary or secondary malignant neoplasm of the brain and spinal cord, radiculitis and polyradiculitis, Guillain-Barre syndrome [acute or post-infective polyneuritis, Miller Fisher Syndrome], Parkinson's disease, acute and chronic polyneuropathies, pain, cerebral edema, Alzheimer's disease, degenerative diseases of the nervous system and demyelinating diseases of the central nervous system such as but not restricted to multiple sclerosis.

The compounds according to the invention are furthermore suitable for treatment and/or prevention of portal hypertension and liver fibrosis [cirrhosis] and its sequelae such as esophageal varices and ascites, for the treatment and/or prevention of pleural effusions secondary to malignancies or inflammations and for the treatment and/or prevention of primary and secondary lymphedema and of edema secondary to varices.

The compounds according to the invention are furthermore suitable for treatment and/or prevention of neuropathic pain selected from incision pain, postoperative pain, surgical wound pain, neuroma, osteoarthritic, arthritis joint, low back, posttraumatic, diabetic neuropathy, and bone and joint pain, repetitive motion pain, dental pain, pain associated with cancer, myofascial pain (muscular injury, fibromyalgia), perioperative pain (general surgery, gynecological), inflammatory pain such as inflammatory airways disease (chronic obstructive pulmonary disease), and chronic pain such as migraine headache. The compounds according to the invention are furthermore suitable for treatment and/or prevention of inflammatory disorders of the gastrointestinal tract such as inflammatory bowel disease, Crohn's disease, ulcerative colitis, and toxic and vascular disorders of the intestine. The compounds according to the invention are furthermore suitable for treatment and/or prevention of sepsis, hemorrhagic shock, or multi organ failure (MOF), traumatic shock, and angioneurotic edema [Giant urticaria, Quincke's edema].

The compounds according to the invention are furthermore suitable for treatment of edematous ocular disorders or ocular disorders associated with disturbed vascular function, including, but not being limited to, age-related macular degeneration (AMD), diabetic retinopathy, in particular diabetic macula edema (DME), subretinal edema, and intraretinal edema. In the context of the present invention, the term age-related macular degeneration (AMD) encompasses both wet (or exudative, neovascular) and dry (or non-exudative, non-neovascular) manifestations of AMD. The compounds according to the invention are furthermore suitable for treatment of ocular hypertension (glaucoma).

The compounds according to the invention can moreover be used for treatment and/or prevention of operation-related states of ischemia and consecutive symptoms thereof after surgical interventions, in particular interventions on the heart using a heart-lung machine, interventions on the carotid arteries, aorta, or with instrumental opening or penetration of the skull cap. The compounds are furthermore suitable for general treatment and/or prevention in the event of surgical interventions with the aim of accelerating wound healing and shortening the reconvalescence time. They are further suited for the promotion of wound healing.

The compounds are furthermore suitable for treatment and/or prevention of disorders of bone density and structure such as but not restricted to osteoporosis, osteomalacia and hyperparathyroidism-related bone disorders.

The present invention further provides for the use of the compounds according to the invention for preparing a medicament for treatment and/or prevention of disorders, in particular the disorders mentioned above.

Another embodiment of the present invention also features a method for treating or inhibiting the progression of CLR/RAMP and another GPCR-mediated conditions, diseases, or disorders, said method comprising administering to a patient in need of treatment a pharmaceutically effective amount of at least one superagonist, super-antagonist, or an MRL.

The compounds of the present invention can be widely combined with other pharmacologically active compounds, such as antihypertensives, nephroprotectives, diuretics, antidiabetics, lipid-lowering agents, cardioprotective agents, renoprotective agents, antiangiogenic therapeutics, anti-cancer treatments, anti-edema therapeutics, antinociceptive and pain treatment, and wound healing agents. The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

The invention further provides medicaments comprising a compound according to the invention and one or more further active ingredients, in particular for treatment and/or prevention of the disorders mentioned above. Exemplary and preferred active ingredient combinations are:

ACE inhibitors, angiotensin receptor antagonists, beta-2 receptor agonists, phosphodiesterase inhibitors, glucocorticoid receptor agonists, diuretics, or angiotensin converting enzyme-2 or acetylsalicylic acid (aspirin). In a preferred embodiment of the invention, the compounds according to the invention are administered in combination with an ACE inhibitor, such as, by way of example and preferably, enalapril, quinapril, captopril, lisinopril, ramipril, delapril, fosinopril, perindopril, cilazapril, imidapril, benazepril, moexipril, spirapril or trandopril. In a preferred embodiment of the invention, the compounds according to the invention are administered in combination with an angiotensin receptor antagonist, such as, by way of example and preferably, losartan, candesartan, valsartan, telmisartan or embusartan.

In an embodiment of the invention, the compounds according to the invention are administered in combination with a beta-2 receptor agonist, such as, by way of example and preferably, salbutamol, pirbuterol, salmeterol, terbutalin, fenoterol, tulobuterol, clenbuterol, reproterol or formoterol.

In an embodiment of the invention, the compounds according to the invention are administered in combination with a phosphodiesterase (PDE) inhibitor, such as, by way of example and preferably, milrinone, amrinone, pimobendan, cilostazol, sildenafil, vardenafil or tadalafil.

In an embodiment of the invention, the compounds according to the invention are administered in combination with a glucocorticoid receptor agonist, such as, by way of example and preferably, cortisol, cortisone, hydrocortisone, prednisone, methyl-prednisolone, prednylidene, deflazacort, fluocortolone, triamcinolone, dexamethasone or betamethasone.

In an embodiment of the invention, the compounds according to the invention are administered in combination with diuretics, such as, by way of example and preferably, furosemide, torasemide and hydrochlorothiazide.

In an embodiment of the invention, the compounds according to the invention are administered in combination with natriuretic peptides, such as nesiritide (human B-type natriuretic peptide (hBNP)) and carperitide (alpha-human atrial natriuretic polypeptide (hANP)).

In an embodiment of the invention, the compounds according to the invention are administered in combination with urodilatin, a derivative of ANP still under development for acute heart failure.

In an embodiment of the invention, the compounds according to the invention are administered in combination with LCZ696 (Entresto), a neprilysin (enkephalinase, neutral endopeptidase, NEP, also involved in the metabolism of ADM) inhibitor.

In an embodiment of the invention, the compounds according to the invention is used to stimulate the propagation of endothelial or lymphendothelial cell from humans or animals in vitro or in vivo. Endothelial dysfunction is a leading cause of micro and macrovascular complications in a variety of life-threatening diseases, including atherosclerosis, cardiomyopathy, stoke, resistant hypertension, preeclampsia, pulmonary arterial hypertension, and diabetic ulcers. Endothelial dysfunction represents an early event along the natural course of these diseases. The function of vascular endothelium includes the synthesis of substances that modulate vascular tone, the inhibition of platelet aggregation, and control of proliferation of vascular cells. Damage to the endothelium can lead to increased endothelium-derived contracting factors, reduced nitric oxide production, and breakdown of endothelial barriers, leading to hypertension, atherosclerosis, thrombosis, inflammation, vascular resistance, vascular leakage, edema, and functional impairment in many organs. Because of this there has been a significant interest in finding methods to ameliorate endothelial dysfunction. In the last decades, the development of several classes of antihypertensive and vasoprotective drugs including, angiotensin converting enzyme (ACE) inhibitors, angiotensin-receptor antagonists (ARBs), mineralocorticoid receptor antagonists, beta-blockers, diuretics, and calcium channel antagonists, has dramatically improved the outcomes of patients with some of the endothelial dysfunction-associated diseases by reducing oxidative stress, endothelin activity, plasminogen activator activity, or platelet activation. In addition, statins and anti-diabetes drug metformin, and inhibitor of xanthine oxidase such as allopurinol have been shown to improve endothelial functions in patients. However, the progression of many of the endothelial dysfunction-associated diseases cannot be prevented by existing drugs, which were mainly developed to block signaling processes, not to actively improve endothelial functions. The present invention can be used applied to prevent or treat endothelial dysfunction in a variety of diseases, and to facilitate efficient propagation of endothelial cells, which can be applied for the treatment of endothelial dysfunction in its own right.

Formulations

Formulations and medicaments are provided that comprise at least one compound according to the invention, normally together with one or more inert, nontoxic, pharmaceutically suitable excipients and to the use thereof for the aforementioned purposes. For this purpose, they can be administered in a suitable way, for example by the parenteral, pulmonary, nasal, sublingual, lingual, buccal, dermal, transdermal, conjunctival, optic route or as implant or stent. The active agent can be a single peptide disclosed herein; or may be formulated as a cocktail of one or more peptides, e.g. 1, 2, 3, 4, 5, 6, 7 8, 9, 10 or more different peptides, e.g. a peptide comprising, consisting or consisting essentially of the structure of a peptide sequence of Table 1; or comprising, consisting or consisting essentially of an amino acid sequence having at least 60%, at least 70%, at least 80%, at least 90%, at least 95% or more sequence identity to the amino acid sequence of SEQ ID NOS: 28-51, 69-70, 77-78, 92, 94, 101, 103, 110, 112, 114, 119, 120-125, 139, 140, 142, 145-159, 190-192, 210, 211, 213, 214, 218, 223, 224, 228, 231, and 234 wherein said peptide retains agonistic, antagonistic or MRL activity. The peptide may be provided as a pharmaceutical acceptable salt.

Some embodiments include pharmaceutical compositions comprising, as an active ingredient, at least one of the instant modified peptides (also D-amino acid or other peptidomimetics) disclosed herein in association with a pharmaceutical carrier or diluent. These pharmaceutical compositions can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, topical, intranasal or sublingual routes of administration and can be formulated in dosage forms appropriate for each route of administration. The compounds can also be administered in sustained or controlled release dosage forms, including without limitation, depot injections, osmotic pumps, transdermal (including electrotransport and microneedle) patches, and the like, for prolonged and/or timed, localized, pulsed administration at a predetermined rate.

The pharmaceutical compositions of the present embodiments may be manufactured in a manner that is itself known, e.g., by means of conventional mixing, dissolving, granulating, dragee-making, levigating, emulsifying, encapsulating, entrapping or tabletting processes. Pharmaceutical compositions for use in accordance with the present embodiments thus may be formulated in conventional manner using one or more physiologically acceptable carriers comprising excipients and auxiliaries which facilitate processing of the active compounds into preparations which can be used pharmaceutically. Any of the well-known techniques, carriers, and excipients may be used as suitable and as understood in the art.

Injectables can be prepared in conventional forms, either as liquid solutions or suspensions, solid forms suitable for solution or suspension in liquid prior to injection, or as emulsions. Suitable excipients are, for example, water, saline, acetate, citrate, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal and transdermal administration, microneedle patches consist of peptide(s) of the present invention, or penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For administration by inhalation, the instant compounds for use according to the present embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. As an example, preparations for administration by inhalation may be prepared according to the teaching of Quay, et al., U.S. Pat. No. 7,812,120 B2

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum; ophthalmic ointments; ophthalmic suspensions, such as microparticulates, drug-containing small polymeric particles that are suspended in a liquid carrier medium, lipid-soluble formulations; and ocular inserts. Such suitable pharmaceutical formulations are most often and preferably formulated to be sterile, isotonic and buffered for stability and comfort. Pharmaceutical compositions for intranasal delivery may also include drops and sprays often prepared to simulate in, many respects nasal secretions to ensure maintenance of normal ciliary action, such compositions include, for example and without limitation, the nasal solutions disclosed by Azria, et al., in U.S. Pat. No. 5,733,569. Pharmaceutical formulations for intraauricular delivery include suspensions and ointments for topical application in the ear. Common solvents for such aural formulations include glycerin and water.

In addition to the formulations described previously, the instant compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil or a slow-release poly(lactic-co-glycolic acid)(PLGA) microsphere/nanoparticle) or ion exchange resins, or as sparingly soluble derivatives, for example, as a sparingly soluble salt.

Non-limiting examples of methods of administration include, among others, (a) administration though non-oral pathways such as intraocular, intranasal or intraauricular, which administration includes administration as an aqueous suspension, an oily preparation or the like or as a drip, spray, salve, ointment or the like; (b) administration via injection, subcutaneously, intraperitoneally, intravenously, intramuscularly, intradermally, intraorbitally or the like, including infusion pump delivery; (c) administration locally such as by injection directly intracranially, e.g., by depot implantation; as well as (e) administration topically; as deemed appropriate by those of skill in the art for bringing the peptide of the present embodiments into contact with living tissue.

The exact formulation, route of administration and dosage for the pharmaceutical compositions of the present embodiments can be chosen by the individual physician in view of the patient's condition. Typically, the dose range of the composition administered to the patient can be from about 0.000001 to 100 mg/kg of the patient's body weight. The dosage may be a single one or a series of two or more given in the course of one or more days, as is needed by the patient. In instances where human dosages for compounds have been established for at least some condition, the present embodiments will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an intravenous, subcutaneous, or intramuscular dose of each active ingredient at an exemplary range of between 0.001 mg and 100 mg, or an exemplary range of between 0.005 mg and 5 mg. In cases of administration of a pharmaceutically acceptable salt, dosages may be calculated as the free base. In some embodiments, the composition is administered 0.1 to 4 times per day or as a single acute dose, for example to ameliorate hypertension. Alternatively the compositions as described herein may be administered by continuous intravenous infusion, preferably at a dose of each active ingredient up to 1000 mg per day. As will be understood by those of skill in the art, in certain situations it may be necessary to administer the peptides disclosed herein in amounts that exceed, or even far exceed, the above-stated, exemplary dosage range in order to effectively and aggressively treat particularly aggressive diseases or infections. In some embodiments, the peptides will be administered for a period of continuous therapy, for example for a week or more, or for months or years.

In cases of local administration or selective uptake, the effective local concentration of the drug may not be related to plasma concentration. The amount of the instant composition administered may be dependent on the subject being treated, on the subject's weight, the severity of the affliction, and the manner of administration.

Compounds disclosed herein can be evaluated for efficacy and toxicity using known methods. The results of such studies are often predictive of efficacy in animals, such as mammals, or more specifically, humans. Alternatively, the efficacy of particular compounds in an animal model, such as mice, rats, rabbits, or monkeys, may be determined using known methods.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose".

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339).

The agonistic peptides, antagonistic peptides, MRLs and associated peptidomimetics described herein are effective in treating CLR/RAMP receptor-, somatostatin receptor-, neurotensin receptor-, apelin receptor-, bradykinin receptor-, and/or angiotensin II receptor-mediated conditions when administered at an exemplary dosage range of, for example, from about 0.01 µg to about 50 mg/kg of body weight per day. The specific dose employed is regulated by the particular condition being treated, the route of administration as well as by the judgment of the attending clinician depending upon factors such as the severity of the condition, the age and general condition of the patient, and the like. Such doses can be readily determined by those of skill in the art.

Injectables can be prepared in conventional forms, either as liquid solutions, suspensions, solid forms suitable for solution or suspension in liquid prior to injection, emulsions, or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, polylactic acid (PLA), polylactic, polyglycolic copolymers (PLG), or poly(lactic-co-glycolic acid)(PLGA). Many methods for the preparation of such formulations are generally known to those skilled in the art.

Suitable excipients are, for example, water, saline, acetate, citrate, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized. The compositions may take such forms as suspensions, solutions or emulsions in oily or aqueous vehicles, and may contain formulatory agents such as suspending, stabilizing and/or dispersing agents. Aqueous injection suspensions may contain substances which increase the viscosity of the suspension, such as sodium carboxymethyl cellulose, sorbitol, or dextran.

For transmucosal administration, penetrants appropriate to the barrier to be permeated may be used in the formulation. Suitable lipophilic solvents or vehicles include fatty oils such as sesame oil, or other organic oils such as soybean, grapefruit or almond oils, or synthetic fatty acid esters, such as ethyl oleate or triglycerides, or liposomes.

Further disclosed herein are various pharmaceutical compositions well known in the pharmaceutical art for uses that include intraocular, intranasal, and intraauricular delivery. Pharmaceutical compositions for intraocular delivery include aqueous ophthalmic solutions of the active compounds in water-soluble form, such as eye drops, or in gellan gum (Shedden et al, (2001) Clin. Ther., 23:440-50) or hydrogels (Mayer et al., (1996) Ophthalmologica, 210:101-3); ophthalmic ointments; ophthalmic suspensions, such as microparticulates, drug-containing small polymeric particles that are suspended in a liquid carrier medium (Joshi, A., (1994) Ocul. Pharmacol, 10:29-45), lipid-soluble formulations (Aim et al, (1989) Prog. Clin. Biol. Res., 312:447-58), and microspheres (Mordenti, (1999) Toxicol. Sci., 52:101-6); and ocular inserts.

Pharmaceutical compositions for intranasal delivery may also include drops and sprays often prepared to simulate in many respects nasal secretions to ensure maintenance of normal ciliary action, such compositions include, for example and without limitation, the nasal solutions disclosed by Azria, et al., in U.S. Pat. No. 5,733,569, issued Mar. 31, 1998. As disclosed in Remington's Pharmaceutical Sciences, 18th Ed., Mack Publishing Co., Easton, Pa. (1990), and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

Typically, the dose range of the composition administered to the patient can be from about 0.000001 to 100 mg/kg of the patient's body weight. The dosage may be a single one or a series of two or more given in the course of one or more days, as is needed by the patient. Dosage amount and interval may be adjusted individually to provide plasma levels of the active moiety which are sufficient to maintain the modulating effects, or minimal effective concentration (MEC). Dosage intervals can also be determined using MEC value. Compositions should be administered using a regimen which maintains plasma levels above the MEC for 10-90% of the time.

In some embodiments, the invention also provides a therapeutic kit comprising a CLR/RAMP receptor agonist, CLR/RAMP receptor antagonist or MRL of the invention, a nucleic acid molecule of the invention, an expression vector of the invention, or a host cell of the invention, each optionally in combination with a pharmaceutically acceptable carrier. In some embodiments, the invention provides a device comprising a CLR/RAMP receptor agonist, CLR/RAMP receptor, antagonist or MRL of the invention, a nucleic acid molecule of the invention, an expression vector of the invention, or a host cell of the invention for delivery of the CLR/RAMP receptor agonist, CLR/RAMP receptor antagonists or MRL to a subject.

Throughout the specification, any recitation of a particular compound should be understood to encompass that compound and any (other) pharmaceutically acceptable salt thereof.

Some embodiments provide a CLR/RAMP receptor superagonist or super-antagonist having the structure selected from the following peptide sequences, listed in Table 1.

TABLE 1

List of synthetic CLR/RAMP receptor agonist and antagonist sequences

| Sequence | SEQ ID NO |
|---|---|
| B0-B1-B2-C-B4-B5-G-B7-C-B9-B10-B11-B12-B13-B14-B15-B16-B17-B18-B19-B20-B21 | (SEQ ID NO: 1) |
| miniPEG-K(PAL)GCRFGTCTVQKLAHQIYQFT- | (SEQ ID NO: 2) |
| miniPEG-K(PAL)GCRFGTCTVQKLAHLWQLM- | (SEQ ID NO: 3) |
| Pal-KGCRFGTCTVQKLAHQIYQFT- | (SEQ ID NO: 4) |
| Pal-KGCRFGTCTVQKLAHLWQLM- | (SEQ ID NO: 5) |
| Ace-K(PAL)GCRFGTCTVQKLAHQIYQFT- | (SEQ ID NO: 6) |
| Ace-K(PAL)GCRFGTCTVQKLAHLWQLM- | (SEQ ID NO: 7) |
| Pal-K(Pal)GCRFGTCTVQKLAHQIYQFT- | (SEQ ID NO: 8) |
| Pal-KTKKTLRTGCRFGTCTVQKLAHQIYQFT- | (SEQ ID NO: 9) |
| Ace-TK(Pal)KTLRTGCRFGTCTVQKLAHQIYQFT- | (SEQ ID NO: 10) |
| Ace-TK(Pal)KTLRTGCRFGTCTVQKLAHQIYQFT- | (SEQ ID NO: 11) |
| miniPEG-TK(Pal)KTLRTGCRFGTCTVQKLAHQIYQFT- | (SEQ ID NO: 12) |
| miniPEG-K(PAL)CRFGTCTVQKLAHQIYQFT- | (SEQ ID NO: 13) |
| Pal-KCRFGTCTVQKLAHQIYQFT- | (SEQ ID NO: 14) |
| Pal-GCRFGTCTVQKLAHQIYQFT- | (SEQ ID NO: 15) |
| Pal-CRFGTCTVQKLAHQIYQFT- | (SEQ ID NO: 16) |
| C1-C2-C3-C4-C5-C6-C7-C8-C9-C10-C11-C12 | (SEQ ID NO: 17) |
| DKDKDNVAPRSK- | (SEQ ID NO: 18) |
| DKDKDNSAPVDP- | (SEQ ID NO: 19) |
| PAGRQDSAPVDP- | (SEQ ID NO: 20) |
| DKDKDNVAPVDP- | (SEQ ID NO: 21) |
| DKDKQDSAPVDP- | (SEQ ID NO: 22) |
| DKGRQDSAPVDP- | (SEQ ID NO: 23) |
| DKDKDSAPVDP- | (SEQ ID NO: 24) |
| DKDKSAPVDP- | (SEQ ID NO: 25) |
| DKDSAPVDP- | (SEQ ID NO: 26) |
| D1-D2-D3-D4-D5-D6-NH2 | (SEQ ID NO: 27) |
| Pan-specific superagonist peptide sequence | |
| miniPEG-K(PAL)GCRFGTCTVQKLAHQIYQFTDKDKDNSAPVDPSSPHSY-NH2 | (SEQ ID NO: 28) |
| miniPEG-K(PAL)GCRFGTCTVQKLAHQIYQFTPAGRQDSAPVDPSSPHSY-NH2 | (SEQ ID NO: 29) |
| Pal-KGCRFGTCTVQKLAHQIYQFTDKDKDNSAPVDPSSPHSY-NH2 | (SEQ ID NO: 30) |
| Pal-KGCRFGTCTVQKLAHQIYQFTPAGRQDSAPVDPSSPHSY-NH2 | (SEQ ID NO: 31) |
| Ace-K(PAL)GCRFGTCTVQKLAHQIYQFTDKDKDNSAPVDPSSPHSY-NH2 | (SEQ ID NO: 32) |
| Ace-K(PAL)GCRFGTCTVQKLAHQIYQFTPAGRQDSAPVDPSSPHSY-NH2 | (SEQ ID NO: 33) |
| Pal-KGCRFGTCTVQKLAHQIYQFTDKDKDNVAPVDPSSPHSY-NH2 | (SEQ ID NO: 34) |
| Pal-KGCRFGTCTVQKLAHQIYQFTDKDKQDSAPVDPSSPHSY-NH2 | (SEQ ID NO: 35) |
| Pal-KGCRFGTCTVQKLAHQIYQFTDKGRQDSAPVDPSSPHSY-NH2 | (SEQ ID NO: 36) |
| Pal-K(Pal)GCRFGTCTVQKLAHQIYQFTDKDKDNSAPVDPSSPHSY-NH2 | (SEQ ID NO: 37) |
| Pal-KTKKTLRTGCRFGTCTVQKLAHQIYQFTDKDKDNSAPVDPSSPHSY-NH2 | (SEQ ID NO: 38) |
| Ace-TK(Pal)KTLRTGCRFGTCTVQKLAHQIYQFTDKDKDNSAPVDPSSPHSY-NH2 | (SEQ ID NO: 39) |
| Pal-KTKKTLRTGCRFGTCTVQKLAHQIYQFTDKDKDNVAPVDPSSPHSY-NH2 | (SEQ ID NO: 40) |
| Ace-TK(Pal)KTLRTGCRFGTCTVQKLAHQIYQFTDKDKDNVAPVDPSSPHSY-NH2 | (SEQ ID NO: 41) |
| miniPEG-TK(Pal)KTLRTGCRFGTCTVQKLAHQIYQFTDKDKDNVAPVDPSSPHSY-NH2 | (SEQ ID NO: 42) |
| miniPEG-K(PAL)CRFGTCTVQKLAHQIYQFTDKDKDNSAPVDPSSPHSY-NH2 | (SEQ ID NO: 43) |
| Pal-KCRFGTCTVQKLAHQIYQFTDKDKDNSAPVDPSSPHSY-NH2 | (SEQ ID NO: 44) |
| Pal-GCRFGTCTVQKLAHQIYQFTDKDKDNSAPVDPSSPHSY-NH2 | (SEQ ID NO: 45) |
| miniPEG-K(PAL)GCRFGTCTVQKLAHQIYQFTDKDKDSAPVDPSSPHSY-NH2 | (SEQ ID NO: 46) |

TABLE 1-continued

List of synthetic CLR/RAMP receptor agonist and antagonist sequences

| | |
|---|---|
| miniPEG-K(PAL)GCRFGTCTVQKLAHQIYQFTDKDKSAPVDPSSPHSY-NH2 | (SEQ ID NO: 47) |
| miniPEG-K(PAL)GCRFGTCTVQKLAHQIYQFTDKDSAPVDPSSPHSY-NH2 | (SEQ ID NO: 48) |
| miniPEG-K(PAL)GCRFGTCTVQKLAHQIYQFTPAGRQDSAPVDPSSPHSY-NH2 | (SEQ ID NO: 49) |
| miniPEG-K(PAL)GCRFGTCTVQKLAHQIYQFTDKDKDNVAPVDPSSPHSY-NH2 | (SEQ ID NO: 50) |
| miniPEG-K(PAL)GCRFGTCTVQKLAHQIYQFTDKDKQDSAPVDPSSPHSY-NH2 | (SEQ ID NO: 51) |
| Pal-KGCRFGTCTVQKLAHQIYQFTDKDSAPVDPSSPHSY-NH2 | (SEQ ID NO: 92) |
| Ace-RPKPQQFFGLM-miniPEG-K(PAL)GCRFGTCTVQKLAHQIYQFTDKDSAPVDPSSPHSY-NH2 | (SEQ ID NO: 147) |
| Ace-PEG12-PEG12-K([19-carboxy-nonadecanoyl]-isoGlu-PEG3)GCRFGTCTVQKLAHQIYQFTDKDKDNVAPRSKISPQGY-NH2 | (SEQ ID NO: 150) |
| Ace-PEG3-K(Hexadecanoyl-isoGlu)GCRFGTCTVQKLAHQIYQFTDKDKDNVAPRSKISPQGY-NH2 | (SEQ ID NO: 151) |
| Ace-PEG3-K(Hexadecanoyl-isoGlu-PEG3)GCRFGTCTVQKLAHQIYQFTDKDKDNVAPRSKISPQGY-NH2 | (SEQ ID NO: 152) |
| Ace-PEG3-K(Hexadecanoyl-isoGlu-PEG3-PEG3)GCRFGTCTVQKLAHQIYQFTDKDKDNVAPRSKISPQGY-NH2 | (SEQ ID NO: 153) |
| Ace-PEG3-K(Hexadecanoyl-PEG3-isoGlu)GCRFGTCTVQKLAHQIYQFTDKDKDNVAPRSKISPQGY-NH2 | (SEQ ID NO: 154) |
| Ace-PEG3-K([19-carboxy-nonadecanoyl]-isoGlu)GCRFGTCTVQKLAHQIYQFTDKDKDNVAPRSKISPQGY-NH2 | (SEQ ID NO: 155) |
| Ace-PEG3-K([19-carboxy-nonadecanoyl]-PEG3-isoGlu)GCRFGTCTVQKLAHQIYQFTDKDKDNVAPRSKISPQGY-NH2 | (SEQ ID NO: 156) |
| Ace-PEG3-K([19-carboxy-nonadecanoyl]-isoGlu-Peg3-Peg3)GCRFGTCTVQKLAHQIYQFTDKDKDNVAPRSKISPQGY-NH2 | (SEQ ID NO: 157) |
| AcePEG3--K([17-carboxy-heptadecanoyl]-isoGlu-Peg3-Peg3)GCRFGTCTVQKLAHQIYQFTDKDKDNVAPRSKISPQGY-NH2 | (SEQ ID NO: 158) |
| Ace-PEG3-K([19-carboxy-nonadecanoyl]-isoGlu-PEG3)GCRFGTCTVQKLAHQIYQFTDKDVAPRSKISPQGY-NH2 | (SEQ ID NO: 159) |
| miniPEG-K(PAL)GCRFGTCTVQKLAHQIYQFTDKDVAPR(D-Ser)KISPQGY-NH2 | (SEQ ID NO: 213) |

Wild-type IMD, ADM, and CGRP

| | |
|---|---|
| Ace-VGCVLGTCQVQNISHRLWQLMGPAGRQDSAPVDPSSPHSY-NH2 | (SEQ ID NO: 52) |
| Ace-FGCRFGTCTVQKLAHQIYQFTDKDKDNVAPRSKISPQGY-NH2 | (SEQ ID NO: 53) |
| Ace-YRQSMNNFQGIRSFQCRFGTCTVQKLAHQIYQFTDKDKDNVAPRSKISPQGY-NH2 | (SEQ ID NO: 54) |
| ACNTATCVTHRLAGLISRSGGMVKSNFVPTNVGSKAF-NH2 | (SEQ ID NO: 143) |

Inactive or low potency agonistic chimeric peptide sequence

| | |
|---|---|
| Ace-VGCRFGTCTVQKLAHQIYQFTDKDKDNVAPRSKSSPHSY-NH2 | (SEQ ID NO: 55) |
| Ace-VGCRFGTCTVQKLAHQIYQFTDKDKDNSAPVDPSSPHSY-NH2 | (SEQ ID NO: 56) |
| Ace-VGCRFGTCTVQKLAHQIYQFTPAGRQDSAPVDPSSPHSY-NH2 | (SEQ ID NO: 57) |
| Ace-VGCRFGTCTVQKLAHLWQLMGPAGRQDSAPVDPSSPHSY-NH2 | (SEQ ID NO: 58) |
| Ace-KGCRFGTCTVQKLAHQIYQFTDKDKDNSAPVDPSSPHSY-NH2 | (SEQ ID NO: 59) |
| Ace-KGCRFGTCTVQKLAHQIYQFTDKDKDNVAPVDPSSPHSY-NH2 | (SEQ ID NO: 60) |
| miniPEG-K(PAL)GCRFGTCTVQKLAHQIYQFTDKDKDNVAPRSKSSPHSY-NH2 | (SEQ ID NO: 61) |
| miniPEG-K(PAL)GCRFGTCTVQKLAHLWQLMGPAGRQDSAPVDPSSPHSY-NH2 | (SEQ ID NO: 62) |
| Pal-KGCRFGTCTVQKLAHQIYQFTDKDKDNVAPRSKSSPHSY-NH2 | (SEQ ID NO: 63) |
| Pal-KGCRFGTCTVQKLAHLWQLMGPAGRQDSAPVDPSSPHSY-NH2 | (SEQ ID NO: 64) |
| Ace-K(PAL)GCRFGTCTVQKLAHQIYQFTDKDKDNVAPRSKSSPHSY-NH2 | (SEQ ID NO: 65) |
| Ace-K(PAL)GCRFGTCTVQKLAHLWQLMGPAGRQDSAPVDPSSPHSY-NH2 | (SEQ ID NO: 66) |
| Pal-CRFGTCTVQKLAHQIYQFTDKDKDNSAPVDPSSPHSY-NH2 | (SEQ ID NO: 67) |
| miniPEG-K(PAL)GCRFGTCTVQKLAHQIYQFTDKGRQDSAPVDPSSPHSY-NH2 | (SEQ ID NO: 68) |
| Ace-KGCRFGTCTVQKLAHQIYQFTDKDSAPVDPSSPHSY-NH2 | (SEQ ID NO: 93) |
| Pal-ACDTATCVTHRLAGLISRFTDKDKDNVAPRSKISPQGY-NH2 | (SEQ ID NO: 104) |
| Pal-FGCRFGTCTVQKLAHRLWQLMGPDKDNVAPRSKISPQGY-NH2 | (SEQ ID NO: 105) |
| Pal-ACDTATCVTHRLAGLISRSGGVNFVPTNVGSKAF-NH2 | (SEQ ID NO: 108) |

CLR/RAMP2-selective superagonist peptide sequence

| | |
|---|---|
| miniPEG-K(PAL)GCRFGTCTVQKLAHQIYQFTDKDKDNVAPRSKISPQGY-NH2 | (SEQ ID NO: 69) |
| miniPEG-K(PAL)TKKTLRTGCRFGTCTVQKLAHQIYQFTDKDKDNVAPRSKISPQGY-NH2 | (SEQ ID NO: 70) |
| miniPEG-K(PAL)GCRFGTCTVQKLAHQIYQFTDKDKDNVDPSSPHSY-NH2 | (SEQ ID NO: 94) |
| miniPEG-K(PAL)GCRFGTCTVQKLAHQIYQFTDKDVAPRSKISPQGY-NH2 | (SEQ ID NO: 101) |
| Pal-KGCRFGTCTVQKLAHQIYQFTDKDVAPRSKISPQGY- NH2 | (SEQ ID NO: 103) |
| Pal-KGCRFGTCTVQKLAHQIYQFTDKDAPVDPSSPHSY-NH2 | (SEQ ID NO: 110) |
| Ace-K(Hexadecanoyl-isoGlu)GCRFGTCTVQKLAHQIYQFTDKDKDNVAPRSKISPQGY-NH2 | (SEQ ID NO: 160) |
| Ace-K(Hexadecanoyl-isoGlu-PEG3)GCRFGTCTVQKLAHQIYQFTDKDKDNVAPRSKISPQGY-NH2 | (SEQ ID NO: 161) |
| Ace-K(Hexadecanoyl-isoGlu-PEG3-PEG3)GCRFGTCTVQKLAHQIYQFTDKDKDNVAPRSKISPQGY-NH2 | (SEQ ID NO: 162) |
| Ace-K(Hexadecanoyl-PEG3-IsoGlu)GCRFGTCTVQKLAHQIYQFTDKDKDNVAPRSKISPQGY-NH2 | (SEQ ID NO: 163) |
| Ace-K([19-carboxy-nonadecanoyl]-isoGlu)GCRFGTCTVQKLAHQIYQFTDKDKDNVAPRSKISPQGY-NH2 | (SEQ ID NO: 164) |

TABLE 1-continued

List of synthetic CLR/RAMP receptor agonist and antagonist sequences

| | |
|---|---|
| Ace-K([19-carboxy-nonadecanoyl]-PEG3-IsoGlu)<br>GCRFGTCTVQKLAHQIYQFTDKDKDNVAPRSKISPQGY-NH2 | (SEQ ID NO: 165) |
| Ace-K([19-carboxy-nonadecanoyl]-isoGlu-PEG3-PEG3)<br>GCRFGTCTVQKLAHQIYQFTDKDKDNVAPRSKISPQGY-NH2 | (SEQ ID NO: 166) |
| Ace-K([17-carboxy-heptadecanoyl]-isoGlu-PEG3-PEG3)<br>GCRFGTCTVQKLAHQIYQFTDKDKDNVAPRSKISPQGY-NH2 | (SEQ ID NO: 167) |
| Ace-K([19-carboxy-nonadecanoyl]-isoGlu-PEG3)<br>GCRFGTCTVQKLAHQIYQFTDKDKDNVAPRSKISPQGY-NH2 | (SEQ ID NO: 168) |
| Ace-PEG12-PEG12-K([19-carboxy-nonadecanoyl]-isoGlu-PEG3)<br>GCRFGTCTVQKLAHQIYQFTDKDKDNVAPRSKISPQGY-NH2 | (SEQ ID NO: 169) |
| miniPEG-K(PAL)GCRFGTC(D-Thr)VQKLAHQIYQFTDKDVAPRSKISPQGY-NH2 | (SEQ ID NO: 210) |
| miniPEG-K(PAL)GCRFGTCT(D-Val)QKLAHQIYQFTDKDVAPRSKISPQGY-NH2 | (SEQ ID NO: 211) |
| miniPEG-K(PAL)GCRFGTCTVQKLAH(D-Gln)IYQFTDKDVAPRSKISPQGY-NH2 | (SEQ ID NO: 212) |
| miniPEG-K(PAL)GCRFGTCTVQKLAHQIYQFTDKDVAPRSKISP(D-Gln)GY-NH2 | (SEQ ID NO: 214) |

Low potency CLR/RAMP1- or CLR/RAMP2-selective peptide sequence

| | |
|---|---|
| Pal-GCRFGTCTVQKLAHQIYQFTDKDKDNVAPRSKISPQGY-NH2 | (SEQ ID NO: 71) |
| Pal-YRQSMNNFQGLRSFQCRFGTCTVQKLAHQIYQFTDKDKDNVAPRSKISPQGY-NH2 | (SEQ ID NO: 72) |
| Pal-K(Pal)GCRFGTCTVQKLAHQIYQFTDKDKDNVAPRSKISPQGY-NH2 | (SEQ ID NO: 73) |
| Ace-K(Pal)GCDTATCVTHRLAGLLSRSGGVVKNNFVPTNVGSKAF-NH2 | (SEQ ID NO: 74) |

Pan-specific super-antagonist peptide sequence

| | |
|---|---|
| Pal-TVQKLAHQIYQFTDKDKDNSAPVDPSSPHSY-NH2 | (SEQ ID NO: 77) |
| miniPEG-K(Pal)VQKLAHQIYQFTDKDKDNSAPVDPSSPHSY-NH2 | (SEQ ID NO: 78) |
| MiniPEG-K(Pal)VQKLAHQIYQFTDKDSAPVDPSSPHSY-NH2 | (SEQ ID NO: 112) |
| Pal-KVQKLAHQIYQFTDKDSAPVDPSSPHSY-NH2 | (SEQ ID NO: 121) |
| Pal-KVQKLAHQIYQFTDKSAPVDPSSPHSY-NH2 | (SEQ ID NO: 125) |
| Ace-K(Hexadecanoyl-isoGlu)VQKLAHQIYQFTDKDSAPVDPSSPHSY-NH2 | (SEQ ID NO: 170) |
| Ace-K(Hexadecanoyl-isoGlu-PEG3)VQKLAHQIYQFTDKDSAPVDPSSPHSY-NH2 | (SEQ ID NO: 171) |
| Ace-K(Hexadecanoyl-isoGlu-PEG3-PEG3)VQKLAHQIYQFTDKDSAPVDPSSPHSY-NH2 | (SEQ ID NO: 172) |
| Ace-K(Hexadecanoyl-PEG3-IsoGlu)VQKLAHQIYQFTDKDSAPVDPSSPHSY-NH2 | (SEQ ID NO: 173) |
| Ace-K([19-carboxy-nonadecanoyl]-isoGlu)VQKLAHQIYQFTDKDSAPVDPSSPHSY-NH2 | (SEQ ID NO: 174) |
| Ace-K([19-carboxy-nonadecanoyl]-PEG3-isoGlu)VQKLAHQIYQFTDKDSAPVDPSSPHSY-NH2 | (SEQ ID NO: 175) |
| Ace-K([19-carboxy-nonadecanoyl]-isoGlu-PEG3-PEG3)VQKLAHQIYQFTDKDSAPVDPSSPHSY-NH2 | (SEQ ID NO: 176) |
| Ace-K([17-carboxy-heptadecanoyl]-isoGlu-PEG3-PEG3)VQKLAHQIYQFTDKDSAPVDPSSPHSY-NH2 | (SEQ ID NO: 177) |
| Ace-K([19-carboxy-nonadecanoyl]-isoGlu-PEG3)VQKLAHQIYQFTDKDSAPVDPSSPHSY-NH2 | (SEQ ID NO: 178) |
| Ace-PEG12-PEG12-K([19-carboxy-nonadecanoyl]-isoGlu-PEG3)VQKLAHQIYQFTDKDSAPVDPSSPHSY-NH2 | (SEQ ID NO: 179) |

Wild type antagonistic peptide sequence

| | |
|---|---|
| Ace-TVQKLAHQIYQFTDKDKDNVAPRSKISPQGY-NH2 | (SEQ ID NO: 75) |
| Ace-VTHRLAGLLSRSGGVVKNNFVPTNVGSKAF-NH2 | (SEQ ID NO: 137) |

Low potency antagonistic peptide sequence

| | |
|---|---|
| Ace-TVQKLAHQIYQFTDKDKDNSAPVDPSSPHSY-NH2 | (SEQ ID NO: 76) |
| Ace-VTHRLAGLLSRFTDKDKDNVAPRSKISPQGY-NH2 | (SEQ ID NO: 115) |
| Ace-TVQKLAHRLWQLMGPDKDNVAPRSKISPQGY-NH2 | (SEQ ID NO: 116) |
| Pal-VTHRLAGLLSRFTDKDKDNVAPRSKISPQGY-NH2 | (SEQ ID NO: 117) |
| Pal-TVQKLAHRLWQLMGPDKDNVAPRSKISPQGY-NH2 | (SEQ ID NO: 118) |
| Pal-KVQNLSAPVDPSSPHSY-NH2 | (SEQ ID NO: 141) |
| Ace-NFVPTNVGPFAF-NH2 | (SEQ ID NO: 144) |

CLR/RAMP1-selective super-antagonist peptide sequence

| | |
|---|---|
| MiniPEG-K(Pal)VQKLAHQIYSAPVDPSSPHSY-NH2 | (SEQ ID NO: 114) |
| Pal-KVQNLSHRLWQLMGPAGSAPVDPSSPHSY-NH2 | (SEQ ID NO: 120) |
| Pal-KVQKLAHQIYSAPVDPSSPHSY-NH2 | (SEQ ID NO: 122) |
| Pal-KVQKLAHQISAPVDPSSPHSY-NH2 | (SEQ ID NO: 123) |
| Pal-KVQKLAHQSAPVDPSSPHSY-NH2 | (SEQ ID NO: 124) |
| Pal-KVQKLSAPVDPSSPHSY-NH2 | (SEQ ID NO: 139) |
| miniPEG-K(PAL)VQKLSAPVDPSSPHSY-NH2 | (SEQ ID NO: 140) |
| Ace-Y(D-Ala)GF(D-Leu)-miniPEG-K(Pal)VQKLSAPVDPSSPHSY-NH2 | (SEQ ID NO: 145) |
| Ace-YGGFLRRIRPKLK-miniPEG-K(Pal)VQKLSAPVDPSSPHSY-NH2 | (SEQ ID NO: 146) |
| Ace-K(Hexadecanoyl-isoGlu)VQKLSAPVDPSSPHSY-NH2 | (SEQ ID NO: 180) |

TABLE 1-continued

List of synthetic CLR/RAMP receptor agonist and antagonist sequences

| | |
|---|---|
| Ace-K(Hexadecanoyl-isoGlu-PEG3)VQKLSAPVDPSSPHSY-NH2 | (SEQ ID NO: 181) |
| Ace-K(Hexadecanoyl-isoGlu-PEG3-PEG3)VQKLSAPVDPSSPHSY-NH2 | (SEQ ID NO: 182) |
| Ace-K(Hexadecanoyl-PEG3-isoGlu)VQKLSAPVDPSSPHSY-NH2 | (SEQ ID NO: 183) |
| Ace-K([19-carboxy-nonadecanoyl]-isoGlu)VQKLSAPVDPSSPHSY-NH2 | (SEQ ID NO: 184) |
| Ace-K([19-carboxy-nonadecanoyl]-PEG3-isoGlu)VQKLSAPVDPSSPHSY-NH2 | (SEQ ID NO: 185) |
| Ace-K([19-carboxy-nonadecanoyl]-isoGlu-PEG3-PEG3)VQKLSAPVDPSSPHSY-NH2 | (SEQ ID NO: 186) |
| Ace-K([17-carboxy-heptadecanoyl]-isoGlu-PEG3-PEG3)VQKLSAPVDPSSPHSY-NH2 | (SEQ ID NO: 187) |
| Ace-K([19-carboxy-nonadecanoyl]-isoGlu-PEG3)VQKLSAPVDPSSPHSY-NH2 | (SEQ ID NO: 188) |
| Ace-PEG12-PEG12-K([19-carboxy-nonadecanoyl]-isoGlu-PEG3)VQKLSAPVDPSSPHSY-NH2 | (SEQ ID NO: 189) |

CLR/RAMP2-selective super-antagonist peptide sequence

| | |
|---|---|
| Pal-KVQKLAHQIYQFTDKDVAPRSKISPQGY-NH2 | (SEQ ID NO: 119) |
| Ace-YNWNSFGLRF-miniPEG-K(PAL)VQKLAHQIYQFTDKDVAPRSKISPQGY-NH2 | (SEQ ID NO: 148) |
| Ace-KRPPGFSPFR-miniPEG-K(Pal)VQKLAHQIYQFTDKDVAPRSKISPQGY-NH2 | (SEQ ID NO: 149) |
| PEG20,000-K[PAL]VQKLAHQIYQFTDKDSAPVDPSSPHSY-NH2 | (SEQ ID NO: 190) |
| PEG2000-K[PAL]VQKLAHQIYQFTDKDSAPVDPSSPHSY-NH2 | (SEQ ID NO: 191) |
| PEG5000-K[PAL]VQKLAHQIYQFTDKDSAPVDPSSPHSY-NH2 | (SEQ ID NO: 192) |
| Ace-K(Hexadecanoyl-PEG3-isoGlu)VQKLAHQIYQFTDKDVAPRSKISPQGY-NH2 | (SEQ ID NO: 193) |
| Ace-K([19-carboxy-nonadecanoyl]-isoGlu)VQKLAHQIYQFTDKDVAPRSKISPQGY-NH2 | (SEQ ID NO: 194) |
| Ace-K([19-carboxy-nonadecanoyl]-PEG3-isoGlu)VQKLAHQIYQFTDKDVAPRSKISPQGY-NH2 | (SEQ ID NO: 195) |
| Ace-K([19-carboxy-nonadecanoyl]-isoGlu-PEG3-PEG3)VQKLAHQIYQFTDKDVAPRSKISPQGY-NH2 | (SEQ ID NO: 196) |
| Ace-K([17-carboxy-heptadecanoyl]-isoGlu-PEG3-PEG3)VQKLAHQIYQFTDKDVAPRSKISPQGY-NH2 | (SEQ ID NO: 197) |
| Ace-K([19-carboxy-nonadecanoyl]-isoGlu-PEG3)VQKLAHQIYQFTDKDVAPRSKISPQGY-NH2 | (SEQ ID NO: 198) |
| Ace-PEG12-PEG12-K([19-carboxy-nonadecanoyl]-isoGlu-PEG3)VQKLAHQIYQFTDKDVAPRSKISPQGY-NH2 | (SEQ ID NO: 199) |

CLR/RAMP1-selective super-antagonistic ADM/CGRP peptide sequence

| | |
|---|---|
| Pal-KVQKLNFVPTNVGSKAF-NH2 | (SEQ ID NO: 142) |
| Ace-K(Hexadecanoyl-isoGlu)VQKLNFVPTNVGSKAF-NH2 | (SEQ ID NO: 200) |
| Ace-K(Hexadecanoyl-isoGlu-PEG3)VQKLNFVPTNVGSKAF-NH2 | (SEQ ID NO: 201) |
| Ace-K(Hexadecanoyl-isoGlu-PEG3-PEG3)VQKLNFVPTNVGSKAF-NH2 | (SEQ ID NO: 202) |
| Ace-K(Hexadecanoyl-PEG3-isoGlu)VQKLNFVPTNVGSKAF-NH2 | (SEQ ID NO: 203) |
| Ace-K([19-carboxy-nonadecanoyl]-isoGlu)VQKLNFVPTNVGSKAF-NH2 | (SEQ ID NO: 204) |
| Ace-K([19-carboxy-nonadecanoyl]-PEG3-isoGlu)VQKLNFVPTNVGSKAF-NH2 | (SEQ ID NO: 205) |
| Ace-K([19-carboxy-nonadecanoyl]-isoGlu-PEG3-PEG3)VQKLNFVPTNVGSKAF-NH2 | (SEQ ID NO: 206) |
| Ace-K([17-carboxy-heptadecanoyl]-isoGlu-PEG3-PEG3)VQKLNFVPTNVGSKAF-NH2 | (SEQ ID NO: 207) |
| Ace-K([19-carboxy-nonadecanoyl]-isoGlu-PEG3)VQKLNFVPTNVGSKAF-NH2 | (SEQ ID NO: 208) |
| Ace-PEG12-PEG12-K([19-carboxy-nonadecanoyl]-isoGlu-PEG3)VQKLNFVPTNVGSKAF-NH2 | (SEQ ID NO: 209) |

Somatostatin receptor ligand

| | |
|---|---|
| (D-Phe)CF(D-Trp)KTCT | (SEQ ID NO: 215) |
| AGCKNFFWKTFTSC | (SEQ ID NO: 216) |
| SANSNPAMAPRERKAGCKNFFWKTFTSC | (SEQ ID NO: 217) |

Somatostatin receptor/CLR/RAMP receptor MRL peptide sequence

| | |
|---|---|
| (D-Phe)CF(D-Trp)KTCT-miniPEG-K(Pal)VQKLAHQIYQFTDKDVAPRSKISPQGY-NH2 | (SEQ ID NO: 218) |
| (D-Phe)CF(D-Trp)KTCT-miniPEG-K(IsoGlu-Pal)VQKLAHQIYQFTDKDVAPRSKISPQGY-NH2 | (SEQ ID NO: 219) |
| (D-Phe)CF(D-Trp)KTCT-miniPEG-K(IsoGlu-Pal)VQKLSAPVDPSSPHSY-NH2 | (SEQ ID NO: 220) |

TABLE 1-continued

List of synthetic CLR/RAMP receptor agonist and antagonist sequences

Neurotensin receptor ligand

| | |
|---|---|
| Glp-LYENKPRRPYIL | (SEQ ID NO: 221) |
| KKPYIL | (SEQ ID NO: 222) |

Neurotensin receptor/CLR/RAMP receptor MRL peptide sequence

| | |
|---|---|
| Pyr(glu)-LYENKPRRPYIL-miniPEG-<br>K(PAL)GCRFGTCTVQKLAHQIYQFTDKDVAPRSKISPQGY-NH2 | (SEQ ID NO: 223) |
| Pyr(glu)-LYENKPRRPYIL-miniPEG-K(Pal)VQKLSAPVDPSSPHSY-NH2 | (SEQ ID NO: 224) |

Apelin receptor ligand

| | |
|---|---|
| (Glp)RPRLSHKGPMPF | (SEQ ID NO: 225) |
| KFRRQRPRLSHKGPMPF | (SEQ ID NO: 226) |
| LVQPRGSRNGPGPWQGGRRKFRRQRPRLSHKGPMPF | (SEQ ID NO: 227) |

Apelin receptor/CLR/RAMP receptor MRL peptide sequence

| | |
|---|---|
| (Glp)RPRLSHKGP(Nle)PF-miniPEG-<br>K(PAL)GCRFGTCTVQKLAHQIYQFTDKDVAPRSKISPQGY-NH2 | (SEQ ID NO: 228) |
| (Glp)RPRLSHKGP(Nle)PF-miniPEG-K(gamma-Glu-<br>PAL)GCRFGTCTVQKLAHQIYQFTDKDVAPRSKISPQGY-NH2 | (SEQ ID NO: 229) |

Bradykinin receptor ligand

| | |
|---|---|
| KRPPGFSPF | (SEQ ID NO: 230) |

Bradykinin receptor/CLR/RAMP receptor MRL peptide sequence

| | |
|---|---|
| Ace-KRPPGFS-DβNal-I-miniPEG-<br>K(PAL)GCRFGTCTVQKLAHQIYQFTDKDVAPRSKISPQGY-NH2 | (SEQ ID NO: 231) |

Angiotensin II receptor ligand

| | |
|---|---|
| DRVYIHPF | (SEQ ID NO: 232) |
| Sar-RVYVHPA | (SEQ ID NO: 233) |

Angiotensin II receptor/CLR/RAMP receptor MRL peptide sequence

| | |
|---|---|
| Sar-RVYVHPA-miniPEG-<br>K(PAL)GCRFGTCTVQKLAHQIYQFTDKDVAPRSKISPQGY-NH2 | (SEQ ID NO: 234) |

Preparation of Peptides and Peptidomimetics

Solid Phase Synthesis. The CLR/RAMP receptor superagonists, agonists, suerantagonists, antagonists, and MRLs described herein can be prepared by classical methods known in the art, for example, by using standard solid phase techniques. See, for example, Merrifield, (1963) *J. Am. Chem. Soc.* 85:2149. These solid phase peptide synthesis procedures are well known in the art and further described by J. M. Stewart and J. D. Young, (1984) *Solid Phase Peptide Syntheses* 2nd Ed., Pierce Chemical Company.

Synthetic Amino Acids. These procedures can also be used to synthesize peptides in which amino acids other than the 20 naturally occurring, genetically encoded amino acids are substituted at one, two, or more positions of any of the peptides of the invention as disclosed herein. For instance, naphthylalanine can be substituted for tryptophan, facilitating synthesis. Other synthetic amino acids that can be substituted into the peptides of the present embodiments include L-hydroxypropyl, L-3,4-dihydroxy-phenylalanyl, d amino acids such as L-d-hydroxylysyl and D-d-methylalanyl, L-α-methylalanyl, β-amino acids, and isoquinolyl. D amino acids and non-naturally occurring synthetic amino acids can also be incorporated into the peptides of the present embodiments (see, for example, Roberts, et al. (1983) *Unusual Amino/Acids in Peptide Synthesis* 5:341-449).

In some embodiments, the naturally occurring side chains of the 20 genetically encoded amino acids, or any other side chain as disclosed herein can be transposed to the nitrogen of the amino acid, instead of the α-carbon as typically found in peptides.

In some embodiments, the amino acid sequence of a CLR/RAMP receptor superagonist, a CLR/RAMP receptor super-antagonist, or an MRL can be modified, relative to the sequence of SEQ ID NOS: 28-51, 69-70, 77-78, 92, 94, 101, 103, 110, 112, 114, 119, 120-125, 139, 140, 142, 145-159, 190-192, 210, 211, 213, 214, 218, 223, 224, 228, 231, and 234 such that the modification increases or reduces receptor-activation activity, and reduces the susceptibility to enzymatic proteolysis or kidney clearance. In some embodiments this modification comprises N-terminal addition of a sequence comprising all or part of the human serum albumin or immunoglobulin proteins, or an acylation and/or PEG group. In some embodiments, peptides of the invention comprise one or more D-amino acid residues. In some embodiments, the amino acid sequence of a peptide of the invention is modified, relative to the sequence of SEQ ID NOS: 28-51, 69-70, 77-78, 92, 94, 101, 103, 110, 112, 114, 119, 120-125, 139, 140, 142, 145-159, 190-192, 210, 211, 213, 214, 218, 223, 224, 228, 231, and 234, such that the modification includes replacement of one or more L-amino acids residues with corresponding D-amino acids residues.

In some embodiments, the amino acid sequence of peptides of the invention are modified, relative to the sequence of SEQ ID NOS: 28-51, 69-70, 77-78, 92, 94, 101, 103, 110, 112, 114, 119, 120-125, 139, 140, 142, 145-159, 190-192, 210, 211, 213, 214, 218, 223, 224, 228, 231, and 234 such that the modification is substitution of one or more amino acids with a conservative amino acid or a non-proteinogenic amino acid.

Naturally occurring residues may be divided into classes based on common side chain properties:
hydrophobic: norleucine (Nor), Met, Ala, Val, Leu, De;
neutral hydrophilic: Cys, Ser, Thr, Asn, Gln;
acidic: Asp, Glu;
basic: His, Lys, Arg;
residues that influence chain orientation: Gly, Pro; and
aromatic: Trp, Tyr, Phe.

Conservative amino acid substitutions may involve exchange of a member of a class with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acids.

In some embodiments, conservative substitutions can include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between threonine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue or non-proteinogenic acid in place of a non-derivatized residue, provided that such polypeptide displays the requisite agonist activity.

Examples of amino acid residue substitutions that can be useful in accordance with the present embodiments include the following:

| Original Residue | Substitutions |
| --- | --- |
| Ala | Val, Leu, Ile, Aib |
| Arg | Lys, Gln, Asn, homoarginine |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4-Diamino-butyric Acid, Gln, Asn, ornithine |
| Met | Leu, Phe, Ile |
| Phe | Leu, Val, Ile, Ala, Tyr |
| Pro | Ala |
| Ser | Thr, Ala, Cys |
| Thr | Ser, Val, Ile |
| Trp | Tyr, Phe |
| Tyr | Trp, Phe, Thr, Ser |
| Val | Ile, Met, Leu, Phe, Ala, Norleucine |

In some embodiments, a basic moiety of an amino acid as disclosed herein, such as the guanidine of Arg, can be replaced by a base bioisostere. In some embodiments, the substitutions can be with non-proteinogenic amino acids.

One can also readily modify the peptides of the instant embodiments by other methods for making peptide derivatives of the compounds of the present embodiments are described in Hruby, et al. (1990) Biochem. J. 268:249-262. Thus, the peptides as disclosed herein also serve as a basis to prepare peptidomimetics with similar biological activity.

Terminal Modifications

Those of skill in the art recognize that a variety of techniques are available for constructing peptidomimetics with the same or similar desired biological activity as the corresponding CLR/RAMP receptor superagonists, superantagonists, or MRLs but with more favorable activity than the reference peptide with respect to solubility, stability, and susceptibility to hydrolysis and proteolysis. See, for example, Morgan, et al. (1989) Ann. Rep. Med. Chem. 24:243-252. The following describes methods for preparing peptidomimetics modified at the N-terminal amino group, the C-terminal carboxyl group, and/or changing one or more of the amido linkages in the peptide to a non-amido linkage. It being understood that two or more such modifications can be coupled in one peptidomimetic structure (for example, modification at the C-terminal carboxyl group and inclusion of a —$CH_2$-carbamate linkage between two amino acids in the peptide). Also, the modifications can include a number of conjugations on the same side chain or different side chains. Examples include the placement of a string of amino acids, PEG groups and fatty acid on a side chain or on multiple side chains of an amino acid.

N-Terminal Modifications

Peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —$NHCH_3$ or —$NH(CH_3)_2$), acetylation, acylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups.

Amino terminus modifications are as recited above and include alkylating, acetylating, acylation, acylation plus PEG group(s)(e.g., (PEG3)n-palmitic acid), acylation plus PEG group and amino acids (e.g., γ-glutamic acid-PEG3-PEG3-palmitic acid), adding a carbobenzoyl group, forming a succinimide group, etc. See, for example, Murray, et al. (1995) Burger's Medicinal Chemistry and Drug Discovery 5th ed., Vol. 1, Manfred E. Wolf, ed., John Wiley and Sons, Inc.

The N-terminus may also be modified through the addition of at least one residues N-terminal to the $B^a$ fragment of Formula I-II. Techniques for assessing the impact of N-terminal extensions to peptides are known in the art in, for example, Schellenberger, et al., (2009) Nature Biotechnology 27:1186-1192.

C-Terminal Modifications

Carboxy terminus modifications include replacing the free acid with a carboxamide group or forming a cyclic lactam at the carboxy terminus to introduce structural constraints. In preparing peptidomimetics wherein the C-terminal carboxyl group is replaced by the amide, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide. Side chain protection is then removed in the usual fashion by treatment with hydrogen fluoride to give the free amides, alkylamides, or dialkylamides.

In addition to the foregoing N-terminal modifications, the modified peptide ligands described herein, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. In some embodiments, the CLR/RAMP receptor superagonists, super-antagonists, and MRLs as disclosed and described herein can be derivatized with or coupled to such polymers using any of the methods set forth in Zallipsky, S. (1995) *Bioconjugate Chem* 6:150-165; Monfardini, C, et al. (1995) *Bioconjugate Chem* 6:62-69.

Backbone Modifications

Other methods for making peptide derivatives of the compounds are described in Hruby, et al. (1990) Biochem. J. 268:249-262. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the leads with respect to solubility, stability, and susceptibility to hydrolysis and proteolysis. See Morgan, et al. (1989) Ann. Rep. Med. Chem. 24:243-252, incorporated herein by reference in its entirety.

Disulfide Bond Formation

The compounds may exist in a cyclized form with one or more intramolecular disulfide bond between the thiol groups of the cysteines.

Other embodiments include analogs of these disulfide derivatives in which one of the sulfurs has been replaced by a CH$_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The peptides of the present embodiments can be cyclized or dimerized via displacement of the leaving group by the sulfur of the cysteine or homocysteine residue, or by adding cyclic lactam bridge. See, for example, Andreu, et al. (1994) *Meth. Mol. Bio.* 35:91-169.

In some embodiments, the peptides of the invention as disclosed and described herein as well as their fusion proteins may also be prepared by recombinant DNA techniques well known in the art. The fusion proteins may include, but are not limited to, those with human serum albumin, immunoglobulin, Fc, Fc derivatives, microglobulin, or other serum proteins.

Other Utility

The compounds described herein can be used as reagents for selectively detecting CLR/RAMP receptors on living cells, fixed cells, in biological fluids, in tissue homogenates, in human bodies, etc. An antibody that specifically binds to one or more of the peptides described herein can be generated by methods known to one of skill in the art, which antibody may be used, for example, in the detection and analysis of the peptides described herein.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Based on evidence that CLR/RAMP receptors modulate a number of central nervous system (CNS) and peripheral vascular activities, many analogs of adrenomedullin, CGRPs and intermedin have been synthesized and studied. Thus far, known synthetic analogs of these peptide hormones exhibit receptor-activation activities either comparative or inferior to wild type ligands. Likewise, synthetic antagonistic analogs of these peptide hormones (e.g., CGRP8-37 and ADM22-52; Rovero, P. et al. (1992) Peptides 13:1025-1027) exhibit mild bioactivities and are mainly specific for one of the three CLR/RAMP receptors (i.e., CLR/RAMP1, 2, and 3 receptors). No pan-specific superagonist or antagonist as well as CLR/RAMP1- or 2-selective superagonist and super-antagonist was previously known.

In humans and other mammals, including rodents, there are three CLR/RAMP receptors for adrenomedullin, CGRPs, and intermedin. These are CLR/RAMP1, 2, and 3 receptors, which are expressed throughout the vascular system. It has been reported that CGRPs are selective agonists for CLR/RAMP1 whereas adrenomedullin interacts with high affinity with CLR/RAMP2. On the other hand, intermedin is a low potency ligand and does not exhibit specific preference among CLR/RAMP1, 2, and 3 receptors.

Given the interesting physiological and pharmacology characteristics of these peptide hormones, we sought to identify ligands that (1) exhibit superior agonistic or antagonistic activity toward both CLR/RAMP1 and 2 receptors as well as ligands that exhibit superior agonistic or antagonistic activity toward CLR/RAMP1 or CLR/RAMP2 receptor.

We designed and synthesized a series of systematically modified derivatives of adrenomedullin and intermedin, and characterized their signaling in comparison with the parent compounds and derivatives. Findings indicate that activities of chimeric analogs with select N-terminal acylation and/or PEG modification(s) showed significantly superior bioactivity when compared to the wild-type transmitters, CGRP, ADM, or IMD. In addition, adrenomedullin analogs with both N-terminal acylation and/or PEG modifications exhibit superagonistic activity toward CLR/RAMP2 receptor selectively.

Truncated molecules comprising the sequence of ADM and/or IMD and with N-terminal acylation/PEG modification(s) were shown to compete for CGRP and ADM interaction with CLR/RAMP1, 2 and/or 3 receptors with high potency when compared to the general CLR/RAMP1 receptor antagonist CGRP8-37 and/or CLR/RAMP2 receptor antagonist ADM22-52. Also, select super-antagonistic analogs exhibit CLR/RAMP1- or CLR/RAMP2-selective antagonistic activities. The analogs thus provide a pan-specific or selective super-antagonist that binds to its complementary biologically active receptor(s) and inhibits the physiological response of the receptor stronger than the known CLR/RAMP receptor antagonists.

MRLs comprise or consist of (i) a CLR/RAMP receptor ligand and (ii) a ligand for a second GPCR selected from somatostatin receptors, neurotensin receptors, apelin receptor, bradylinin receptors, and type 1 angiotensin II receptor. MRLs are shown to agonize or antagonize CLR/RAMP receptors, and agonize or antagonize the second GPCR. These chimeric ligands are novel polypeptides capable of modulating the activities of multiple GPCR responses that are not possible by physiological ligands.

Using a receptor activation assay, the dose-dependent stimulatory response of peptide agonists on a CLR/RAMP1 receptor, a CLR/RAMP2, or a CLR/RAMP3 receptor complex was determined. A cell line carrying the recombinant CLR/RAMP1, CLR/RAMP2, or a CLR/RAMP3 receptor was employed in the assay. Peptide agonist activities were tested, in duplicate, at 10 different concentrations, starting with 1.0 µM and serially diluted 3-fold, in DMSO. Human β-CGRP, a known CLR/RAMP1 receptor agonist, was used as a positive control in the CLR/RAMP1 assays, and ADM, a known CLR/RAMP2 receptor agonist was used as a positive control in the CLR/RAMP2 assays. The CLR/RAMP1 cAMP, CLR/RAMP2 arrestin, and CLR/RAMP3 cAMP assays (DiscoveRx, Fremont, Calif.) were used. The assays were performed in duplicate at a single concentration, and EC50 and IC50 determinations were performed in duplicate using 10-point dose response curves, 3-fold dilutions at a starting concentration.

Results

The pharmacology of superagonistic activity of synthetic analogs was studied in cells that stably express CLR/RAMP1 (1321 N1 cells), CLR/RAMP2 (CHO-K1 cells), or CLR/RAMP3 (CHO-K1 cells) receptors. In receptor-activation assays using 0.03-1000 nM doses of wild type ligands and modified analogs, the half-maximally effective concentration ($EC_{50}$) of adrenomedullin in CLR/RAMP2 receptor is approximately 13-26 nM, and the $EC_{50}$ of CLR/RAMP1-specific β-CGRP in CLR/RAMP1 receptor is approximately 0.4-1.5 nM (Table 2).

Additional controls of wild-type ADM peptides (SEQ ID NOS: 53 and 54) and IMD peptide (SEQ ID NO: 52) showed that these peptides are low potency ligands for CLR/RAMP1 receptor. The $EC_{50}$ for these wild-type ADM peptides are between 9-12 nM whereas the $EC_{50}$ for wild-type IMD was 70 nM. Comparison of the bioactivity of synthetic analogs showed that six principle chimeric peptides of ADM and IMD (SEQ ID NOS: 55-60) have low potency or are inactive in stimulating CLR/RAMP1 and/or CLR/RAMP2 receptors.

Surprisingly, a mini-PEG and a palmitoylation modifications at the N-terminus of select peptides (SEQ ID NOS: 28-29) increased the potency of these peptides on CLR/RAMP1 or CLR/RAMP2 by 10 to 1000 fold. Additional testing showed that select acylation in these peptides and additional chimeric peptides also led to significant increases in potency (SEQ ID NOS: 30-51, 92, 147, and 213). The $EC_{50}$ for stimulating CLR/RAMP1 and 2 receptors by most of these synthetic peptides is at high picomolar ranges (i.e., <1 nM).

Importantly, several of these synthetic peptides (SEQ ID NOS: 28, 30, 31, 34, and 36) also exhibited a >110% maximum activity in CLR/RAMP2 receptor when compared to adrenomedullin. In addition, some of these potent agonistic peptides represent miniaturized agonists. For example, SEQ ID NOS: 48 and 92 contain only 36 amino acids, which are much smaller than the 39- or 40-amino-acid wild type ADM and IMD peptides. Furthermore, some of these agonistic peptides also exhibit superagonistic activities toward CLR/RAMP3. While the $EC_{50}$ of ADM for CLR/RAMP3 receptor was approximately 0.4 nM (Table 2), the $EC_{50}$ of SEQ ID NOS: 28 and 48 were 0.06-0.07 nM. These data thus demonstrate that these synthetic agonists are pan-specific superagonists for CLR/RAMP1, 2, and/or 3 receptors.

The increases in potency for these synthetic ligands are specific and unique to these ligands. Other chimeric peptides with the N-terminal mini-PEG and/or palmitoylation modifications (SEQ ID NOS: 61-68), nonacylated truncated chimeric peptide (SEQ ID NO: 93), acylated chimeric CGRP-ADM peptide (SEQ ID NO: 104), acylated chimeric ADM-IMD-ADM peptide (SEQ ID NO: 105), and acylated truncated CGRP (SEQ ID NO: 108) did not exhibit increases in potency for CLR/RAMP1 and 2 receptors.

Taking advantage of these observations, we then sought to identify superagonist that is selective for CLR/RAMP2 receptor, and tested additional synthetic analogs (SEQ ID NOS: 71-74). The results showed that a palmitoylation modification of CGRP (SEQ ID NO: 74) did not affect the characteristics of CGRP activity. Likewise, palmitoylation at the N-terminus of ADM peptides of different lengths (SEQ ID NOS: 71-73) only moderately increased the potency of these peptides on CLR/RAMP1 and 2 receptors. By contrast, a specific modification with both a mini-PEG motif and a palmitoylation (SEQ ID NO: 69-70) of ADM peptide decreased the $EC_{50}$ to low nanomolar or subnanomolar concentration and maintained a preference for CLR/RAMP2 receptor. We also showed that the mini-PEG and palmitoylation modification of ADM (SEQ ID NO: 69) increases the maximum activity of CLR/RAMP2 receptor to 147%. In addition, we discovered that select ADM and chimeric analogs with truncation in the middle of the sequences generated miniaturized CLR/RAMP2-selective analogs (SEQ ID NOS: 94, 101, 103, 110, 210, 211, and 214). These data show that these ligands represent CLR/RAMP2-selective superagonists.

In addition to palmitoylation and mini-PEG modification, we have synthesized and analyzed additional ADM and IMD analogs with compounded acylation/PEG/amino acid modifications (e.g., the R1 in Formula I-IV). These compounded acylation/PEG/amino acid modifications are positioned on the side chain of N-terminal lysine residue. These modifications are represented by a structure of Formula (W')(X')n(Y')n'(Z')n", wherein W' is a fatty acid, a long-chain fatty dicarboxylic acid, a fatty acid derivative or empty; X' is a PEG group, glutamic acid, γ-glutamic acid, a proteinogenic or non-proteinogenic amino acid, Lys, or empty; Y' is a PEG group, glutamic acid, γ-glutamic acid, a proteinogenic or non-proteinogenic amino acid, Lys, or empty; Z' is a proteinogenic amino acid, a non-proteinogenic amino acid, Lys, or empty; and each of n, n' and n" is an independently selected integer from 1 to 20. Example of agonistic analogs with this type of modifications include those of SEQ ID NOS: 150-159.

The results of these experiments, with the positive control values, are listed in Table 2. The results demonstrate the surprisingly high potency of the selected peptides. For example, many have $EC_{50}$ concentrations in the high picomolar range compared to the high nanomolar $EC_{50}$ concentration of wild type-peptides.

TABLE 2

List of agonistic activity of synthetic CLR/RAMP receptor agonists

| Identity | CLR/RAMP1 EC50 (nM) | Max Activity % of positive control | CLR/RAMP2 EC50 (nM) | Max Activity % of positive control | CLR/RAMP3 EC50 (nM) | Max Activity % of positive control |
|---|---|---|---|---|---|---|
| Wild type ADM positive | | | 13-26 | 100 | 0.4 | 104 |
| Wild type CGRP-β positive | 0.4-1.5 | 100 | | | | |
| Pan-specific superagonists | | | | | | |
| (SEQ ID NO: 28) | 0.3 | 54 | 0.5 | 143 | 0.06 | 117 |
| (SEQ ID NO: 29) | 3 | 54 | 3 | 94 | | |
| (SEQ ID NO: 30) | 0.4 | 51 | 0.6 | 126 | | |
| (SEQ ID NO: 31) | 0.8 | 47 | 0.9 | 110 | | |
| (SEQ ID NO: 32) | 0.5 | 48 | 1 | 119 | | |
| (SEQ ID NO: 33) | 0.3 | 62 | 0.4 | 101 | | |
| (SEQ ID NO: 34) | 0.2 | 50 | 0.7 | 120 | | |
| (SEQ ID NO: 35) | 0.8 | 42 | 1 | 116 | | |
| (SEQ ID NO: 36) | 0.6 | 58 | 0.9 | 130 | | |
| (SEQ ID NO: 37) | 1.3 | 55 | 4 | 72 | | |
| (SEQ ID NO: 38) | 0.5 | 89 | 0.7 | 97 | | |
| (SEQ ID NO: 39) | 0.2 | 82 | 0.5 | 86 | | |
| (SEQ ID NO: 40) | 2 | 99 | 1 | 86 | | |
| (SEQ ID NO: 41) | 0.4 | 75 | 0.9 | 105 | | |
| (SEQ ID NO: 42) | 1.3 | 56 | 0.2 | 76 | | |
| (SEQ ID NO: 43) | 0.5 | 39 | 0.2 | 30 | | |
| (SEQ ID NO: 44) | 0.1 | 58 | 0.2 | 69 | | |
| (SEQ ID NO: 45) | 0.1 | 50 | 0.3 | 79 | | |
| (SEQ ID NO: 46) | 0.7 | 60 | 0.5 | 104 | | |
| (SEQ ID NO: 47) | 1.5 | 85 | 0.4 | 64 | | |
| (SEQ ID NO: 48) | 0.3 | 78 | 0.2 | 77 | 0.07 | 141 |
| (SEQ ID NO: 49) | 0.5 | 66 | 0.4 | 83 | | |
| (SEQ ID NO: 50) | 1.2 | 65 | 1.2 | 87 | | |
| (SEQ ID NO: 51) | 0.2 | 65 | 0.3 | 107 | | |
| (SEQ ID NO: 92) | 0.4 | 61 | 0.3 | 67 | 0.2 | 156 |
| (SEQ ID NO: 147) | 0.14 | 109 | 0.71 | 90 | | |
| (SEQ ID NO: 150) | 2.4 | 94 | 1.9 | 60 | | |
| (SEQ ID NO: 151) | 0.5 | 85 | 1.4 | 134 | | |
| (SEQ ID NO: 152) | 2.5 | 80 | 2.4 | 132 | | |
| (SEQ ID NO: 153) | 7.3 | 78 | 3.5 | 108 | | |
| (SEQ ID NO: 154) | 1.6 | 83 | 1.7 | 112 | | |
| (SEQ ID NO: 155) | 0.6 | 81 | 1.8 | 95 | | |
| (SEQ ID NO: 156) | 0.8 | 88 | 1.2 | 91 | | |
| (SEQ ID NO: 157) | 2.8 | 100 | 1.8 | 95 | | |
| (SEQ ID NO: 158) | 5.7 | 95 | 3.6 | 113 | | |
| (SEQ ID NO: 159) | 1.3 | 90 | 1.1 | 60 | | |
| (SEQ ID NO: 213) | 0.7 | 115 | 0.7 | 107 | | |
| Wild-type IMD, ADM, and CGRP | | | | | | |
| (SEQ ID NO: 52) | 116 | 72 | 70 | 67 | | |
| (SEQ ID NO: 53) | 540 | 69 | 9 | 102 | | |
| (SEQ ID NO: 54) | 564 | 63 | 12 | 91 | 2.2 | 130 |
| (SEQ ID NO: 143) | 1.8-2.9 | 103 | >1000 | | | |
| Inactive or low potency chimeric peptides | | | | | | |
| (SEQ ID NO: 55) | >1000 | 1 | >1000 | 8 | | |
| (SEQ ID NO: 56) | 224 | 58 | 17 | 111 | | |
| (SEQ ID NO: 57) | 909 | 53 | 149 | 94 | | |
| (SEQ ID NO: 58) | >1000 | 0 | >1000 | 1 | | |
| (SEQ ID NO: 59) | 31 | 95 | 18 | 115 | | |
| (SEQ ID NO: 60) | 16 | 100 | 3 | 114 | | |
| (SEQ ID NO: 61) | 175 | 70 | 6 | 92 | | |
| (SEQ ID NO: 62) | >1000 | 2 | >1000 | 8 | | |
| (SEQ ID NO: 63) | 180 | 61 | 7 | 94 | | |
| (SEQ ID NO: 64) | >1000 | 1 | >1000 | 8 | | |
| (SEQ ID NO: 65) | 234 | 73 | 19 | 99 | | |
| (SEQ ID NO: 66) | >1000 | 4 | >1000 | 4 | | |
| (SEQ ID NO: 67) | 1 | 78 | >1000 | 77 | | |
| (SEQ ID NO: 68) | 11 | 48 | 7 | 70 | | |
| (SEQ ID NO: 93) | 771 | 53 | 17 | 85 | | |
| (SEQ ID NO: 104) | >1000 | 2 | >1000 | 4 | | |
| (SEQ ID NO: 105) | >1000 | 33 | 19 | 40 | | |
| (SEQ ID NO: 108) | >1000 | 6 | >1000 | 6 | | |

TABLE 2-continued

List of agonistic activity of synthetic CLR/RAMP receptor agonists

CLR/RAMP2-specific superagonists

| Identity | CLR/RAMP1 EC50 (nM) | Max Activity % of positive control | CLR/RAMP2 EC50 (nM) | Max Activity % of positive control | CLR/RAMP3 EC50 (nM) | Max Activity % of positive control |
|---|---|---|---|---|---|---|
| (SEQ ID NO: 69) | 13 | 70 | 0.6 | 147 | 0.6 | 127 |
| (SEQ ID NO: 70) | 619 | 69 | 1.1 | 68 | | |
| (SEQ ID NO: 94) | 11 | 67 | 1.3 | 82 | | |
| (SEQ ID NO: 101) | 7.7 | 56 | 0.3 | 74 | 0.5 | 129 |
| (SEQ ID NO: 103) | 4.5 | 96 | 0.7 | 77 | 0.3 | 140 |
| (SEQ ID NO: 110) | 43 | 71 | 6.4 | 74 | | |
| (SEQ ID NO: 210) | 7.1 | 77 | 1.4 | 47 | | |
| (SEQ ID NO: 211) | 8 | 91 | 0.9 | 22 | | |
| (SEQ ID NO: 214) | 1.1 | 112 | 0.4 | 99 | | |

Low potency CLR/RAMP1- or CLR/RAMP2-specific peptides

| | | | | | | |
|---|---|---|---|---|---|---|
| (SEQ ID NO: 71) | 24 | 53 | 3 | 78 | | |
| (SEQ ID NO: 72) | 28 | 45 | 3 | 90 | | |
| (SEQ ID NO: 73) | 34 | 79 | 49 | 46 | | |
| (SEQ ID NO: 74) | 2 | 95 | >1000 | 12 | | |

| Identity | CLR/RAMP1 EC50 (nM) | Max Activity % of positive control | CLR/RAMP2 EC50 (nM) | Max Activity % of positive control | CLR/RAMP3 EC50 (nM) | Max Activity % of positive control |
|---|---|---|---|---|---|---|
| Wild type ADM positive | | | 13-26 | 100 | 0.4 | 104 |
| Wild type CGRP-β positive | 0.4-1.5 | 100 | | | | |

Pan-specific superagonists

| | | | | | | |
|---|---|---|---|---|---|---|
| (SEQ ID NO: 28) | 0.3 | 54 | 0.5 | 143 | 0.06 | 117 |
| (SEQ ID NO: 29) | 3 | 54 | 3 | 94 | | |
| (SEQ ID NO: 30) | 0.4 | 51 | 0.6 | 126 | | |
| (SEQ ID NO: 31) | 0.8 | 47 | 0.9 | 110 | | |
| (SEQ ID NO: 32) | 0.5 | 48 | 1 | 119 | | |
| (SEQ ID NO: 33) | 0.3 | 62 | 0.4 | 101 | | |
| (SEQ ID NO: 34) | 0.2 | 50 | 0.7 | 120 | | |
| (SEQ ID NO: 35) | 0.8 | 42 | 1 | 116 | | |
| (SEQ ID NO: 36) | 0.6 | 58 | 0.9 | 130 | | |
| (SEQ ID NO: 37) | 1.3 | 55 | 4 | 72 | | |
| (SEQ ID NO: 38) | 0.5 | 89 | 0.7 | 97 | | |
| (SEQ ID NO: 39) | 0.2 | 82 | 0.5 | 86 | | |
| (SEQ ID NO: 40) | 2 | 99 | 1 | 86 | | |
| (SEQ ID NO: 41) | 0.4 | 75 | 0.9 | 105 | | |
| (SEQ ID NO: 42) | 1.3 | 56 | 0.2 | 76 | | |
| (SEQ ID NO: 43) | 0.5 | 39 | 0.2 | 30 | | |
| (SEQ ID NO: 44) | 0.1 | 58 | 0.2 | 69 | | |
| (SEQ ID NO: 45) | 0.1 | 50 | 0.3 | 79 | | |
| (SEQ ID NO: 46) | 0.7 | 60 | 0.5 | 104 | | |
| (SEQ ID NO: 47) | 1.5 | 85 | 0.4 | 64 | | |
| (SEQ ID NO: 48) | 0.3 | 78 | 0.2 | 77 | 0.07 | 141 |
| (SEQ ID NO: 49) | 0.5 | 66 | 0.4 | 83 | | |
| (SEQ ID NO: 50) | 1.2 | 65 | 1.2 | 87 | | |
| (SEQ ID NO: 51) | 0.2 | 65 | 0.3 | 107 | | |
| (SEQ ID NO: 92) | 0.4 | 61 | 0.3 | 67 | 0.2 | 156 |
| (SEQ ID NO: 147) | 0.14 | 109 | 0.71 | 90 | | |
| (SEQ ID NO: 150) | 2.4 | 94 | 1.9 | 60 | | |
| (SEQ ID NO: 151) | 0.5 | 85 | 1.4 | 134 | | |
| (SEQ ID NO: 152) | 2.5 | 80 | 2.4 | 132 | | |
| (SEQ ID NO: 153) | 7.3 | 78 | 3.5 | 108 | | |
| (SEQ ID NO: 154) | 1.6 | 83 | 1.7 | 112 | | |
| (SEQ ID NO: 155) | 0.6 | 81 | 1.8 | 95 | | |
| (SEQ ID NO: 156) | 0.8 | 88 | 1.2 | 91 | | |
| (SEQ ID NO: 157) | 2.8 | 100 | 1.8 | 95 | | |
| (SEQ ID NO: 158) | 5.7 | 95 | 3.6 | 113 | | |
| (SEQ ID NO: 159) | 1.3 | 90 | 1.1 | 60 | | |
| (SEQ ID NO: 213) | 0.7 | 115 | 0.7 | 107 | | |

Wild-type IMD, ADM, and CGRP

| | | | | | | |
|---|---|---|---|---|---|---|
| (SEQ ID NO: 52) | 116 | 72 | 70 | 67 | | |
| (SEQ ID NO: 53) | 540 | 69 | 9 | 102 | | |
| (SEQ ID NO: 54) | 564 | 63 | 12 | 91 | 2.2 | 130 |
| (SEQ ID NO: 143) | 1.8-2.9 | 103 | >1000 | | | |

Inactive or low potency chimeric peptides

| | | | | | | |
|---|---|---|---|---|---|---|
| (SEQ ID NO: 55) | >1000 | 1 | >1000 | 8 | | |
| (SEQ ID NO: 56) | 224 | 58 | 17 | 111 | | |
| (SEQ ID NO: 57) | 909 | 53 | 149 | 94 | | |
| (SEQ ID NO: 58) | >1000 | 0 | >1000 | 1 | | |

TABLE 2-continued

List of agonistic activity of synthetic CLR/RAMP receptor agonists

| | | | | | | |
|---|---|---|---|---|---|---|
| (SEQ ID NO: 59) | 31 | 95 | 18 | 115 | | |
| (SEQ ID NO: 60) | 16 | 100 | 3 | 114 | | |
| (SEQ ID NO: 61) | 175 | 70 | 6 | 92 | | |
| (SEQ ID NO: 62) | >1000 | 2 | >1000 | 8 | | |
| (SEQ ID NO: 63) | 180 | 61 | 7 | 94 | | |
| (SEQ ID NO: 64) | >1000 | 1 | >1000 | 8 | | |
| (SEQ ID NO: 65) | 234 | 73 | 19 | 99 | | |
| (SEQ ID NO: 66) | >1000 | 4 | >1000 | 4 | | |
| (SEQ ID NO: 67) | 1 | 78 | >1000 | 77 | | |
| (SEQ ID NO: 68) | 11 | 48 | 7 | 70 | | |
| (SEQ ID NO: 93) | 771 | 53 | 17 | 85 | | |
| (SEQ ID NO: 104) | >1000 | 2 | >1000 | 4 | | |
| (SEQ ID NO: 105) | >1000 | 33 | 19 | 40 | | |
| (SEQ ID NO: 108) | >1000 | 6 | >1000 | 6 | | |
| CLR/RAMP2-specific superagonists | | | | | | |
| (SEQ ID NO: 69) | 13 | 70 | 0.6 | 147 | 0.6 | 127 |
| (SEQ ID NO: 70) | 619 | 69 | 1.1 | 68 | | |
| (SEQ ID NO: 94) | 11 | 67 | 1.3 | 82 | | |
| (SEQ ID NO: 101) | 7.7 | 56 | 0.3 | 74 | 0.5 | 129 |
| (SEQ ID NO: 103) | 4.5 | 96 | 0.7 | 77 | 0.3 | 140 |
| (SEQ ID NO: 110) | 43 | 71 | 6.4 | 74 | | |
| (SEQ ID NO: 210) | 7.1 | 77 | 1.4 | 47 | | |
| (SEQ ID NO: 211) | 8 | 91 | 0.9 | 22 | | |
| (SEQ ID NO: 214) | 1.1 | 112 | 0.4 | 99 | | |
| Low potency CLR/RAMP1- or CLR/RAMP2-specific peptides | | | | | | |
| (SEQ ID NO: 71) | 24 | 53 | 3 | 78 | | |
| (SEQ ID NO: 72) | 28 | 45 | 3 | 90 | | |
| (SEQ ID NO: 73) | 34 | 79 | 49 | 46 | | |
| (SEQ ID NO: 74) | 2 | 95 | >1000 | 12 | | |

For the analysis of antagonistic activity, synthetic analogs were pre-incubated with the cells before adding the reference ligand at its EC80. The assays showed that the wild type ADM22-52 (SEQ ID NO:75) inhibited the CGRP-stimulated CLR/RAMP1 and ADM-stimulated CLR/RAMP2 receptor activation with IC50 of >20000 and 631 nM, respectively (Table 3). On the other hand, the CLR/RAMP1-specific CGRP8-37 (SEQ ID NO: 137) has an $IC_{50}$ of 133 and >10000 nM, for CLR/RAMP1 and CLR/RAMP2, respectively.

These data are consistent with the literature that CGRP8-37 and ADM22-52 are low potency antagonists specific for CLR/RAMP1 and CLR/RAMP2, respectively. We have also studied chimeric antagonistic analogs, consisting of ADM and IMD sequence (SEQ ID NO: 76). It appears to have only mildly improved antagonistic activity toward CLR/RAMP1 and 2 receptors when compared to ADM22-52. The $IC_{50}$ of this peptide for CGRP-stimulated CLR/RAMP1 and ADM-stimulated CLR/RAMP2 receptor signaling was 1123 and 289 nM, respectively. By contrast, the chimeric peptide with an N-terminal palmitoylation, or a palmitoylation and mini-PEG modification of the present invention (SEQ ID NOS: 77-78, 112, 114, 119, 120-125, and 139) exhibited highly potent antagonistic activity toward CGRP-stimulated CLR/RAMP1 and/or ADM-stimulated CLR/RAMP2 receptor signaling.

Among these antagonists, SEQ ID NOS: 77-78, 112, 121, 125, 148, and 149 are pan-specific. SEQ ID NOS: 114, 120, 122-124, 139, 140, 145, 146, 190-192 are CLR/RAMP1-selective; whereas SEQ ID NO: 119 is CLR/RAMP2-selective. The $IC_{50}$ for CGRP-stimulated CLR/RAMP1 and ADM-stimulated CLR/RAMP2 receptor signaling for these analogs was 1.8-9.9 and 0.6-47 nM, respectively. Two synthetic peptides that have been reported to exhibit potent antagonistic activities for CLR/RAMP receptors (SEQ ID NOS: 115 and 116; Table 3) did not show superantagonistic activities in the same assays (Robinson et al., (2009) J Pharmacol Exp Ther 331:513-521). Moreover, studies of the CLR/RAMP3 receptor-activation activities showed that select peptides are super-antagonists for CLR/RAMP3 as well. Unlike CGRP8-37 and ADM22-52, which have an $IC_{50}$ of 574 and 330 nM for CLR/RAMP3, respectively; the $IC_{50}$ of SEQ ID NOS: 78, 112, 114, 119, 120-122, and 124 were 0.8-9.2 nM. It is also important to note that some of these super-antagonists are miniaturized antagonists which contain only 17-28 amino acids. In contrast, the CGRP8-37 and ADM22-52 contain 30 and 31 amino acids, respectively.

Moreover, we have designed and synthesized acylated miniaturized chimeric antagonistic peptides which combines part of the ADM and CGRP sequences. Functional analysis showed that these ADM-CGRP chimera represent super-antagonists of CLR/RAMP1, and exhibits IC50 for CLR/RAMP1 at subnanomolar range. For example, the IC50 for CLR/RAMP1 of SEQ ID NO: 142 is less than 0.5 nM, whereas its IC50 for CLR/RAMP2 is >200 nM. These results are surprising and specific. An acylated peptide consist the corresponding region of IMD (SEQ ID NO:141) and a peptide with the corresponding CGRP sequence (SEQ ID NO:144) have minimal antagonizing activities toward CLR/RAMP1 or CLR/RAMP2 (Table 3).

These data demonstrate that the N-terminally modified chimeric peptides (SEQ ID NOS: 77-78, 112, 114, 119, 120-125, or 139) have antagonistic activities one to two orders of magnitude stronger than the parental peptide (SEQ ID NO: 76), or CGRP- and ADM-derived antagonists. Therefore, these modified chimeric or truncated peptides are potent pan-specific, CLR/RAMP1-selective, or CLR/RAMP2-selective super-antagonists for CLR/RAMP1, 2, and 3 receptors.

Likewise, we have synthesized and analyzed additional antagonistic analogs with additional PEG modifications, in which the PEG modifications are high molecular weight PEGs. Example of antagonistic analogs with these modifications include those of SEQ ID NOS: 190-192.

To study the bioactivities of MRLs, we employed additional in vitro receptor-activation assays with cultured cells expressing recombinant somatostatin receptor SSTR2, neurotensin receptor 1 (NTSR1), apelin receptor AGTRL1, bradykinin receptor 1 (BDKRB1), or type 1 angiotensin II receptor AGTR1. The agonistic activities toward SSTR2, NTSR1, and AGTRL1 were assayed with an SSTR2 arrestin assay, an NTSR1 calcium flux assay, and an AGTRL1 cAMP assay (Discoverx Inc.), respectively. The antagonistic activities toward BDKRB1 and AGTR1 were assayed with a BDKRB1 calcium flux assay and an AGTR1 calcium flux assay (Discoverx Inc.), respectively.

For the analysis of Gs-coupled cAMP production, cAMP Hunter cell lines were expanded from freezer stocks, and cells were seeded in a total volume of 20 µL into white walled, 384-well microplates and incubated at 37 C for the appropriate time prior to testing. The cAMP modulation was determined using the DiscoverX HitHunter cAMP XS+ assay. For agonistic activity determination, cells were incubated with sample to induce response. Media was aspirated from cells and replaced with 15 µL 2:1 HBSS/10 mM Hepes: cAMP XS+Ab reagent. Intermediate dilution of sample stocks was performed to generate 4× sample in assay buffer, and 5 µL of 4× sample was added to cells and incubated at 37 C or room temperature for 30 or 60 minutes. Vehicle concentration was 1%.

For the determination of antagonistic activity, cells were pre-incubated with sample followed by agonist challenge at the EC80 concentration. Media was aspirated from cells and replaced with 10 µL 1:1 HBSS/Hepes: cAMP XS+Ab reagent, and 5 µL of 4× compound was added to the cells and incubated at 37 C or room temperature for 30 minutes. Then, 5 µL of 4× EC80 agonist was added to cells and incubated at 37 C or room temperature for 30 or 60 minutes. After appropriate compound incubation, assay signal was generated through incubation with 20 µL cAMP XS+ED/CL lysis cocktail for one hour followed by incubation with 20 µL cAMP XS+EA reagent for three hours at room temperature. Microplates were read following signal generation with a PerkinElmer Envision™ instrument for chemiluminescent signal detection.

The compound activity was analyzed using a CBIS data analysis suite (Chem Innovation, CA). For Gs-coupled agonistic assays, percentage activity is calculated using the following formula: % Activity=100%×(mean RLU of test sample−mean RLU of vehicle control)/(mean RLU of MAX control−mean RLU of vehicle control).

For the antagonistic activity assay, percentage inhibition is calculated using the following formula: % Inhibition=100%×(1−(mean RLU of test sample−mean RLU of vehicle control)/(mean RLU of EC80 control−mean RLU of vehicle control)).

For the analysis of calcium flux, cell lines were expanded from freezer stocks and seeded in a total volume of 20 µL into black-walled, clear-bottom, Poly-D-lysine coated 384-well microplates and incubated at 37 C for the appropriate time prior to testing. Assays were performed in 1× Dye Loading Buffer consisting of 1× Dye, 1× Additive A and 2.5 mM Probenecid in HBSS/20 mM Hepes. Cells were loaded with dye prior to testing. Media was aspirated from cells and replaced with 20 µL Dye Loading Buffer. Cells were incubated for 30-60 minutes at 37 C. For agonist determination, cells were incubated with sample to induce response. After dye loading, cells were removed from the incubator and 10 µL HBSS/20 mM Hepes was added. Vehicle was included in the buffer when performing agonist dose curves to define the EC80 for antagonist assays. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS), and calcium mobilization was monitored for 2 minutes and 10 µL 4× sample in HBSS/20 mM Hepes was added to the cells 5 seconds into the assay.

For antagonist determination, cells were pre-incubated with sample followed by agonist challenge at the EC80 concentration. Intermediate dilution of sample stocks was performed to generate 3× sample in assay buffer. After dye loading, cells were removed from the incubator and 10 µL 3× sample was added. Cells were incubated for 30 minutes at room temperature in the dark to equilibrate plate temperature. Vehicle concentration was 1%. Compound antagonistic activity was measured on a FLIPR Tetra (MDS), and calcium mobilization was monitored for 2 minutes and 10 µL EC80 agonist in HBSS/20 mM Hepes was added to the cells 5 seconds into the assay.

The compound activity was analyzed using a CBIS data analysis suite (Chem Innovation, CA), and percentage activity is calculated using the following formula: % Activity=100%×(mean RFU of test sample−mean RFU of vehicle control)/(mean MAX RFU control ligand−mean RFU of vehicle control). For antagonist assays, percentage inhibition is calculated using the following formula: % Inhibition=100%×(1−(mean RFU of test sample−mean RFU of vehicle control)/(mean RFU of EC80 control−mean RFU of vehicle control)).

For the Arrestin assays, Path Hunter cell lines (Discoverx Inc.) were expanded from freezer stocks, and seeded in a total volume of 20 µL into white walled, 384-well microplates and incubated at 37 C for the appropriate time prior to testing. For agonist determination, cells were incubated with sample to induce response. Intermediate dilution of sample stocks was performed to generate 5× sample in assay buffer, and 5 µL of 5× sample was added to cells and incubated at 37 C or room temperature for 90 to 180 minutes. Vehicle concentration was 1%.

For antagonistic activity determination, cells were pre-incubated with antagonist followed by agonist challenge at the EC80 concentration. Intermediate dilution of sample stocks was performed to generate 5× sample in assay buffer, and 5 µL of 5× sample was added to cells and incubated at 37° C. or room temperature for 30 minutes. Vehicle concentration was 1%. Then, 5 µL of 6× EC80 agonist in assay buffer was added to the cells and incubated at 37 C or room temperature for 90 or 180 minutes.

Assay signal was generated through a single addition of 12.5 or 15 µL (50% v/v) of PathHunter Detection reagent cocktail, followed by a one hour incubation at room temperature. The microplates were read following signal generation with a PerkinElmer Envision™ instrument for chemiluminescent signal detection.

The compound activity was analyzed using a CBIS data analysis suite (Chem Innovation, CA). For agonist mode assays, percentage activity was calculated using the following formula: % Activity=100%×(mean RLU of test sample−mean RLU of vehicle control)/(mean MAX control ligand−mean RLU of vehicle control). For antagonistic activity assays, percentage inhibition was calculated using the following formula: % Inhibition=100%×(1−(mean RLU of test sample−mean RLU of vehicle control)/(mean RLU of EC80 control−mean RLU of vehicle control)).

In the SSTR2 arrestin assay, the positive control, somatostatin-28 (SEQ ID NO: 217), exhibits an $EC_{50}$ of 6.8 nM (Table 4). In the NTSR1 calcium flux assay, the positive control, wild-type neurotensin (Glp-LYENKPRRPYIL; SEQ ID NO: 221) and [Lys 8,9] Neurotensin (SEQ ID NO: 222), exhibit an $EC_{50}$ of 0.051 nM and 0.017 nM, respectively. In AGTRL1 cAMP assay, the positive control, apelin-13 (SEQ ID NO: 225), exhibits an $EC_{50}$ of 0.57 nM. In BDKRB1 calcium flux assay, the positive control, [Lys-des-Arg9]-Bradykinin (SEQ ID NO: 230), exhibits an $EC_{50}$ of 0.91 nM. In AGTR1 calcium flux assay, the positive control, angiotensin II (SEQ ID NO: 232), exhibits an $EC_{50}$ of 0.34 nM. In the AGTR1 calcium flux assay, a positive antagonist control, telmisartan, exhibits an $IC_{50}$ of 0.62 nM.

Using these assays, we found that MRL compounds (SEQ ID NOS: 218, 223, 224, 228, 231, and 234; Table 4) are bioactive agonist or antagonist for CLR/RAMP receptors and one of these non-CLR/RAMP GPCRs. For example, the SSTR2 and CLR/RAMP agonist MRL (SEQ ID NO: 218) exhibits potent SSTR2-activation activity with an $EC_{50}$ of 16.9 nM. The NTSR1 and CLR/RAMP agonist (SEQ ID NO: 223) exhibits potent neurotensin receptor 1-activation activity with an $EC_{50}$ of 11.3 nM. On the other hand, the NTSR1 agonist and CLR/RAMP antagonist MRL (SEQ ID NO: 224) exhibits an $EC_{50}$ of 26.1 nM on NTSR1. The AGTRL1 and CLR/RAMP agonist MRL (SEQ ID NO: 228) exhibits potent AGTRL1-activation activity with an $EC_{50}$ of 38.5 nM. The BDKRB1 antagonist and CLR/RAMP agonist MRL (SEQ ID NO: 231) exhibits potent BDKRB1 antagonizing activity with an $IC_{50}$ of 79.4 nM. The AGTR1 and CLR/RAMP antagonist MRL (SEQ ID NO: 234) exhibits potent AGTR1 antagonizing activity with an $IC_{50}$ of 19.9 nM.

The CLR/RAMP ligand components of these MRL also exhibit potent CLR/RAMP receptor-regulatory activities. For example, the $EC_{50}$ of the NTSR1 agonist/CLR/RAMP agonist MRL (SEQ ID NO: 223), AGTRL1 agonist/CLR/RAMP agonist MRL (SEQ ID NO: 228), BDKRB1 antagonist/CLR/RAMP agonist MRL (SEQ ID NO: 231), AGTR1 antagonist/CLR/RAMP agonist MRL (SEQ ID NO: 224) for CLR/RAMP1 are 0.8, 0.6, 0.8 and 0.3 nM (Table 4). On the other hand, the $IC_{50}$ of SSTR2 agonist/CLR/RAMP antagonist MRL (SEQ ID NO: 218) and NTSR1 agonist/CLR/RAMP antagonist MRL (SEQ ID NO: 224) for CLR/RAMP1 are 2 and <0.5 nM, respectively.

TABLE 3

List of antagonistic activity of synthetic CLR/RAMP receptor antagonists

| Identity | CLR/RAMP1 IC50 (nM) | Max Activity % of positive control | CLR/RAMP2 IC50 (nM) | Max Activity % of positive control | CLR/RAMP3 IC50 (nM) | Max Activity % of positive control |
|---|---|---|---|---|---|---|
| CLR/RAMP1 antagonist | | | | | | |
| BIBN4096 | 0.05 | 105 | >100 | 0 | | |
| Pan-specific super-antagonist | | | | | | |
| (SEQ ID NO: 77) | 9.9 | 101 | 47 | 100 | | |
| (SEQ ID NO: 78) | 4.8 | 104 | 34 | 107 | 0.8 | 101 |
| (SEQ ID NO: 112) | 1.8 | 99 | 5.3 | 97 | 2.3 | 99 |
| (SEQ ID NO: 121) | 3.2 | 94 | 4.9 | 104 | 1.8 | 100 |
| (SEQ ID NO: 125) | 7 | 93 | 7.1 | 100 | | |
| (SEQ ID NO: 148) | 1.7 | 100 | 1.6 | 97 | | |
| (SEQ ID NO: 149) | 2.3 | 101 | 1.2 | 99 | | |
| ADM22-52 and CGRP8-37 | | | | | | |
| (SEQ ID NO: 75) | >20000 | 22 | 631 | 100 | 330 | 99 |
| (SEQ ID NO: 137) | 133 | 95 | >10,000 | 15 | 574 | 96 |
| Low potency antagonists | | | | | | |
| (SEQ ID NO: 76) | 1123 | 106 | 289 | 101 | | |
| (SEQ ID NO: 115) | 1878 | 99 | 117 | 100 | 115 | 98 |
| (SEQ ID NO: 116) | 152 | 101 | 7.3 | 101 | 53 | 98 |
| (SEQ ID NO: 141) | 3837 | 43 | >10,000 | 14 | | |
| (SEQ ID NO: 144) | 206 | 98 | >10,000 | 0 | | |
| CLR/RAMP1-specific super-antagonist | | | | | | |
| (SEQ ID NO: 114) | 4.8 | 101 | 146 | 87 | 8.4 | 102 |
| (SEQ ID NO: 120) | 5.8 | 94 | 85 | 98 | 9.2 | 100 |
| (SEQ ID NO: 122) | 7.3 | 95 | 61 | 100 | 4.1 | 100 |
| (SEQ ID NO: 123) | 4.7 | 94 | 50 | 101 | | |
| (SEQ ID NO: 124) | 6.7 | 95 | 64 | 103 | 5.9 | 102 |
| (SEQ ID NO: 139) | 3.8 | 98 | 462 | 101 | | |
| (SEQ ID NO: 140) | 1.2 | 100 | 78 | 90 | | |
| (SEQ ID NO: 145) | <0.5 | 99 | 24 | 100 | | |
| (SEQ ID NO: 146) | <0.5 | 102 | 59 | 98 | | |
| (SEQ ID NO: 190) | 74.1 | 104 | 1682 | 51 | | |
| (SEQ ID NO: 191) | 30.5 | 98 | 427 | 101 | | |
| (SEQ ID NO: 192) | 16.6 | 101 | 242 | 104 | | |
| CLR/RAMP2-specific super-antagonist | | | | | | |
| (SEQ ID NO: 119) | 21 | 95 | 0.6 | 101 | 1.5 | 102 |
| CLR/RAMP1-specific super-antagonistic ADM/CGRP peptide sequence | | | | | | |
| (SEQ ID NO: 142) | <0.5 | 100 | 214 | 80 | | |

TABLE 4

List of receptor-regulatory activities of MRLs

| Identity | CLR/RAMP1 EC50 (nM) | Max Activity* | IC50 (nM) | Max Activity | CLR/RAMP2 EC50 (nM) | Max Activity | IC50 (nM) | Max Activity | SSTR2 EC50 (nM) | Max Activity | NTSR1 EC50 (nM) | Max Activity | AGTRL1 EC50 (nM) | Max Activity | BDKRB1 IC50 (nM) | Max Activity | AGTR1 EC50 (nM) | Max Activity | AGTR1 IC50 (nM) | Max Activity |
|---|---|---|---|---|---|---|---|---|---|---|---|---|---|---|---|---|---|---|---|---|
| CLR/RAMP1 antagonist ||||||||||||||||||||
| BIBN 4096 | 0.05 | 105 | | >100 | 0 | | | | | | | | | | | | | | | |
| CGRP8-37 | | | 133 | 95 | | | >10,000 | 15 | | | | | | | | | | | | |
| ADM22-52 | | | >20000 | 22 | | | 631 | 100 | | | | | | | | | | | | |
| CGRP-β | 0.4-1.5 | 100 | | | | | | | | | | | | | | | | | | |
| ADM | | | | | 13-26 | 100 | | | | | | | | | | | | | | |
| Somatostatin 28 [Lys 8, 9] | | | | | | | | | 6.8 | 102 | | | | 100 | | | | | | |
| Neurotensin | | | | | | | | | | | 0.02 | | | 72 | | | | | | |
| Neurotensin | | | | | | | | | | | 0.05 | | | | | | | | | |
| Apelin 13 | | | | | | | | | | | | | 0.6 | 100 | | | | | | |
| LDA-Bradykinin | | | | | | | | | | | | | | | 0.9 | 109 | | | | |
| Angiotensin II | | | | | | | | | | | | | | | | | 0.3 | 102 | | |
| Telmisartan | | | | | | | | | | | | | | | | | | | 0.6 | 100 |
| SSTR/CLR/RAMP MRLs ||||||||||||||||||||
| (SEQ ID NO: 218) | | | 2 | 102 | | | <0.5 | 87 | 17 | 117 | | | | | | | | | | |
| NTSR1/CLR/RAMP MRLs ||||||||||||||||||||
| (SEQ ID NO: 223) | 0.8 | 102 | | | 1 | 70 | | | | | 11 | | | | | | | | | |
| (SEQ ID NO: 224) | | | <0.5 | 99 | | | 1.5 | 100 | | | 26 | | | | | | | | | |
| AGTRL1/CLR/RAMP MRLs ||||||||||||||||||||
| (SEQ ID NO: 228) | 0.6 | 130 | | | 2 | 74 | | | | | | | | | | | | | | |
| BDKRB1/CLR/RAMP MRLs ||||||||||||||||||||
| (SEQ ID NO: 231) | 0.8 | 115 | | | 1 | 46 | | | | | | | | | | | | | | |
| AGTR1/CLR/RAMP MRLs ||||||||||||||||||||
| (SEQ ID NO: 234) | 0.3 | 132 | | | 1 | 86 | | | | | | | | | | | | | | |

TABLE 4-continued

List of receptor-regulatory activities of MRLs

| | SSTR/CLR/RAMP MRLs | | |
|---|---|---|---|
| (SEQ ID NO: 218) | | | |
| | NTSR1/CLR/RAMP MRLs | | |
| (SEQ ID NO: 223) | 76 | | |
| (SEQ ID NO: 224) | 57 | | |
| | AGTRL1/CLR/RAMP MRLs | | |
| (SEQ ID NO: 228) | 38 | 97 | |
| | BDKRB1/CLR/RAMP MRLs | | |
| (SEQ ID NO: 231) | | 79 | 109 |
| | AGTR1/CLR/RAMP MRLs | | |
| (SEQ ID NO: 234) | | | 20 | 104 |

*Maximum activity is the % of positive controls

While the present embodiments have been described in some detail for purposes of clarity and understanding, one skilled in the art will appreciate that various changes in form and detail can be made without departing from the true scope of the embodiments. All figures, tables, and appendices, as well as patents, applications, and publications, referred to above, are hereby incorporated by reference in their entirety.

Control Reagents. Human β-CGRP and human ADM were employed as positive controls for CLR/RAMP1 and 2 receptor assays, respectively. In addition, peptides having the human IMD (SEQ ID NO: 52), human ADM, (SEQ ID NO: 53), and human ADM (SEQ ID NO: 54) sequences were employed as additional controls. For SSTR2 arrestin assay, NTSR1 calcium flux assay, and AGTRL1 cAMP assay, somatostatin-28 (SEQ ID NO: 217), [Lys 8,9] Neurotensin (SEQ ID NO: 221) and apelin-13 (SEQ ID NO: 225) were used as positive controls, respectively. For BDKRB1 calcium flux assay, [Lys-des-Arg9]-Bradykinin (SEQ ID NO: 230) was used as positive controls. For AGTR1 calcium flux assay, angiotensin II (SEQ ID NO: 232) was used as positive controls. For AGTR1 calcium flux assay, we also used telmisartan as an antagonistic control.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A Multiple Receptor Ligand (MRL), comprising (D-Phe)CF(D-Trp)KTCT-miniPEG-K(Pal)VQKLAHQIYQFTDKDVAPRSKISPQGY-NH$_2$ or a pharmaceutically acceptable salt thereof, wherein mini-PEG is —NH(CH$_2$CH$_2$O)$_2$CH$_2$C(=O)— and Pal is palmitoyl.

* * * * *